United States Patent
Croce et al.

(10) Patent No.: US 8,911,998 B2
(45) Date of Patent: Dec. 16, 2014

(54) METHODS FOR IDENTIFYING FRAGILE HISTIDINE TRIAD (FHIT) INTERACTION AND USES THEREOF

(75) Inventors: Carlo M. Croce, Columbus, OH (US); Francesco Trapasso, Catanzaro (IT)

(73) Assignee: The Ohio State University, Columbus, OH (US)

( * ) Notice: Subject to any disclaimer, the term of this patent is extended or adjusted under 35 U.S.C. 154(b) by 1216 days.

(21) Appl. No.: 12/739,541

(22) PCT Filed: Oct. 27, 2008

(86) PCT No.: PCT/US2008/081294
§ 371 (c)(1),
(2), (4) Date: Feb. 25, 2011

(87) PCT Pub. No.: WO2009/055773
PCT Pub. Date: Apr. 30, 2009

(65) Prior Publication Data
US 2012/0010092 A1 Jan. 12, 2012

Related U.S. Application Data

(60) Provisional application No. 61/000,480, filed on Oct. 26, 2007.

(51) Int. Cl.
*C12N 15/09* (2006.01)
*A61K 38/17* (2006.01)
*G01N 33/50* (2006.01)
*C12N 15/86* (2006.01)
*C12Q 1/68* (2006.01)

(52) U.S. Cl.
CPC ...... *C12N 15/86* (2013.01); *C12N 2710/10343* (2013.01); *A61K 38/17* (2013.01); *G01N 33/5011* (2013.01); *C12Q 2600/136* (2013.01); *G01N 2333/90293* (2013.01); *C12Q 1/6886* (2013.01); *C12Q 2600/106* (2013.01)
USPC ........................................... 435/455

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |

(Continued)

FOREIGN PATENT DOCUMENTS

| | | |
|---|---|---|
| CA | 2533701 A1 | 2/2005 |
| CA | 2587189 | 12/2006 |
| FR | 2877350 | 5/2006 |
| WO | 90/15156 | 12/1990 |
| WO | 91/00364 | 1/1991 |
| WO | 91/07424 | 5/1991 |
| WO | 93/12136 | 6/1993 |
| WO | 94/10343 | 5/1994 |
| WO | 94/24308 | 10/1994 |
| WO | 94/26930 | 11/1994 |

(Continued)

OTHER PUBLICATIONS

Kim et al. FHIT protein enhances paclitaxel-induced apoptosis in lung cancer cells. Int J Cancer. Apr. 1, 2006;118(7):1692-8, epub Oct. 2005.*

(Continued)

*Primary Examiner* — Michele K Joike
(74) *Attorney, Agent, or Firm* — MacMillan, Sobanski & Todd, LLC

(57) ABSTRACT

Provided herein are methods and compositions for the diagnosis, prognosis and treatment of a cancer associated disorder using the Fhit gene.

4 Claims, 37 Drawing Sheets
(4 of 37 Drawing Sheet(s) Filed in Color)

(56) References Cited

U.S. PATENT DOCUMENTS

| | | |
|---|---|---|
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,888,010 B2 | 2/2011 | Brown et al. |
| 7,919,245 B2 | 4/2011 | Brown et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 2000076524 | 12/2000 |
| WO | 01/44466 | 6/2001 |
| WO | 01/68666 | 9/2001 |
| WO | 01/77343 | 10/2001 |
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/013901 A3 | 2/2005 |
| WO | 2005/017711 | 2/2005 |
| WO | 2005013901 A3 | 2/2005 |
| WO | 2005/020795 | 3/2005 |
| WO | 2005060661 | 7/2005 |

(56) References Cited

FOREIGN PATENT DOCUMENTS

| WO | 2005/078139 | 8/2005 |
|---|---|---|
| WO | 2005/080601 | 9/2005 |
| WO | 2005079397 A2 | 9/2005 |
| WO | 2005/103298 A2 | 11/2005 |
| WO | 2005103298 A2 | 11/2005 |
| WO | 2005/118806 | 12/2005 |
| WO | 2006/105486 | 10/2006 |
| WO | 2006/108718 | 10/2006 |
| WO | 2006108718 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | 2007016548 A2 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007/112754 A2 | 10/2007 |
| WO | 2007112097 | 10/2007 |
| WO | 2007112754 A2 | 10/2007 |
| WO | 2007/127190 | 11/2007 |
| WO | 2008/008430 | 1/2008 |
| WO | 2008/036168 A2 | 3/2008 |
| WO | 2008/036776 | 3/2008 |
| WO | 2008/054828 | 5/2008 |
| WO | 2008/054828 C | 5/2008 |
| WO | 2008/070082 | 6/2008 |
| WO | 2008/073920 | 6/2008 |
| WO | 2008073915 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

Australian Government, Examiner's First Report, Appln. No. 2007243475, Dated Mar. 30, 2012.
Chinese Office Action, Application No. 20088011920639 dated May 3, 201.
Japanese Office Action dated Feb. 24, 2012, Japanese Patent Application No. 2008-54953.
Eiriksdottir, G. et al., "Mapping Loss of Heterozygosity at Chromosome 13q: Loss at 13q12-q13 is Associated wit Breast Tumour Progression and Poor Prognosis," European Journal of Cancer, 1998, pp. 2076-2081, vol. 34, No. 13.
Gailiun, M., "Single MicroRNA Causes Cancer in Transgenic Mice," Research Communications, The Ohio State University, Apr. 2006.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Blum, W. et al., "Clinical Response and miR-29b Predictive Significance in Older AML Patients Treated With a 10-Day Schedule of Decitabine," PNAS, Apr. 2010, vol. 107, No. 16, pp. 7473-7478.
Cui, S. et al., "MicroRNAs that Underlie Ovarian Cancer Development and Response to Chemotherapy," 98th AACR Annual Meeting, Apr. 14-18, 2007, Los Angeles, CA.
EP Search Report, Application No. 08799295.4-2402, PCT/US2008/075565, dated Sep. 11, 2010.
EP Search Report, Application No. 08841700.1-2405, PCT/US2008/081294, dated Jan. 4, 2011.
Esquela-Kerscher, A. et al., "Oncomirs—MicroRNAs with a Role in Cancer," Nature Reviews:Cancer, Apr. 2006, vol. 6, pp. 259-269.
Flavin. R.J. et al., "MicroRNA Gene Expression Profiling in Human Ovarian and Primary Paritoneal Serous Carcinomas," S. J. Mod. Pathol., Feb. 2007, vol. 20, p. 197A.
Garofalo, M. et al., "miR-221 & 222 Regulate TRAIL Resistance and Enhance Tumorigenicity through PTEN and TIMP2 Downregulation," Cancer Cell, Dec. 2009, vol. 16, pp. 498-509.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, vol. 108, Issue 11, p. 498.
Gourley, C. et al., "WWOX Gene Expression Abolishes Ovarian Cancer Tumorigenicity In Vivo and Decreases Attachment to Fibronectin via Integrin α3," Cancer Research, Jun. 2009, vol. 69, No. 11, pp. 4835-4842.
Ishii, H. et al., "Effect of Adenoviral Transduction of the Fragile Histidine Triad Gene into Esophageal Cancer Cells," Cancer Research, Feb. 2001, vol. 61, pp. 1578-1584.
Lujambio, A. et al., "A MicroRNA DNA Methylation Signature for Human Cancer Metastasis," PNAS, Sep. 2008, vol. 105, No. 36, pp. 13556-13561.
Maiseyeu, A. et al., "Gadolinum Containing Phosphatidylserine Liposomes for Molecular Imaging of Atherosclerosis," Journal of Lipid Research, Downloaded from www.jlr.org on Dec. 6, 2010, pp. 1-9.
Medina, P.P. et al., "OncomiR Addiction in an In Vivo Model of MicroRNA-21-Induced Pre-B-Cell Lymphoma," Nature Letters, Sep. 2010, vol. 467, pp. 86-91.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nicoloso, M.S. et al., "MicroRNAs—The Micro Steering Wheel of Tumour Metastases," Nature Reviews: Cancer, Apr. 2009, vol. 9, pp. 293-302.
Nurden, a.T., "Qualitative Disorders of Platelets and Megakaryocytes," Journal of Thrombosis and Haemostasis, 2005, vol. 3, pp. 1773-1782.
Pichiorri, F. et al., "MicroRNAs Regulate Critical Genes Associated with Multiple Myeloma Pathogenesis," PNAS, Sep. 2008, vol. 105, No. 35, pp. 12885-12890.
Pineau, P. et al., "miR-221 Overexpression Contributes to Liver Tumorigenesis," PNAS, Jan. 2010, vol. 107, No. 1, pp. 264-269.
Santanam, U. et al., "Chronic Lymphocytic Leukemia Modeled in Mouse by Targeted miR-29 Expression," PNAS, Jul. 2010, vol. 107, No. 27, pp. 12210-12215.
Schagen, F. et al., "Genetic Targeting of Adenovirus Vectors Using a Reovirus σ1-Based Attachment Protein," Molecular Therapy, May 2006, vol. 13, No. 5, pp. 997-1005.
Slack, F.J., "Big Roles for Small RNAs," Nature, Feb. 2010, vol. 463, p. 616.
Suarez-Saiz, F.J. et al., "MicroRNA Expression Profiling in Acute Myelogenous Leukemia," Canada Blood, Nov. 2004, Abstract #1131, p. 320A.
Uil, T.G. et al., "Generation of an Adenoviral Vector Containing an Addition of a Heterologous Ligand to the Serotype 3 Fiber Knob," Cancer Gene Therapy, 2003, vol. 10, pp. 121-124.
Valeri, N. et al., "Modulation of Mismatch Repair and Genomic Stability by miR-155," PNAS, Apr. 2010, vol. 107, No. 15, pp. 6982-6987.

(56) References Cited

OTHER PUBLICATIONS

Wijermans, P.W., "Low Dose Azanucleosidesfor High Risk (s) MDS and AML," Haematologica Reports,Nov. 2006, vol. 2, Issue, 15, pp. 74-76.
Zawacka-Pankau, J. et al., "Expression and Simple, One-Step Purification of Fragile Histidine Triad (Fhit) Tumore Suppressor Mutant Forms in *Escherichia coli* and their Interaction with Protoporphyrin IX," Biotechnol. Lett., 2007, vol. 29, pp. 877-883.
European Seach Report, Application No. 11151749.6, dated Feb. 8, 2011.
European Search Report, Application No. 11151769-4, dated Feb. 8, 2011.
European Search Report, Application No. 11151771-0, dated Feb. 8, 2011.
European Search Report, Application No. 11151772-8, dated Feb. 8, 2011.
European Search Report, Application No. 08713330.2, dated Jul. 22, 2011.
European Communication Pursuant to Article 94(3) EPC, Application No. 08768266.2, dated Apr. 18, 2011.
European Communication Pursuant to Article 94(3) EPC, Application No. 08767439.9, dated Mar. 15, 2011.
Chinese Office Action, Application No. 200780005821.2 dated Jan. 26, 2011.
PCT International Preliminary Report on Patentability, PCT/US2009/038214 filed Mar. 25, 2009, dated Jun. 16, 2011.
PCT International Preliminary Report on Patentability, PCT/US2009/065072 filed Nov. 19, 2009, dated Jun. 3, 2011.
Australian Office Action, Application No. 2006291165 dated Aug. 23, 2011.
European Search Report, Application No. 09713926.5 dated Jul. 21, 2011.
European Seach Report, Application No. 09714868.8 dated Aug. 1, 2011.
PCT International Preliminary Report on Patentability, PCT/US2010/025173 filed Feb. 24, 2010, dated Sep. 9, 2011.
Chinese Office Action, Application No. 200680039776.8 dated Jun. 30, 2011.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Cannistra, S.A., "Cancer of the Ovary," The New England Journal of Medicine, 2004, pp. 2519-2529, vol. 351, No. 25.
Chim, S.S.C. et al., "Detection and Characterization of Placental MicroRNAs in Maternal Plasma," Clinical Chemistry, 2008, pp. 482-490, vol. 54, No. 3.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Feng, G. et al., "Elevated Serum-Circulating RNA in Patients with Conventional Renal Cell Cancer," Anticancer Research, 2008, pp. 321-326, vol. 28.
He, L. et al., "A MicroRNA Polycistron as a Potential Human Oncogene," Nature, Jun. 2005, pp. 828-833, vol. 435.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jemal, A. et al., "Cancer Statistics, 2008," CA Cancer J. Clin., 2008, pp. 71-96, vol. 58, No. 2.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.

Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Mendell, J.T., "miRiad Roles for the miR-17-92 Cluster in Development and Disease," Cell, 2008, pp. 217-.
Meng, F. et al., "MicroRNA-21 Regulates Expression of the PTEN Tumor Suppressor Gene in Human Hepatocellular Cancer," Gastroenterology, 2007, pp. 647-658, vol. 133.
Nam, E.J. et al., "MicroRNA Expression Profiles in Serous Ovarian Carcinoma," Clinical Cancer Research, 2008, pp. 2690-2695, vol. 14, No. 9.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for "A Custon Microarray Platform for Analysis of MicroRNA Gene Expression," Nature Methods, Oct. 2004, pp. 47-53, vol. 1, No. 1.
Tilt, E. et al., "Expression and Function of Micro RNAs in Immune Cells During Normal or Disease State," International Journal of Medicine Sciences, 2008, pp. 73-79, vol. 5, No. 2.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Ambros, V. et al., "A Uniform System for MicroRNA Annotation," RNA, 2003, pp. 277-279, vol. 9.
Baira, E. et al., "Ultraconserved Elements: Genomics, Function and Disease," RNA Biology, Jul. 2008, pp. 132-134, vol. 5, No. 3.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Caldas, C. et al., "Sizing Up miRNAs as Cancer Genes," Nature Medicine, Jul. 2005, pp. 712-714, vol. 11, No. 7.
Canadian Intellectual Property Office, Requisition by the Examiner, Application No. 2,635,616, Dated Feb. 21, 2011.
Canadian Office Action, Application No. 2,617,581, dated Feb. 1, 2011.
Canadian Office Action, Application No. 2,621,441, dated Feb. 1, 2011.
Castoldi, M. et al., "A Sensitive Array for MicroRNA Expression Profiling (miChip) Based on Locked Nucleic Acids (LNA)," RNA, 2006, pp. 913-920, vol. 12.
Chinese Office Action, Application No. 200680036598.3 dated Feb. 24, 2011.
Chinese Office Action, Application No. 200780040146.7 dated May 25, 2011.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
EP Search Report, Application No. 08782609.5 dated Oct. 28, 2010.
Esquela-Kerscher, A. et al., "Oncomirs—MicroRNAs with a Role in Cancer," Nature Reviews:Cancer, Apr. 2006, pp. 259-269, vol. 6.
European Communication Pursuant to Article 94(3) EPC, Application No. 07810382.7, dated Dec. 8, 2010.
European Communication Pursuant to Article 94(3) EPC, Application No. 07867402.5, dated Jan. 5, 2011.

(56) References Cited

OTHER PUBLICATIONS

European Search Reoprt, Application No. 08841700.1, dated Jan. 4, 2011.
European Search Report, Application No. 08798444.9-2402, PCT/US2008/073964, dated Dec. 16, 2010.
European Search Report, Application No. 08799295.4-2402, PCT/US2008/075565, dated Nov. 9, 2010.
European Supplementary Search Report, Application No. 09715064.3 dated May 24, 2011.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Flavin, Rj et al., "MicroRNA Gene Expression Profiling in Human Ovarian and Primary Peritoneal Serous Carcinomas" USCAP 96th Annual Meeting, Abstract #897, San Diego, CA, Mar. 2007.
Ford, L.P., "A MicroRNA Expression Signature of Human Solid Tumors Defines Cancer Gene Targets," Leukemia Research, 2006, pp. 511-513, vol. 30.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.
He, X. et al., "MicroRNA and Esophageal Carcinoma," Journal of Nanjing Medical University, 2007, pp. 201-206, vol. 21, No. 4.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Kelly, L.M. et al., "CT53518, a Novel Selective FLT3 Antagonist for the Treatment of Acute Myelogenous Leukemia (AML)," Cancer Cell, Jun. 2002, pp. 421-432, vol. 1.
Kozomara, A. et al., "miRBase: Integrating MicroRNA Annotation and Deep-Sequencing Data," Nucleic Acids Research, 2011, pp. D152-D157, vol. 39.
Lagos-Quintana, M. et al., "Identification of Tissue-Specific MicroRNAs from Mouse," Current Biology, Apr. 2002, pp. 735-739, vol. 12.
Landgraf, P. et al., "A Mammalian MicroRNA Expression Atlas Based on Small RNA Library Sequencing," Cell, Jun. 2007, pp. 1401-1414, vol. 129.
Lanza, G. et al., "mRNA/microRNA Gene Expression Profile in Microsatellite Unstable Colorectal Cancer," Molecular Cancer, 2007, pp. 1-11, vol. 6, No. 54.
Li, S.-C. et al., "Bioinformatic Discovery of MicroRNA Precursors from Human ESTs and Introns," BMC Genomics, 2006, vol. 7.
Lujambio, a. et al., "A MicroRNA DNA Methylation Signature for Human Cancer Metastasis," PNAS, Sep. 2008, pp. 13556-13561, vol. 105, No. 36.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Nicoloso, M.S. et al., "MicroRNAs—The Micro Steering Wheel of Tumour Metastases," Nature Reviews: Cancer, Apr. 2009, pp. 293-302, vol. 9.
Pichiorri, F. et al., "MicroRNAs Regulate Critical Genes Associated with Multiple Myeloma Pathogenesis," PNAS, Sep. 2008, pp. 12885-12890, vol. 105, No. 35.

Pineau, P. et al., "miR-221 Overexpression Contributes to Liver Tumorigenesis," PNAS, Jan. 2010, pp. 264-269, vol. 107, No. 1.
Porkka, K.P. et al., "MicroRNA Expression Profiling in Prostate Cancer," Cancer Research, 2007, pp. 6130-6135, vol. 67, No. 13.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.
Saini, H. K. et al., "Annotation of Mammalian Primary MicroRNAs," BMC Genomics, 2008, vol. 9.
Santanam, U. et al., "Chronic Lymphocytic Leukemia Modeled in Mouse by Targeted miR-29 Expression," PNAS, Jul. 2010, pp. 12210-12215, vol. 107, No. 27.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schagen, F. et al., "Genetic Targeting of Adenovirus Vectors Using a Reovirus Sigma1-Based Attachment Protein," Molecular Therapy, May 2006, pp. 997-1005, vol. 13, No. 5.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Slack, F.J., "Big Roles for Small RNAs," Nature, Feb. 2010, p. 616, vol. 463.
Taccioli, C. et al., "Ucbase & miRfunc: A Database of Ultraconserved Sequences and MicroRNA Function," Nucleic Acids Research, 2009, pp. D41-D48, vol. 37.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Valeri, N. et al., "Modulation of Mismatch Repair and Genomic Stability by miR-155," PNAS, Apr. 2010, pp. 6982-6987, vol. 107, No. 15.
Wijermans, P.W., "Low Dose Azanucleosidesfor High Risk (s) MDS and AML," Haematologica Reports,Nov. 2006, pp. 74-76. vol. 2, Issue, 15.
Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX" Biotechnology Letters, Jun. 2007, pp. 877-883, vol. 29, No. 6.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bartel, D. P., "MicroRNAs: Target Recognition and Regulatory Functions," Cell, Jan. 2009, pp. 215-233, vol. 136.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.

(56) References Cited

OTHER PUBLICATIONS

Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.

Budhu, A. et al., "Identification of Metastasis-Related MicroRNAs in Hepatocellular Carcinoma," Hepatology, Mar. 2008, pp. 897-907, vol. 47, No. 3.

Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.

Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.

Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.

Calin, G. A. et al., "Human MicroRNA Genes are Frequently Located at Fragile Sites and Genomic Regions Involved in Cancers," PNAS, Mar. 2004, pp. 2999-3004, vol. 101, No. 9.

Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.

Calin, G. A. et al., "MicroRNA Signatures in Human Cancers," Nature Reviews Cancer, Nov. 2006, pp. 857-866, vol. 6.

Calin, G. A. et al., "MiR-15a and MiR-16-1 Cluster Functions in Human Leukemia," PNAS, Apr. 2008, pp. 5166-5171, vol. 105, No. 13.

Calin, G. A. et al., "Ultraconserved Regions Encoding ncRNAs are Altered in Human Leukemias and Carcinomas," Cancer Cell, Sep. 2007, pp. 215-229, vol. 12.

Chan, J. A. et al., "MicroRNA-21 is an Antiapoptotic Factor in Human Glioblastoma Cells," Cancer Research, Jul. 2005, pp. 6029-6033, vol. 65, No. 14.

Chang, N.-S. et al., "Molecular Mechanisms Underlying WOX1 Activation During Apoptotic and Stress Responses," Biochemical Pharmacology, 2003, pp. 1347-1354, vol. 66.

Chang, T.-C. et al., "Widespread MicroRNA Repression by Myc Contributes to Tumorigenesis," Nat Genet., Jan. 2008, pp. 43-50, vol. 40, No. 1.

Chen, C.-Z. et al., "MicroRNAs as Regulators of Mammalian Hematopoiesis," Seminars in Immunology, 2005, pp. 155-165, vol. 17.

Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.

Ciafre, S. A. et al., "Extensive Modulation of a Set of MicroRNAs in Primary Glioblastoma," Biochemical and Biophysical Research Communications, 2005, pp. 1351-1358, vol. 334.

Cimmino, A. et al., "miR-15 and miR-16 Induce Apoptosis by Targeting BCL2," PNAS, Sep. 2005, pp. 13944-13949, vol. 102, No. 39.

Cimmino, A. et al., Corrections to "miR-15 and miR-16 Induce Apoptosis by Targeting BCL2," PNAS, Feb. 2006, pp. 2464-2465, vol. 103, No. 7.

Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.

Croce, C. M. et al., "miRNAs, Cancer, and Stem Cell Division," Cell, 2005, pp. 6-7, vol. 36.

Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Dalmay, T. et al., "MicroRNAs and the Hallmarks of Cancer," Oncogene, 2006, pp. 6170-6175, vol. 25.

Davies, F. E. et al., "Insights into the Multistep Transformation of MGUS to Myeloma Using Microarray Expression Analysis," Blood, Dec. 2003, pp. 4504-4511, vol. 102, No. 13.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Eis, P. S. et al., "Accumulation of miR-155 and BIC RNA in Human B Cell Lymphomas," PNAS, Mar. 2005, pp. 3627-3632, vol. 102, No. 10.

European Patent Application, EP 1795203 A2, Croce et al., Application No. 06010581.4, filed Feb. 7, 1997, published Jun. 13, 2007.

European Search Report, Application No. 06800599.0 dated Oct. 19, 2009.

European Search Report, Application No. 06814375.9 dated Oct. 8, 2009.

European Search Report, Application No. 06825457.2 dated Sep. 16, 2009.

European Search Report, Application No. 07716208.9 dated Nov. 10, 2009.

European Search Report, Application No. 07717734.3 dated Nov. 9, 2009.

European Search Report, Application No. 07717903.4 dated Oct. 23, 2009.

European Search Report, Application No. 07753450.1 dated Jan. 12, 2009.

European Search Report, Application No. 07810382.7 dated Sep. 14. 2009.

European Search Report, Application No. 07867402.5 dated Mar. 16, 2010.

European Search Report, Application No. 07872618.9 dated Jul. 5, 2010.

European Search Report, Application No. 08767439.6 dated May 12, 2010.

European Search Report, Application No. 08768266.2 dated Jul. 1, 2010.

European Search Report, Application No. 08796821.0 dated Aug. 4, 2010.

European Search Report, Application No. 08841700.1 dated Jun. 2, 2010.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "MicroRNAs," The Cancer Journal, Jan./Feb. 2008, pp. 1-6, vol. 14, No. 1.

Fabbri, M. et al., "WWOX Gene Restoration Prevents Lung Cancer Growth In Vitro and In Vivo," PNAS, Oct. 2005, pp. 15611-15616, vol. 102, No. 43.

Fong, Y. et al., "Muir-Torre-Like Syndrome in FHIT-Deficient Mice," PNAS, Apr. 2000, pp. 4742-4747, vol. 97, No. 9.

Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.

Garzon, R. et al., "MicroRNA Fingerprints During Human Megakaryocytopoiesis," PNAS, Mar. 2006, pp. 5078-5083, vol. 103, No. 13.

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.

Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.

Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.

(56) References Cited

OTHER PUBLICATIONS

Griffiths-Jones, S. et al., "miRBase: MicroRNA Sequences, Targets and Gene Nomenclature," Nucleic Acids Research, 2006, pp. D140-D144, vol. 34.

Guimaraes-Sternberg, C. et al., "MicroRNA Modulation of Megakaryoblast Fate Involves Cholinergic Signaling," Leukemia Research, 2006, pp. 583-595, vol. 30.

Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.

Havelange, V. et al., "MicroRNAs: New Players in Acute Myeloid Leukemia," British Journal of Cancer, 2009, pp. 743-748, vol. 101.

Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.

Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.

Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.

Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.

Iorio, M. V. et al., "MicroRNA Gene Expression Deregulation in Human Breast Cancer," Cancer Research, Aug. 2005, pp. 7065-7070, vol. 65, No. 16.

Iorio, M. V. et al., "MicroRNA Signatures in Human Ovarian Cancer," Cancer Research, Sep. 2007, pp. 8699-8707, vol. 67, No. 18.

Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.

Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.

Ji, J. et al., "MicroRNA Expression, Survival, and Response to Interferon in Liver Cancer," The New England Journal of Medicine, Oct. 2009, pp. 1437-1447, vol. 361, No. 15.

Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.

Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.

Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.

Krek, A. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "New MicroRNAs From Mouse to Human," RNA, 2003, pp. 175-179, vol. 9, No. 2.

Landi, M. T. et al., "Gene Expression Signature of Cigarette Smoking and Its Role in Lung Adenocarcinoma Development and Survival," PLOS ONE, Feb. 2008, pp. 1-8, vol. 3, Issue 2.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Lin, R.-K. et al., "Alteration of DNA Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.

Lu, J. et al., "MicroRNA Expression Profiles Classify Human Cancers," Nature, Jun. 2005, pp. 834-838, vol. 435.

Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.

Mack, G. S., "MicroRNA Gets Down to Business," Nature Biotechnology, Jun. 2007, pp. 631-638, vol. 25, No. 6.

Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.

Marcucci, et al., "MicroRNA Expression in Cytogenetically Normal Acute Myeloid Leukemia," NEJM, May 2008, pp. 1919-1928, vol. 358, No. 18.

Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.

McManus, M. T., "MicroRNAs and Cancer," Seminars in Cancer Biology, 2003, pp. 253-258, vol. 13.

Megraw, M. et al., "miRGen: A Database for the Study of Animal MicroRNA Genomic Organization and Function," Nucleic Acids Research, 2007, pp. D149-D155, vol. 35.

(56) References Cited

OTHER PUBLICATIONS

Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Notice of Allowance and Fees Due in U.S. Appl. No. 12/160,064, filed Jul. 3, 2008, mailing date Nov. 20, 2009.
Notice of Allowance and Fees Due in U.S. Appl. No. No. 12/298,221, filed Nov. 10, 2008, mailing date Nov. 30, 2009.
Office Action issued in U.S. Appl. No. 12/083,067, filed Jun. 20, 2008, mailing date Jul. 8, 2010.
Office Action issued in U.S. Appl. No. 12/160,034, filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.

(56) References Cited

OTHER PUBLICATIONS

PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPllb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tang, X. et al., "A Simple Array Platform for MicroRNA Analysis and Its Application in Mouse Tissues," RNA, Aug. 2007, pp. 1-20, vol. 13.
Thomson, J. M. et al., "A Custom Microarray Platform for Analysis of MicroRNA Gene Expression," Nature Methods, Oct. 2004, pp. 1-7, vol. 1, No. 1.
Thorgeirsson, S. S. et al., "Functional Genomics of Hepatocellular Carcinoma," Hepatology, Feb. 2006, pp. S145-S150, vol. 43, No. 2, Suppl. 1.
Tockman, M. S. et al., "Considerations in Bringing a Cancer Biomarker to Clinical Application," Cancer Research, May 1992, pp. 2711s-2718s, vol. 52.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.
Valeri, N. et al., "Epigenetics, miRNAs, and Human Cancer: A New Chapter in Human Gene Regulation," Mamm Genome, Aug. 2009, pp. 573-580, vol. 20.
Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.
Virgilio, L. et al., "Identification of the TCL1 Gene Involved in T-Call Malignancies," Proc. Natl. Acad. Sci., Dec. 1994, pp. 12530-12534, vol. 91.
Visone, R. et al., "MiRNAs and Cancer," The American Journal of Pathology, Apr. 2009, pp. 1131-1138, vol. 174, No. 4.
Volinia, et al., "Reprogramming of MirRNA Networks in Cancer and Leukemia," Genome Research, 2010, pp. 589-599, vol. 20.
Volinia, S. et al., "A MicroRNA Expression Signature of Human Solid Tumors Defines Cancer Gene Targets," PNAS, Feb. 2006, pp. 2257-2261, vol. 103, No. 7.
Wang, E. et al., "Ontogeny and Oncogenesis Balance the Transcriptional Profile of Renal Cell Cancer," Cancer Research, Oct. 2004, pp. 7279-7287, vol. 64.

(56) References Cited

OTHER PUBLICATIONS

Wang, X. et al., "Association Between CpG Island Methylation of the WWOX Gene and Its Expression in Breast Cancers," Tumor Biology, Feb. 2009, pp. 8-14, vol. 30.
Weidhaas, J., "Using MicroRNAs to Understand Cancer Biology," Published Online Dec. 21, 2009, DOI: 10.1016/S1470-2045(09)70386-9.
Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.
Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.
Yanaihara, N. et al., "Unique MicroRNA Molecular Profiles in Lung Cancer Diagnosis and Prognosis," Cancer Cell, Mar. 2006, pp. 189-198, vol. 9.
Yang, J. et al., "Analysis of Sequence Variations in 59 MicroRNAs in Hepatocellular Carcinomas," Mutation Research, Aug. 2008, pp. 205-209, vol. 638.
Yendamuri, S. et al., "WW Domain Containing Oxidoreductase Gene Expression is Altered in Non-Small Cell Lung Cancer," Cancer Research, Feb. 2003, pp. 878-881, vol. 63.
Yoon, S. et al., "Prediction of Regulatory Modules Comprising MicroRNAs and Target Genes," Bioinformatics Genes and Genomes, 2005. Pages ii93-ii100, vol. 21, Suppl. 2.
Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.
Zeng, Y. et al., "Recognition and Cleavage of Primary MicroRNA Precursors by the Nuclear Processing Enzyme Drosha," The EMBO Journal, 2005, pp. 138-148, vol. 24.
Zhang, L. et al., "Genomic and Epigenetic Alterations Deregulate MicroRNA Expression in Human Epithelial Ovarian Cancer," PNAS, May 2008, pp. 7004-7009, vol. 105, No. 19.
Zhang, L. et al., "MicroRNAs Exhibit High Frequency Genomic Alterations in Human Cancer," PNAS, Jun. 2006, pp. 9136-9141, vol. 103, No. 24.
Zhang, L. et al., Supporting Information, PNAS 2008, pp. 1-11.
Zhang, Z. et al., "Three Biomarkers Identified from Serum Proteomic Analysis for the Detection of Early Stage Ovarian Cancer," Cancer Research, Aug. 2004, pp. 5882-5890, vol. 64.
Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.
EP Search Report, Application No. 12165636.7 dated Jun. 8, 2012.
EP Search Report, Application No. 12165638.3 dated Jun. 12, 2012.
Australian Office Action, Application No. 2007227423 dated Apr. 13, 2012.
Australian Office Action, Application No. 2007205257 dated Dec. 22, 2011.
Australian Office Action, Application No. 2007205234 dated Sep. 20, 2011.
Australian Office Action, Application No. 2006291165 dated Feb. 13, 2012.
Canadian Office Action, Application No. 2,617,581, dated Apr. 2, 2012.
Canadian Office Action, Application No. 2,635,616, dated Feb. 27, 2012.
Chinese Office Action, Application No. 200780033066.9 dated Jun. 26, 2012.
Chinese Office Action, Application No. 200880112585.9 dated May 24, 2012.
Chinese Office Action, Application No. 20088011920639 dated May 3, 2012.
Communication Concerning Office Action Received from Japanese Patent Office dated Jan. 30, 2012, Japanese Patent Application No. 2008-531200.
EP Search Report, Application No. 11196190.0 dated Apr. 24, 2012.
EP Search Report, Application No. 11196253.6 dated Apr. 24, 2012.
EP Search Report, Application No. 11196264-3 dated Feb. 28, 2012.
EP Search Report, Application No. 11196250.2 dated Apr. 24, 2012.
EP Search Report, Application No. 12154298.9 dated Jun. 4, 2012.
EP Search Report, Application No. 11196256.9 dated Feb. 28, 2012.
EP Search Report, Application No. 11196254.4 dated Feb. 28, 2012.
EP Search Report, Application No. 11196265.0 dated Mar. 5, 2012.
EP Search Report, Application No. 11196262.7 dated Feb. 28, 2012.
EP Search Report, Application No. 11196261.9 dated Feb. 28, 2012.
European Communication Pursuant to Article 94(3) EPC, Application No. 08841700.1, dated Jun. 1, 2012.
European Communication Pursuant to Article 94(3) EPC, Application No. 07716208.9, dated Sep. 13, 2011.
European Communication Pursuant to Article 94(3) EPC, Application No. 07717903.4, dated Apr. 25, 2012.
European Communication Pursuant to Article 94(3) EPC, Application No. 07867402.5, dated Apr. 10, 2012.
European Communication Pursuant to Article 94(3)EPC, Application No. 06814375.9 dated Oct. 14, 2011.
European Communication Pursuant to Article 94(3) EPC, Application No. 06800599.0 dated Nov. 25, 2011.
European Communication Pursuant to Article 94(3) EPC, Application No. 08799295.4, dated Nov. 18, 2011.
European Communication Pursuant to Article 94(3) EPC, Application No. 08767439.6, dated Feb. 12, 2011.
European Search Report, Application No. 08770974.4, dated Oct. 21, 2011.
Japanese Office Action dated Feb. 24, 2012, Japanese Patent Application No. 2008-549555.
Japanese Office Action dated Jan. 4, 2012, Japanese Patent Application No. 2008-5251070.
Japanese Office Action dated Feb. 24, 2012, Japanese Patent Application No. 2008-549532.
Japanese Office Action dated Feb. 22, 2012, Japanese Patent Application No. 2008-549549.
PCT International Preliminary Report on Patentability, PCT/US2010/057758 filed Nov. 23, 2010, dated Jun. 7, 2012.
PCT International Search Report and the Written Opinion, PCT/US2012/020911 filed Jan. 11, 2012, dated Apr. 25, 2012.
PCT Invitation to Pay Additional Fees, PCT/US2012/028016 filed Mar. 7, 2012, dated May 29, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Braun et al., "p53-Responsive MicroRNAs 192 and 215 are Capable of Inducing Cell Cycle Arrest," Cancer Research, 2008, pp. 10094-10104, vol. 68.
Eiriksdottir, G. et al., "Mapping Loss of Heterozygosity at Chromosome 13q: Loss at 13q12-q13 is Associated with Breast Tumour Progression and Poor Prognosis," European Journal of Cancer, 1998, pp. 2076-2081, vol. 34, No. 13.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gailiun, M., "Single MicroRNA Causes Cancer in Transgenic Mice," Research Communications, The Ohio State University, Apr. 2006, pp. 1-3.
Gang, M. et al., "Expression of Programmed Cell Death 4 and Its Clinicopathological Significance in Human Pancreatic Cancer," Abstract, 2005, pp. 597-600, vol. 27.
Garofalo, M. et al., "MicroRNA Signatures of TRAIL Resistance in Human Non-Small Cell Lung Cancer," Oncogene, 2007, pp. 3854-3855, vol. 27.
Jazbutyte, V. et al., "MicroNRA-21: From Cancer to Cardiovascular Disease," Current Drug Targets, Abstract, 2010, pp. 926-935, vol. 11.
Kim, et al., FHIT Protein Enhances Paclitaxel-Induced Apoptosis, Int. J. Cancer, vol. 118, pp. 1692-1698.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.

(56) References Cited

OTHER PUBLICATIONS

Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.

Okada, H. et al., "MicroRNAs in Immune Regulation—Opportunities for Cancer Immunotherapy," The International Journal of Biochemistry & Cell Biology, 2010, pp. 1256-1261, vol. 42.

Petrocca, F. et al., "MicroRNAs Deregulation in Gastric Cancer," PNAS, Apr. 2006, p. 1338, vol. 47, Abstract # 5690.

Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.

Ribas, J. et al., "The Transcriptional Regulation of miR-21, Its Multiple Transcripts, and Their Implication in Prostate Cancer," Cell Cycle, 2010, pp. 923-929, vol. 9.

Rossi, S, et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.

Ryu, J.K. et al., "Aberrant MicroRNA-155 Expression is an Early Event in the Multistep Progression of Pancreatic Adenocarcinoma," Pancreatology, 2010, pp. 66-73, vol. 10.

Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.

Vassilev et al., "In Vivo Activation of the p53 Pathway by Small-Molecule Antagonists of MDM2," Science, 2004, pp. 844-848, vol. 303.

Watson, D.I. et al., "MicroRNA Expression Profiles in Barrett's Oesophagus," RACS Annual Scientific Congress, 2007, pp. A45, vol. 77.

Wiemer et al., "The Role of MicroRNAs in Cancer: No Small Matter," European Journal of Cancer, Jun. 12, 2007, vol. 43, No. 10, pp. 1529-1544.

Xi, Y. et al., "Prognostic Values of MicroRNAs in Colorectal Cancer," Biomarker Insights, Jan. 2006, pp. 113-121, vol. 1.

Zhao et al., "p53 Mediates the Negative Regulation of MDM2 by Orphan Receptor TR3," The EMBO Journal, 2006, pp. 5703-5715, vol. 25.

* cited by examiner

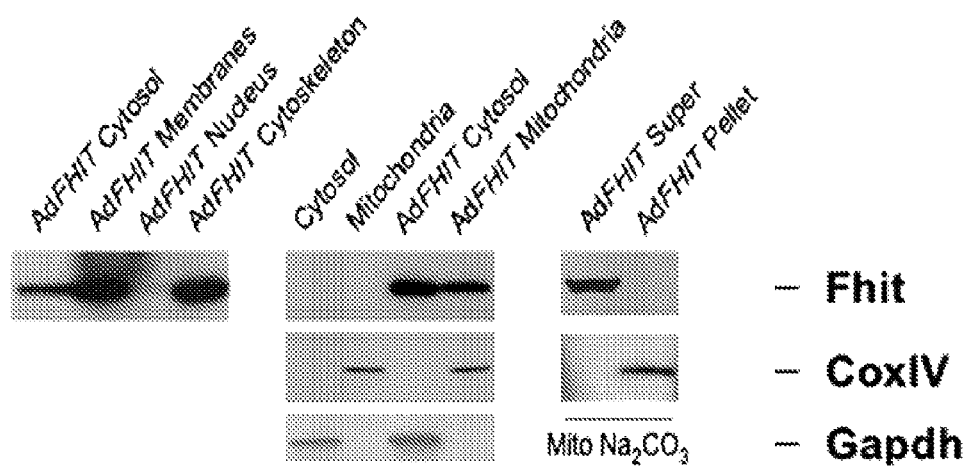
Figure 1C  Figure 1D  Figure 1E
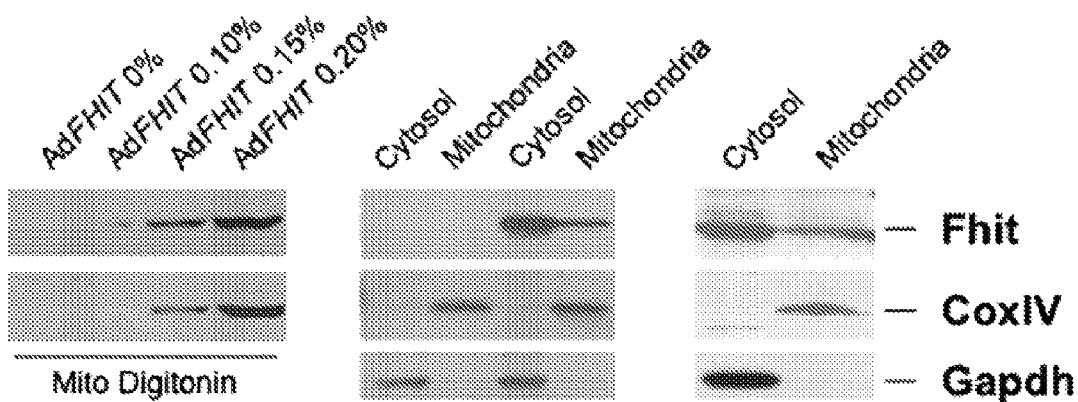
Figure 1F  Figure 1G  Figure 1H

| Protein | Accession no. | Molecular mass kDa | Function/ category | Subcellular localization | No. identified peptides | Peptide sequences | SEQ ID NO: | Protein Mascot score | Sequence coverage |
|---|---|---|---|---|---|---|---|---|---|
| Hsp60 | NP_002147 | 60 | 60-kDa Heat shock protein | Cytosol/ mitochondria | 6 | VGEVIVTK | 1 | 239 | 10% |
| | | | | | | LSDGVAVLK | 2 | | |
| | | | | | | IGIEIIKR | 3 | | |
| | | | | | | VTDALNATR | 4 | | |
| | | | | | | TVIIEQSWGSPK | 5 | | |
| | | | | | | VGGTSDVEVNEKK | 6 | | |
| Malate dehydro-genase (Mdh) | NP_005909 | 33 | Catalyzes the reversible oxidation of malate to oxaloacetate | Mitochondrial matrix | 8 | ANTFVAELK | 7 | 193 | 28% |
| | | | | | | IQEAGTEVVK | 8 | | |
| | | | | | | VNVPVIGGHAGK | 9 | | |
| | | | | | | IFGVTTLDIVR | 10 | | |
| | | | | | | FVFSLVDAMNGK | 11 | | |
| | | | | | | GCDVVVIPAGVPR | 12 | | |
| | | | | | | AGAGSATLSMAYAGAR | 13 | | |
| | | | | | | GYLGPEQLPDCLK | 14 | | |
| Electron transfer flavor protein (Etfb) | NP_001976 | 28 | Specific electron acceptor for mitochondrial dehydro-genases | Mitochondrial matrix | 3 | EIDGGLETLR | 15 | 96 | 12% |
| | | | | | | VETTEDLVAK | 16 | | |
| | | | | | | LSVISVEDPPQR | 17 | | |
| Hsp10 | AAC 96332 | 10 | 10-kDa Heat shock protein | Cytosol/mitochondria | 3 | GGEIQPVSVK | 18 | 92 | 34% |
| | | | | | | VLQATVVAVGSGSK | 19 | | |
| | | | | | | VVLDDKDYFLFR | 20 | | |
| Mitochon-drial aldehyde dehydro-genase 2 (Adh2) | NP_000681 | 55 | Second enzyme of the major oxidative pathway of alcohol metabolism | Mitochondrial matrix | 2 | LADLIER | 21 | 75 | 4% |
| | | | | | | LGPALATGNVVVMK | 22 | | |
| Ferre-doxin reductase (Fdxr) | P22570 | 54 | First electron transfer protein in all the mitochondrial p450 systems | Mitochondrial matrix | 1 | FGVAPDHPEVK | 23 | 47 | 2% |

Figure 7 - TABLE 1

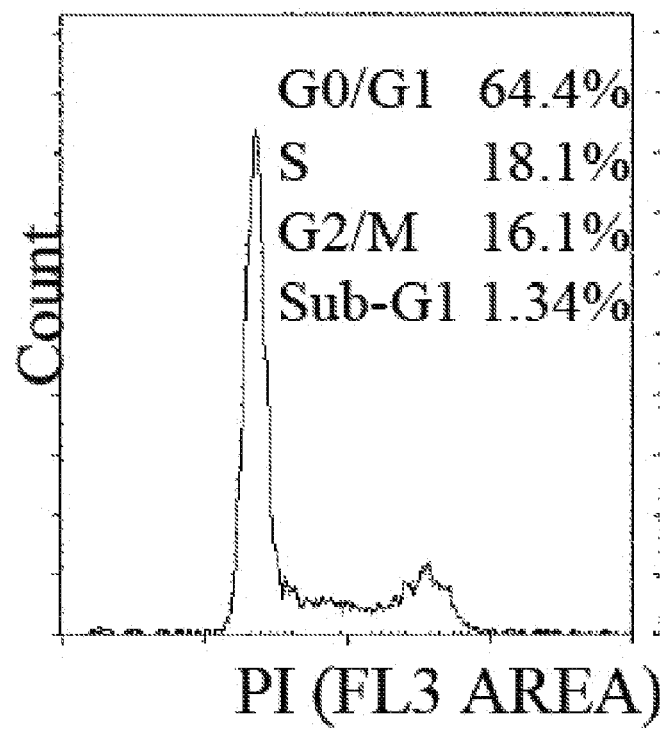
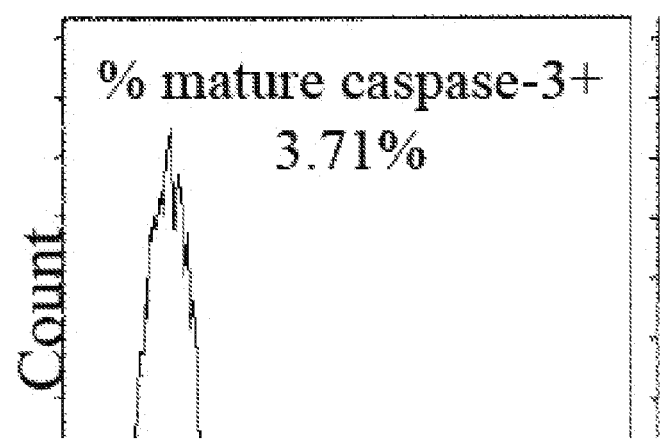
Figure 8B

**Ad*GFP***
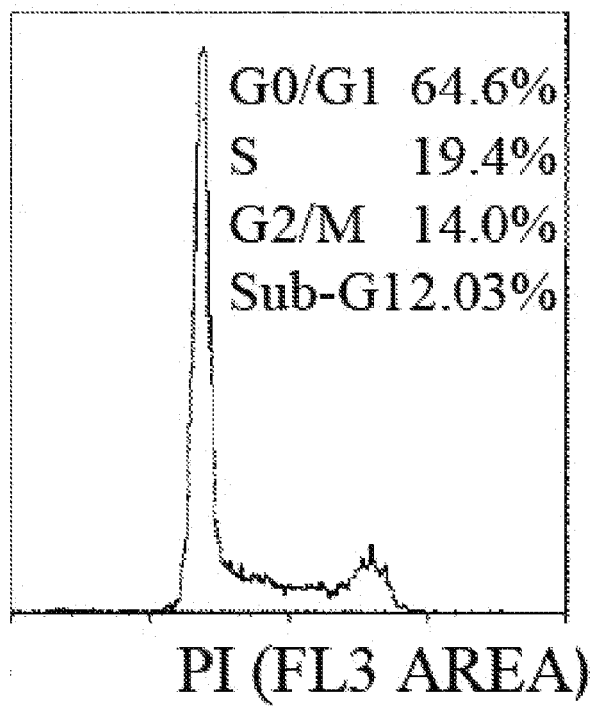
PI (FL3 AREA)
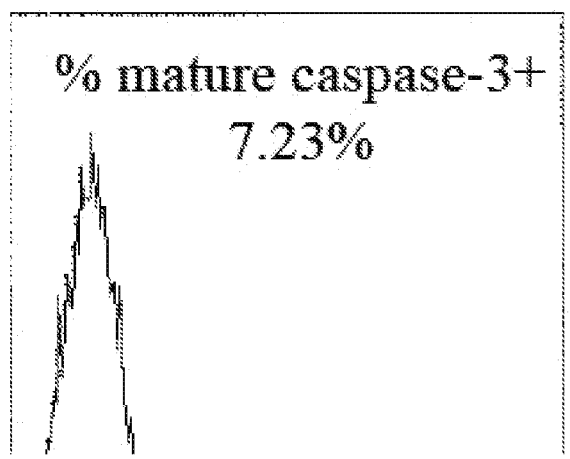
Figure 8B cont.

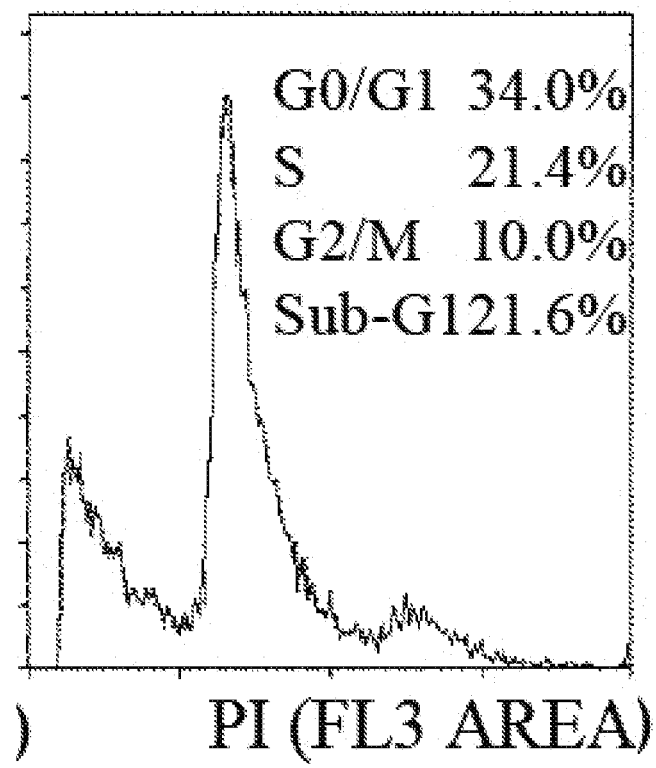
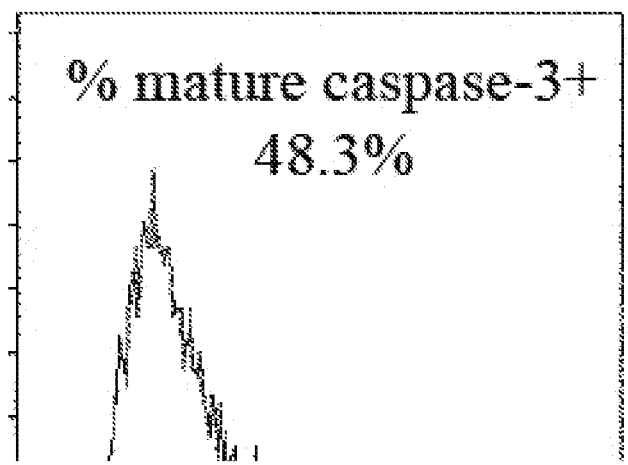
Figure 8B cont

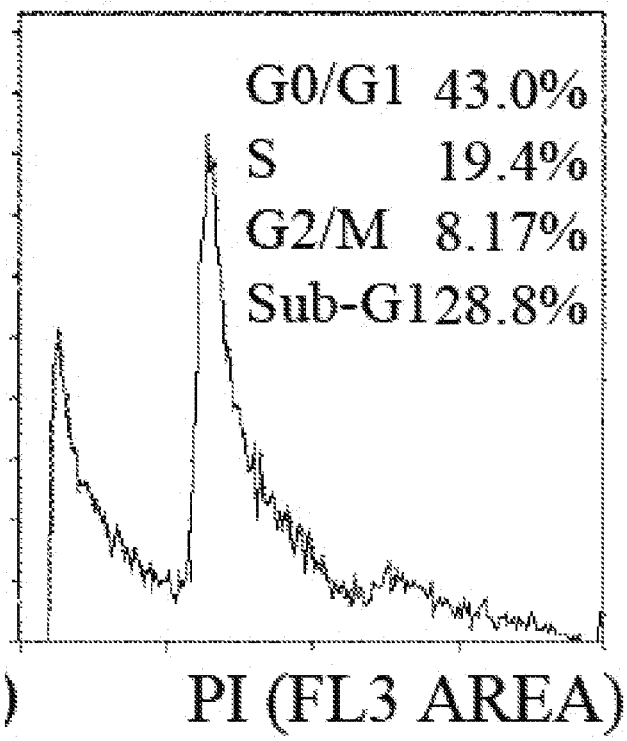
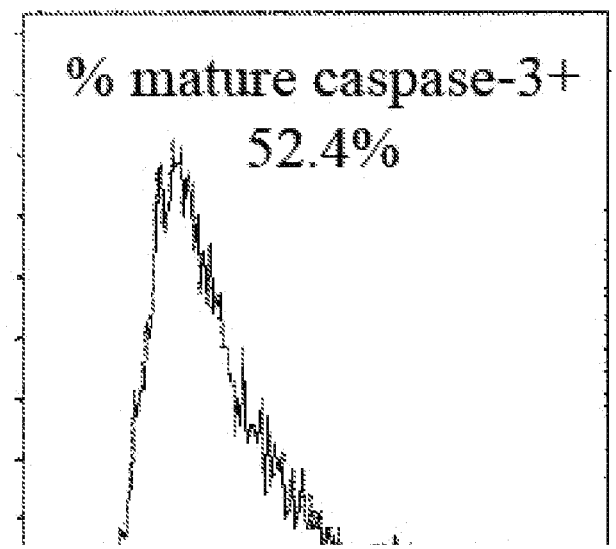
Figure 8B cont.

Hsp60

|  | MKN74E4 (Fhit-) | MKN74A116 (Fhit+) |
|---|---|---|
| $H_2O_2$ (mM) | ROS-positive cells (%) | ROS-positive cells (%) |
| - | 1.0 | 2.4 |
| 0.5 | 1.3 ± 0.3 | 19.5 ± 1.7 |
| 1.0 | 14.1 ± 1.4 | 30.3 ± 2.9 |
| 2.0 | 19.3 ± 2.3 | 85.6 ± 4.3 |

Figure 10 - TABLE 2

SEQUENCE LISTING

<160> NUMBER OF SEQ ID NOS: 33

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Val Gly Glu Val Ile Val Thr Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Ser Asp Gly Val Ala Val Leu Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Gly Ile Glu Ile Ile Lys Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Thr Asp Ala Leu Asn Ala Thr Arg
1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Val Ile Ile Glu Gln Ser Trp Gly Ser Pro Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Gly Gly Thr Ser Asp Val Glu Val Asn Glu Lys Lys
1               5                   10
```

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Asn Thr Phe Val Ala Glu Leu Lys
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Gln Glu Ala Gly Thr Glu Val Val Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Asn Val Pro Val Ile Gly Gly His Ala Gly Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Phe Gly Val Thr Thr Leu Asp Ile Val Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Val Phe Ser Leu Val Asp Ala Met Asn Gly Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Gly Cys Asp Val Val Ile Pro Ala Gly Val Pro Arg
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gly Ala Gly Ser Ala Thr Leu Ser Met Ala Tyr Ala Gly Ala Arg
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Tyr Leu Gly Pro Glu Gln Leu Pro Asp Cys Leu Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ile Asp Gly Gly Leu Glu Thr Leu Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Glu Thr Thr Glu Asp Leu Val Ala Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Ser Val Ile Ser Val Glu Asp Pro Pro Gln Arg
1               5                   10
```

-continued

```
<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Glu Ile Gln Pro Val Ser Val Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Leu Gln Ala Thr Val Val Ala Val Gly Ser Gly Ser Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Val Leu Asp Asp Lys Asp Tyr Phe Leu Phe Arg
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Ala Asp Leu Ile Glu Arg
1               5

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gly Pro Ala Leu Ala Thr Gly Asn Val Val Val Met Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Phe Gly Val Ala Pro Asp His Pro Glu Val Lys
1               5                   10

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtttcccgtg cgaacccagc t                                          21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctacgacgcg gaggacccgg tg                                         22

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acgtggatcc ctgtgaggac atgtcgttca gatttggc                        38

<210> SEQ ID NO 27
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttgtggatcc ttatcagtga tggtgatggt gatgcgatcc tctctgaaag tagacccgca  60
g                                                                 61

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctgttcccag ccatggcttc gcgctg                                     26

<210> SEQ ID NO 29
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
tcagtggccc aggaggcgca gcatc                                           25

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgttcccag ccatggcttc gcgctg                                          26

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtggcccagg aggcgcagca tc                                              22

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 33

His His His His His
1               5
```

METHODS FOR IDENTIFYING FRAGILE HISTIDINE TRIAD (FHIT) INTERACTION AND USES THEREOF

CROSS-REFERENCE TO RELATED APPLICATIONS AND STATEMENT REGARDING SPONSORED RESEARCH

The present invention claims the benefit of PCT application No. PCT/US/2008/081294 filed Oct. 27, 2008 which claims priority to the provisional patent application Ser. No. 60/000,480 filed Oct. 26, 2007.

This invention was made with government support under NCI Grant Nos. CA77738 and CA78890. The government has certain rights in this invention.

BACKGROUND OF THE INVENTION

The FHIT gene encompasses the most active common fragile site at chromosome 3p14.2 (1, 2). Fhit expression is lost or reduced in a large fraction of most types of human tumors due to allelic loss, genomic rearrangement, promoter hypermethylation, or combinations thereof (3, 4). Fhit knock-out mice show increased susceptibility to cancer development (5, 6) and FHIT gene therapy prevents tumors in carcinogen-exposed Fhit-deficient mice (7, 8). Fhit restoration by stable transfection in cancer cells has little effect in vitro, unless cells are exposed to stress, including the stress of the nude mouse environment in vivo (9); viral-mediated Fhit restoration, a process that simultaneously supplies stress and Fhit expression, suppresses tumorigenesis in vivo and triggers apoptosis of many types of malignant cells in vitro (10-13), including lung cancer cells.

In lung hyperplastic lesions, DNA damage checkpoint genes are already activated, leading to selection for mutations in checkpoint proteins and neoplastic progression (14, 15). Evidence of DNA alteration at FRA3B within FHIT accompanied the hyperplasia and checkpoint activation. Loss of FHIT alleles occurs in normal appearing bronchial epithelial cells of smokers, prior to pathologic changes or alterations in expression of other suppressor genes (16-18).

Fhit expression is down-regulated by exposure to DNA damaging agents (19) and Fhit plays a role in response to such agents (20, 21), with Fhit-deficient cells escaping apoptosis and accumulating mutations.

Although Fhit expression triggers apoptosis in several experimental models through caspase-dependent mechanisms involving extrinsic and intrinsic apoptotic pathways, little is known about early events in this process and how Fhit loss is involved in tumor initiation.

Therefore, there is a need for methods for altering the expression of FHIT in subjects in need thereof. There is also a need for compositions that are useful to alter the expression of FHIT in subjects in need thereof.

SUMMARY OF THE INVENTION

In a broad aspect, there is provided methods which identify proteins that interact directly with Fhit to effect downstream signal pathways culminating in apoptosis. In one embodiment, proteins within cells were chemically cross-linked after infection of lung cancer cells with AdFHIT-His6 virus. The proteins linked to Fhit and pathways affected by them were identified and characterized.

In another broad aspect, there is provided herein a method of diagnosing whether a subject has, or is at risk for developing, a cancer associated disorder, comprising measuring the level of at least fragile histidine triad (Fhit) gene in a test sample from the subject, wherein an alteration in the level of the Fhit gene product in the test sample, relative to the level of a corresponding Fhit gene product in a control sample, is indicative of the subject either having, or being at risk for developing, a cancer associated disorder.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1H—Subcellular localization of Fhit protein in cytosol and mitochondria.

FIG. 1A, immunofluorescence microscopy was performed with anti-Fhit serum on H1299 cells (D1) treated with PonA for 48 h; Fhit staining was detected using fluorescein isothiocyanate (green)-conjugated anti-rabbit immunoglobulin (IgG); Mito-Tracker Red staining, which identifies mitochondria, shows partial colocalization with Fhit. The yellow color on the fourth panel (lower right) shows the co-localizations points.

FIG. 1B, immunoelectron microscopy of A549 AdFHIT (left) or AdFHIT-$His_6$-infected cells (right) performed with a penta-His antibody shows Fhit mitochondrial localization (right); A549 cells infected with AdFHIT served as control and show only a few scattered grains (left panel).

FIG. 1C, immunoblot analysis of AdFHIT-infected A549 subcellular fractions using anti-Fhit indicates Fhit protein distribution in the cytosol, membranes, cytoskeleton, and mitochondria.

FIG. 1D, immunoblot analysis of proteins from mitochondria of A549 cells infected with AdFHIT-$His_6$ after treatment with sodium carbonate (FIG. 1E) and increasing concentrations of digitonin (FIG. 1F) indicates that Fhit is mainly distributed in mitochondrial matrix; filters were probed with Fhit and CoxIV antisera; lanes in FIG. 1F represent supernatants after treatment with 0, 0.10, 0.15, and 0.20% digitonin.

FIG. 1G, immunoblot analyses of subcellular fractions from MKN74/E4 and MKN74/A116 cells (stably expressing exogenous Fhit), and FIG. 1H, HCT116 (an endogenous Fhit-positive colon cancer cell line) using anti-Fhit, confirms Fhit mitochondrial localization; GAPDH and CoxIV antisera served as controls.

FIG. 2D, coimmunoprecipitation with anti-Hsp60 after infection of A549 cells with AdFHIT; filters were probed with Hsp60, Fhit, and Hsp10 antisera.

FIG. 2E, A549 cells were co-transfected with the V5-tagged FDXR gene and FHIT plasmids; immunoprecipitation was with anti-V5 and detection with Fdxr and Fhit antisera.

FIG. 2F, immunoprecipitation and immunoblot detection of endogenous interactor proteins (Fdxr and Hsp10) from DSP-treated Fhit-positive HCT116 cells. Filters were probed with antisera against each target protein. Endogenous Fhit co-precipitated with Hsp10 and Fdxr.

FIG. 3A, nickel-H6 pull down experiment of A549 cells AdFHIT-$His_6$ infected on subcellular fractions (Cytosol and Mitochondria) using H6 antibody; lysates were incubated with nickel beads to isolate the DSP cross-linked Fhit-His$_6$ protein complex and loaded on a 4-20% polyacrylamide gel. 24 h after infection, the Hsp60-Fhit complex was present in both compartments; 48 h after infection, the complex was detectable again in both compartments and the increase of Fhit complex proteins appears related to the increase of Fhit protein at 48 h after AdFHIT-His$_6$ infection, with a slight increase in the mitochondria (densitometry analysis on input samples was performed).

FIG. 3B, immunoblot analysis of Hsp60, Hsp10, Fhit, and GAPDH in Fhit-positive D1 cells after 72 h of Hsp60/Hsp10 silencing showing Fhit, Hsp60, and Hsp10 levels after a CHX chase (30 μg/ml) for 1-12 h.

FIG. 3C, immunoblot analysis of cytosol/mitochondrial protein fractions of A549 cells 72 h after transfection with Hsp60 and Hsp10 siRNAs and 24 h after AdFHIT infection at m.o.i. 1, with Hsp60, Hsp10, Fhit, GAPDH, and CoxIV antisera. Hsp60/10 silencing does not appear to affect the Fhit cytosolic level, but is associated with a decrease of Fhit in the mitochondrial fraction. Scrambled (Scr) siRNAs were used as controls.

FIG. 3D, subcellular fractionation and immunoprecipitation of "endogenous" Fhit complex proteins. PonA-induced D1 and E1 cells, with and without peroxide treatment, were fractionated into cytosol and mitochondria and subcellular fractions assessed for the presence of Fhit and interactors (left side) at 48 h after induction; 25 μg of proteins were loaded per lane. Endogenous Hsp60 co-precipitated Fhit and Fdxr.

FIG. 4A, fluorescence-activated cell sorter (FACS) analysis for ROS assessment in A549 cells 48 h after transfection with FHIT plasmid, with and without a 5-h $H_2O_2$ treatment. Empty vector-transfected cells served as control. Intracellular superoxide was determined according to the fluorescence of ethidium as a result of oxidation of hydroethidine by $O_2$. M2 refers to the fraction of ROS positive cells.

FIG. 4B, FACS analysis for ROS assessment by the fluorescence produced from the oxidation of hydroethidine in D1 and E1 cells; 48 h after PonA treatment, cells were treated for 5 h with 0.5 and 1.0 mM $H_2O_2$ and oxidative stress was measured; % positive refers to the fraction of fluorescent cells, indicating ROS. These experiments were repeated three times with similar results.

FIG. 4C, increased green fluorescent DCF signal in H1299 Fhit-expressing cells (D1) under stress conditions. Cells were incubated with 2′,7′-dichlorodihydrofluorescein diacetate, a ROS indicator that can be oxidized in the presence of ROS to the highly green fluorescent dye DCF, at 48 h after Fhit induction and after a 5-h $H_2O_2$ treatment of E1 and D1 cells (magnification ×40).

FIG. 4D, MTS cell viability assays were performed on E1 and D1 cells. Cells were treated with PonA for 48 h and then with increasing concentrations of $H_2O_2$ (0.125, 0.25, and 0.5 mM) for 4 h. Analysis was at 24 h after $H_2O_2$ treatment. Columns report the average of four experiments ±S.E. Each point was measured in quadruplicate and standard deviation calculated; p<0.05 was considered significant.

FIG. 4E, FACS analysis of D1 and E1 cell cycle kinetics at 48 h after oxidative stress treatment. Cells were treated with PonA for 48 h and then with increasing concentrations of $H_2O_2$ (0.25 and 0.5 mM) for 4 h. Analysis was at 48 h after $H_2O_2$ treatment. All experiments were performed twice in triplicate.

FIG. 4F, colony formation assay of H1299/D1 and H1299/E1 cells after 5 mM PonA stimulation and a 5-h $H_2O_2$ treatment at the indicated concentrations.

FIG. 5A, immunoblot analysis with antisera against Fdxr, Fhit, and GAPDH. Proteins were extracted from E1 (control) and D1 cells 48 h after treatment with PonA.

FIG. 5B, immunoblot analysis of Fdxr expression in D1 and E1 cells after a 4-h treatment with 25 μA MG132, a proteasome inhibitor. GAPDH detection shows equal protein loading.

FIG. 5C, immunoblot analysis of Fdxr, Fhit, and GAPDH in D1, expressing Fhit, and E1 cells, showing Fdxr level after CHX chase (30 μg/ml) for 4-12 h. Densitometry based on GAPDH levels shows enhanced stability of Fdxr in the presence of Fhit.

FIG. 5D, FACS analysis of FDXR$^{+/+/+}$ and FDXR$^{+/-/-}$ cell cycle kinetics after infection with AdFHIT m.o.i. 50 and 100. The experiment was performed 48 h after infection and was repeated three times with similar results. Profiles of AdGFP-infected cells were similar to those of non-infected cells (not shown).

FIG. 5E, immunoblot analysis showing expression of Fdxr, Fhit, and GAPDH after infection of FDXR$^{+/+/+}$ and FDXR$^{+/-/-}$ with AdFHIT m.o.i. 50 and 100. Proteins were extracted 48 h after infection.

FIG. 5F, real-time RT-PCR analysis for FDXR expression at 48 h after AdFHIT m.o.i. 50. The PCR product was normalized to GADPH and Actin expression and each point was repeated in quadruplicate; differences between control and Fhit positive samples were not significant.

FIG. 5G, caspase 3 and Parp1 activation. Immunoblot analysis, using Fhit, caspase 3, Parp1 antisera, of total cell lysates from HCT116 FDXR cells 48, 72, and 96 h after infection with AdFHIT and AdGFP at m.o.i. 50. GAPDH and CoxIV served as internal protein markers.

FIG. 5H, immunoblot analysis, using Fhit and cytochrome c antisera, of cytosol/mitochondria fractions from HCT116 FDXR cells 48, 72, and 96 h after infection with AdFHIT and AdGFP at m.o.i. 50. GAPDH and β-actin served as internal protein markers.

MTS assays performed on E1 and D1 cells. Cells were treated with PonA for 48 h and then treated with paclitaxel (50-500 ng/ml) (FIG. 6A) or cisplatin (0.05-0.2 mM) (FIG. 6B) for 24 or 48 h. Bars report the average of four experiments ±S.E. Each point was measured in quadruplicate and standard deviation calculated; asterisks next to brackets in FIG. 6A and FIG. 6B indicate statistically significant differences in drug response of D1 and E1 cells, p<0.05.

Figures 6A, 6B:
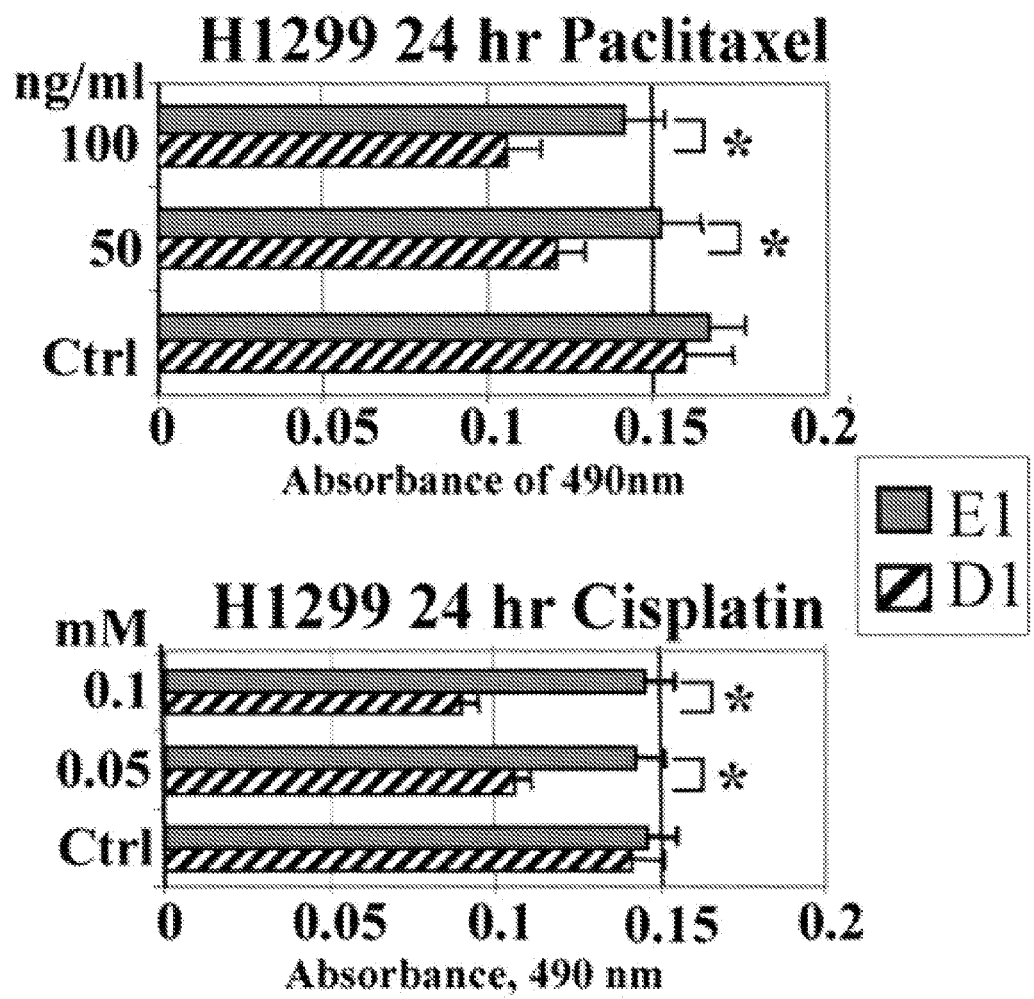
FIGS. 6A-E—Fhit enhances the sensitivity of cancer cells to paclitaxel and cisplatin.
Figures 6A, 6B:
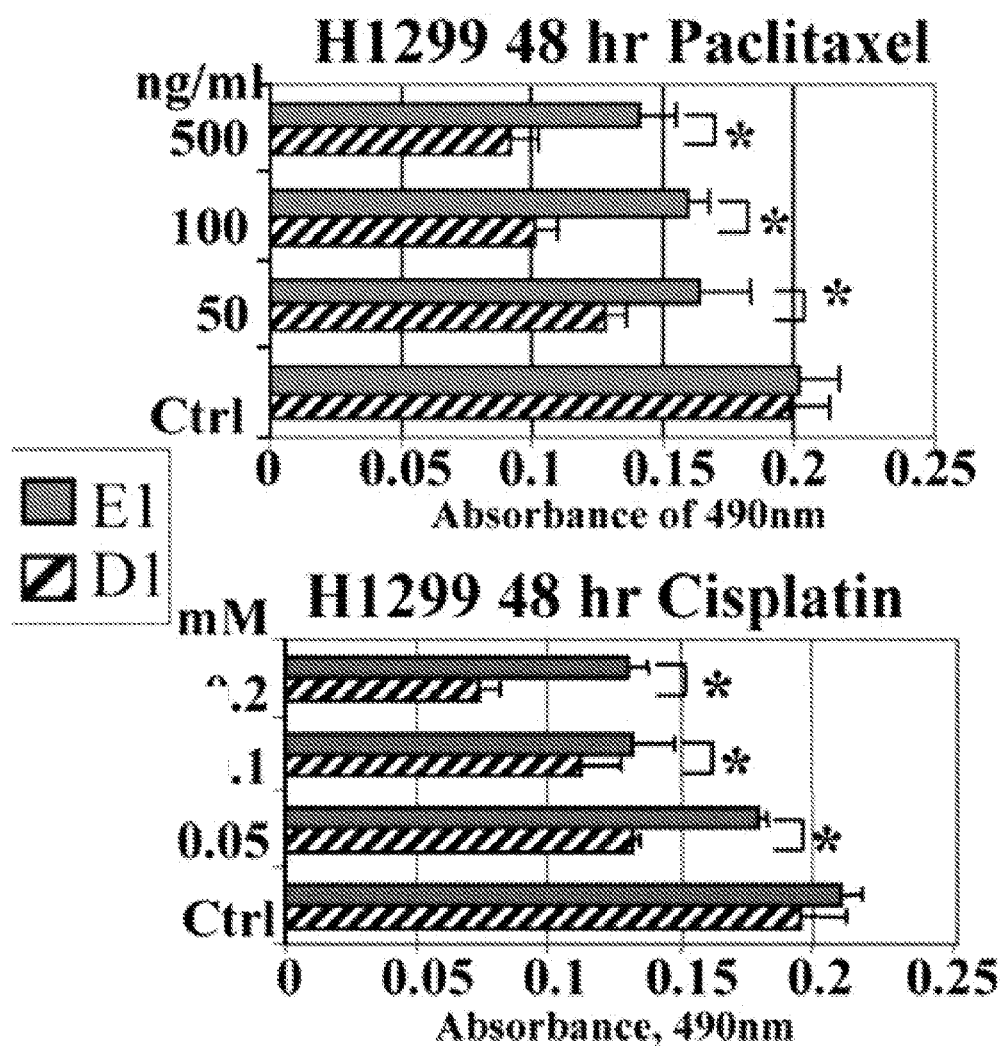
Figure 6C:
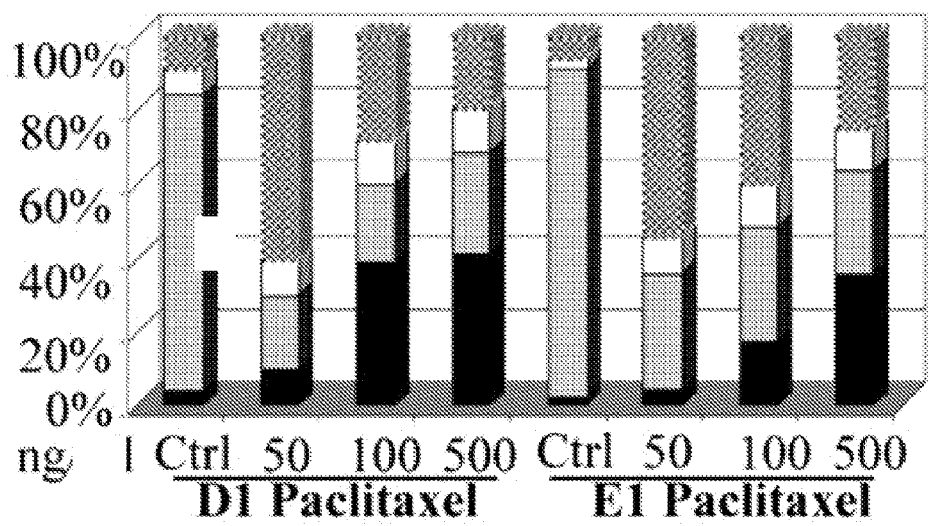
Figure 6D:
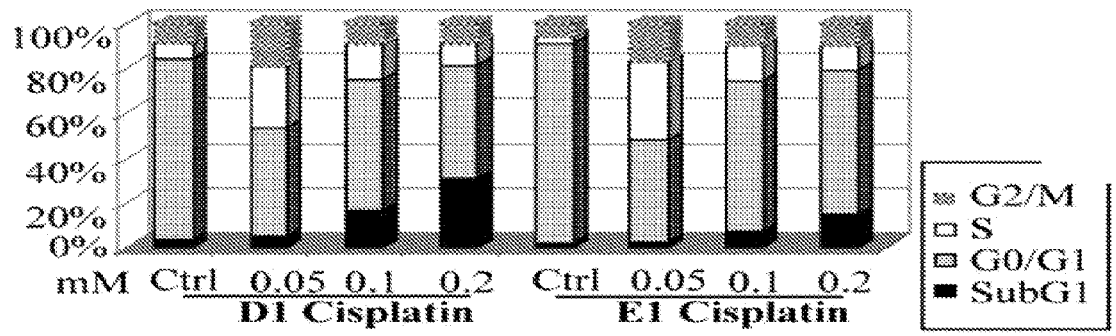

FIG. 6C and FIG. 6D, the graphs show representative results of flow cytometry analyses of E1 and D1 cells. Cells were treated with PonA for 48 h and then with paclitaxel (50-500 ng/ml) (FIG. 6C) or cisplatin (0.05-0.2 mM) (FIG. 6D). Each data point was measured in triplicate at 24, 48, and 72 h (data shown for 48 h).

Figure 6E:
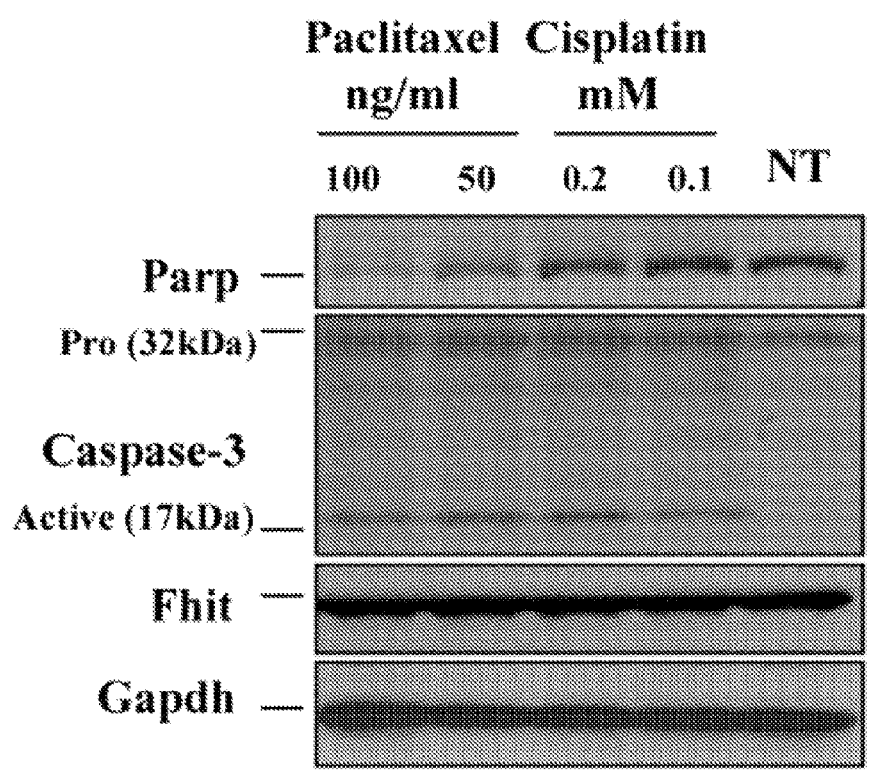

FIG. 6E, caspase 3 and Parp1 cleavage: immunoblot analyses, using Fhit, caspase 3, and Parp1 antisera, of total cell lysates from PonA-induced D1 cells after 48 h of treatment with paclitaxel (50 and 100 ng/ml) or cisplatin (0.05 and 0.1 mM). GAPDH served as loading control.

FIG. 7. TABLE 1 Candidate Fhit protein partners isolated through mass spectrometry. Proteins selectively captured in the A549 AdFHIT-H$_6$-infected cells sample. Amino acid sequence of identified peptides, Mascot scores, and protein sequence coverage are listed.

Figure 8A:
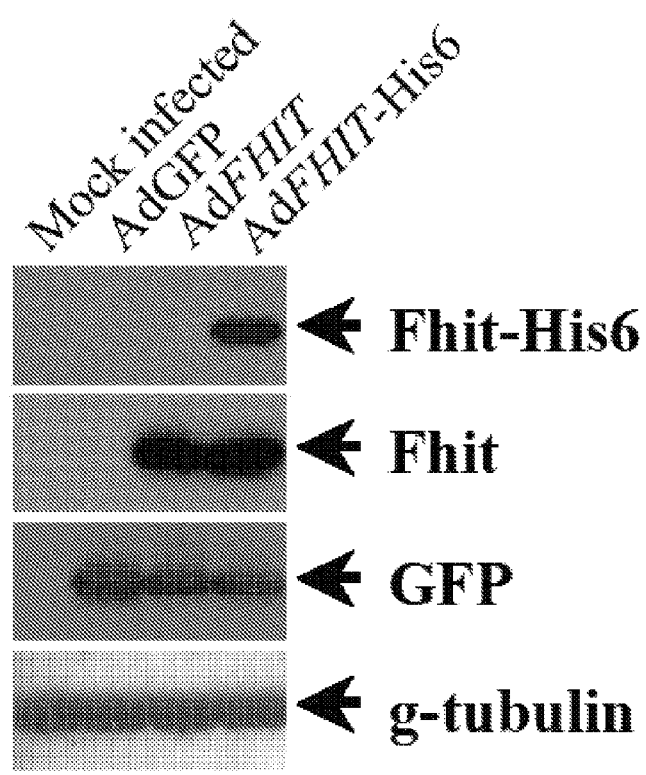
Figure 8C:
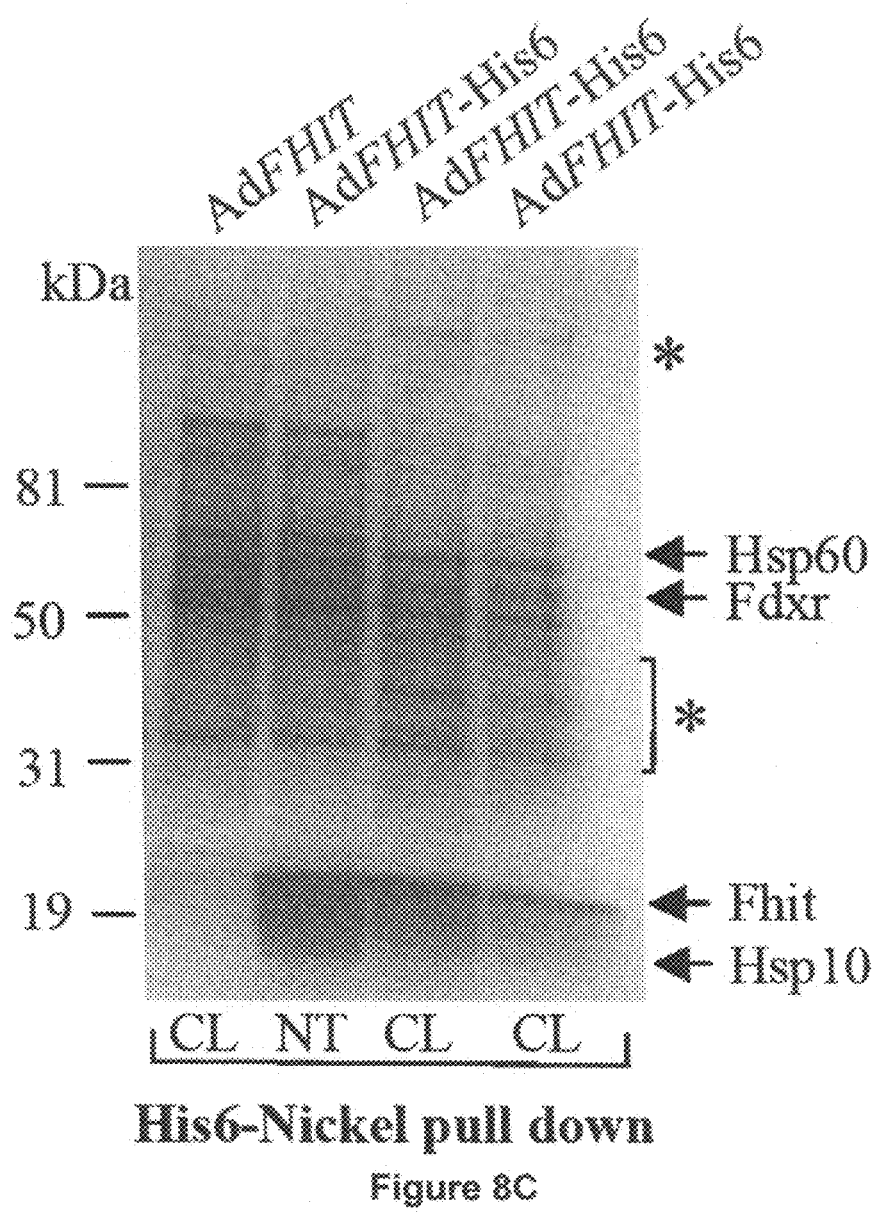
Figure 9A:
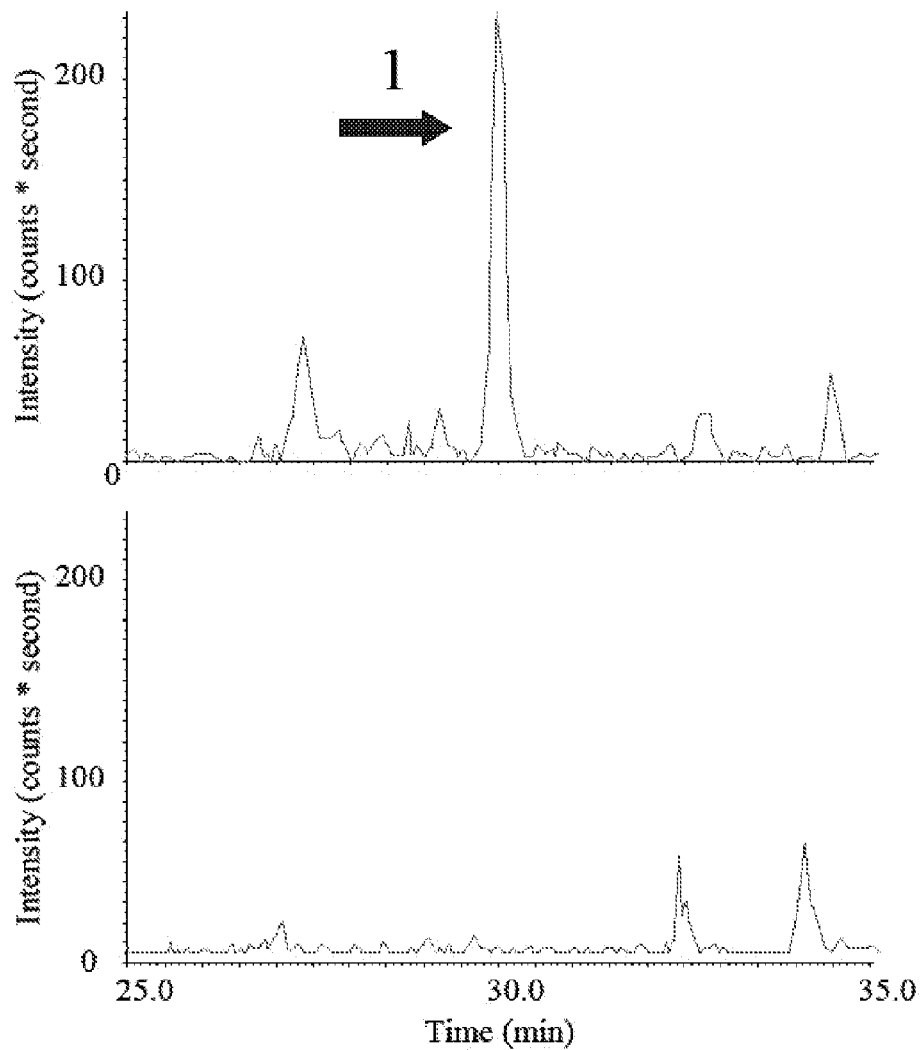
Figure 9B:
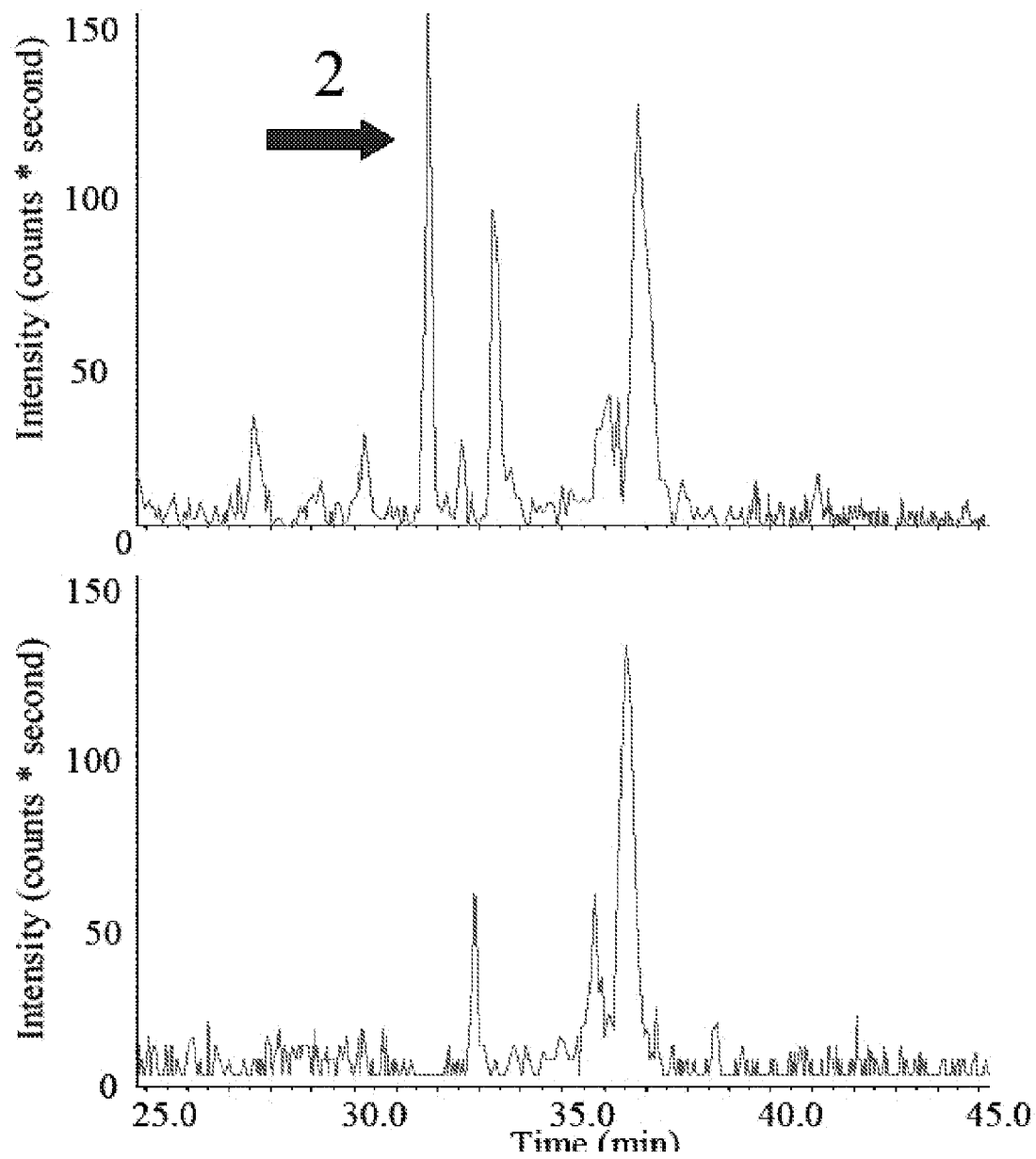
Figure 9C:
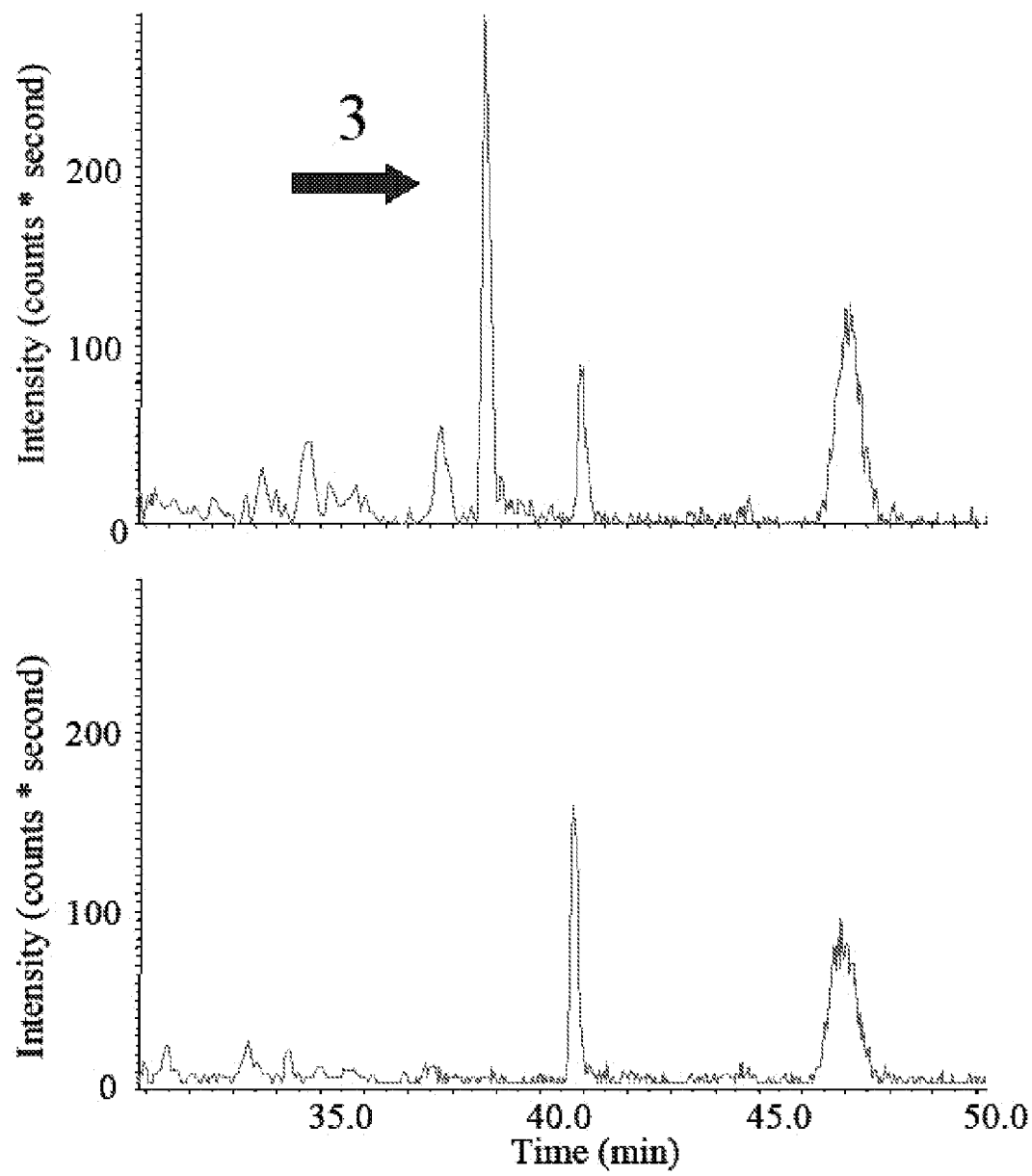
Figure 9D:
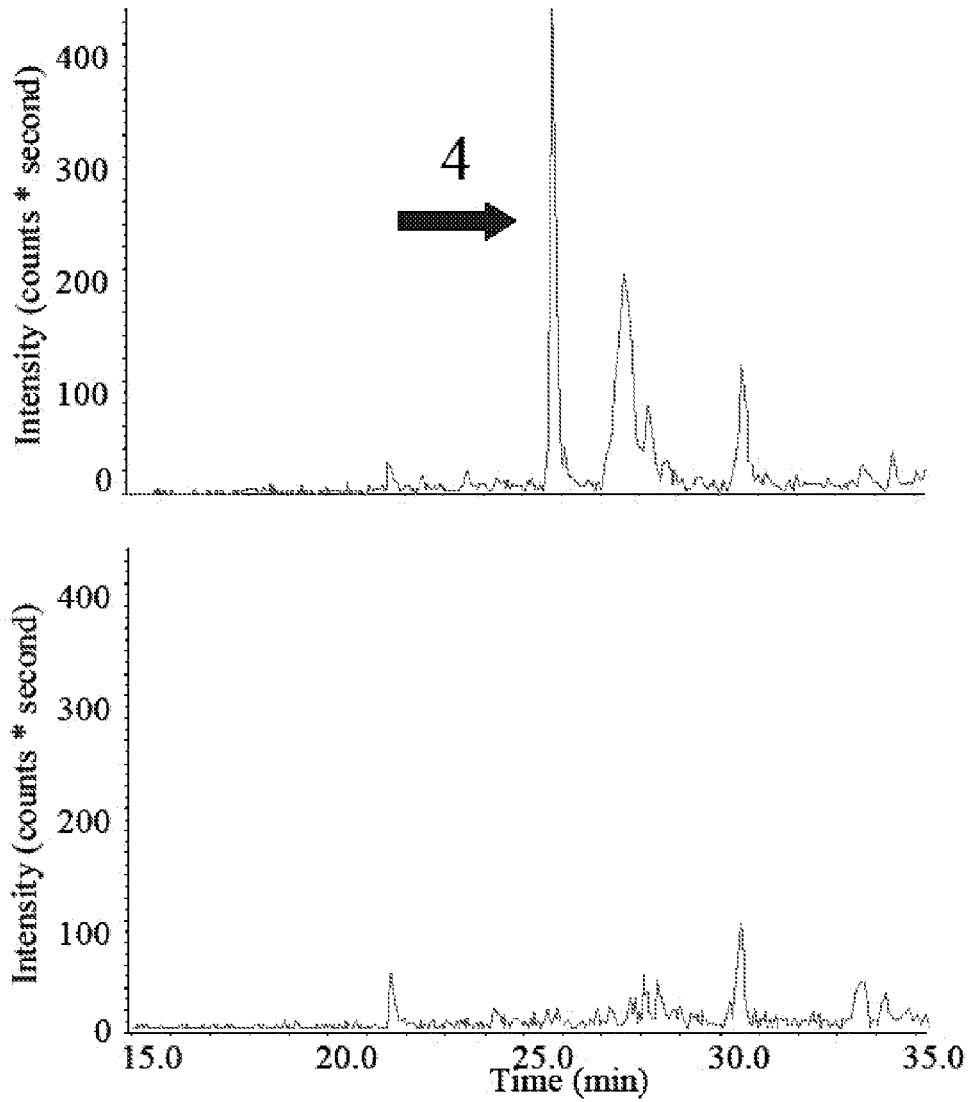
Figure 9E:
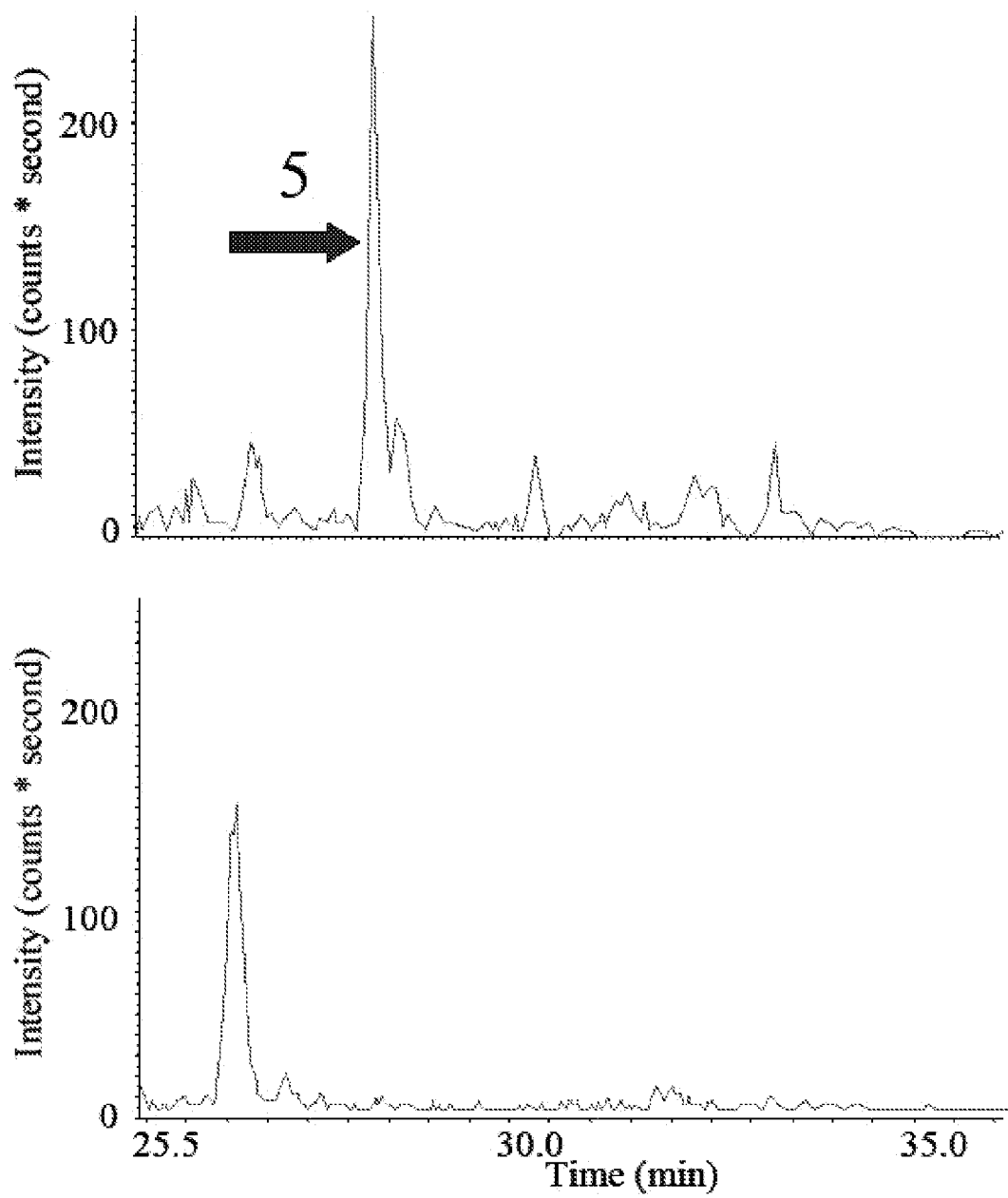
Figure 9F:
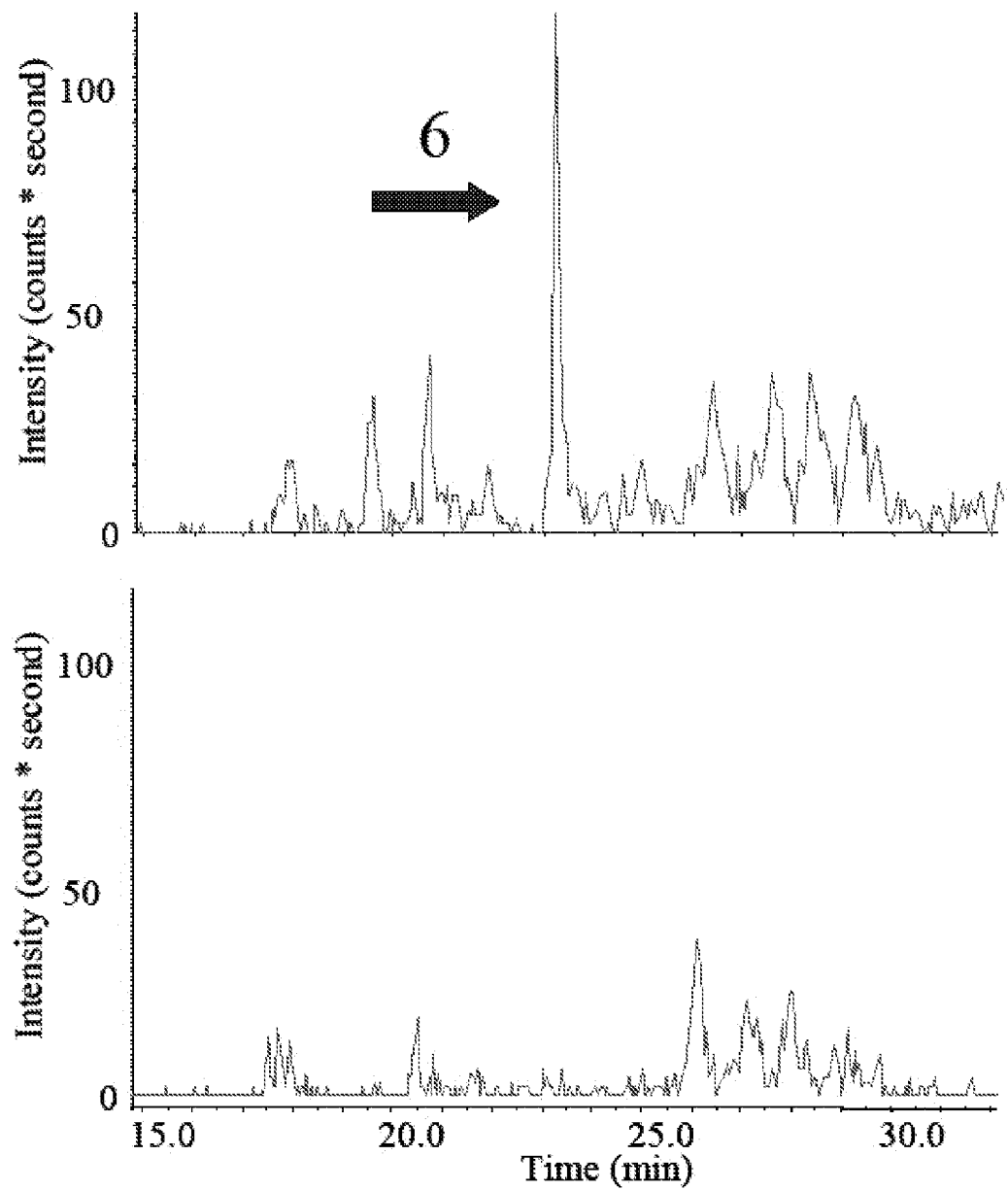

FIGS. 8A-8C. Ad-His6 biological activity is comparable to AdFHIT.

FIG. 8A, Western blot analysis of A549 cells infected with Ad-His6, MOI 20. Fhit-His protein was detected by antipentaHis and antiFhit serum. Both Ad FHIT and Ad-His6 carry a GFP cDNA regulated by a CMV5 promoter through an internal ribosome entry sequence downstream of FHIT. γ-tubulin was used to normalize sample loading.

FIG. 8B, Flow cytometry analysis of A549 cells 96 hr after infection with Ad-His6, MOI 15. Upper panel indicates the subG1 DNA content of infected cells (experiment repeated thrice; average values of subG1 fractions 22%+/−4.3 for Ad FHIT, 29%+/−5 for Ad-His6; the difference is not statistically significant; lower panel shows percentages of cells with mature caspase-3, an indication of apoptosis. The extent of cell death in A549 cells infected with Ad-His6 is comparable to the result obtained after infection with Ad FHIT.

FIG. 8C, In vivo cross-linking of Fhit-His6. Silver staining of gel with cell lysates after His6 pull down and cross-link reversal conditions, separated by 4-20% gradient SDS-PAGE. Internal negative controls included His6 pull down of Ad FHIT infected cells (cross-linked, CL) and Ad-His6 infected cells (not cross-linked, NT).

FIGS. 9A-9F. Initial validation of candidate Fhit protein partners identified through nanobore LC-MS/MS. Selected ion chromatograms (SIC) for AdFHIT-His6 and control samples are shown. The six SICs pairs reportion currents of the six following m/z values: 1) 672.8 (peak at retention time 30 min. was identified as tryptic peptide TVIIEQSWGSPK [SEQ ID NO: 5] belonging to Hsp60), 2) 685.4 (peak at retention time 32 min. identified as tryptic peptide LGPALATGNVVVMK [SEQ ID NO: 22] belonging to Aldh2), 3) 617.3 (peak at retention time 39 min. identified as tryptic peptide IFGVTTLDIVR [SEQ ID NO: 10] belonging to Mdh), 4) 658.4 (peak at retention time 26 min. identified as tryptic peptide VLQATVVAVGSGSK [SEQ ID NO: 19] belonging to Hsp10), 5) 551.7 (peak at retention time 28 min. identified as tryptic peptide EIDGGLETLR [SEQ ID NO: 15] belonging to Etfb), 6) 598.3 (peak at retention time 23 min. identified as tryptic peptide FGVAPDHPEVK [SEQ ID NO: 23] belonging to Fdxr). Peptides of interest, indicated by red arrows, are exclusively present in Ad-His6 sample.

FIG. 10. TABLE 2, Fhit induces generation of ROS in MKN74 gastric cancer cells. ROS assessment was performed with MKN74A116, a human gastric cancer cell line carrying a p53 mutant allele and expressing exogenous Fhit; Fhit-negative MKN74E4 cells were used as a control. To induce ROS generation, we treated MKN74 cells for 5 hr with 0.5, 1.0 and 2.0 mM $H_2O_2$. Results indicate a significantly higher rate of ROS generation in cells expressing exogenous Fhit compared to controls; toxicity was observed in Fhit-expressing cells after 2 mM $H_2O_2$ treatment. Numbers report the average of four experiments ±S.E.

DETAILED DESCRIPTION OF THE PREFERRED EMBODIMENT

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

As used herein interchangeably, "gene product," "DNA" and "gene," are used herein interchangeably.

The following abbreviations may be used herein: GAPDH, glyceraldehyde-3-phosphate dehydrogenase; DSP, dithiobis (succinimidyl propionate); LC-MS/MS, liquid-chromatography tandem mass spectrometry; Fdxr, ferredoxin reductase; PonA, ponasterone A; m.o.i., multiplicity of infection; ROS, reactive oxygen species; FU, 5-fluorouracil; DCFH-DA, dichlorofluorescein-diacetate; DCF, 2',7'-dichlorofluorescein; CHX, cycloheximide; siRNA, small interfering RNA; RT, reverse transcriptase; MTS, 3-(4,5-dimethylthiazol-2-yl)-5-(3-carboxymethoxyphenyl)-2-(4-sulfophenyl)-2H-tetrazolium.

The section headings used herein are for organizational purposes only and are not to be construed as limiting the described subject matter in any way. All literature and similar materials cited in this application, including patents, patent applications, articles, books, treatises, and internet web pages are expressly incorporated by reference in their entirety for any purpose. In the event that one or more of the incorporated literature and similar materials defines or uses a term in such a way that it contradicts that term's definition in this application, this application controls.

Fhit protein is lost in most cancers, its restoration suppresses tumorigenicity, and virus-mediated FHIT gene therapy induces apoptosis and suppresses tumors in preclinical models. Protein cross-linking and proteomics methods are used to characterize a Fhit protein complex involved in triggering Fhit-mediated apoptosis. The complex includes Hsp60 and Hsp10 that mediate Fhit stability and may affect import into mitochondria, where it interacts with ferredoxin reductase, responsible for transferring electrons from NADPH to cytochrome P450 via ferredoxin. Viral-mediated Fhit restoration increases production of intracellular reactive oxygen species, followed by increased apoptosis of lung cancer cells under oxidative stress conditions; conversely, Fhit-negative cells escape apoptosis, carrying serious oxidative DNA damage that may contribute to an increased mutation rate. Characterization of Fhit interacting proteins has identified direct effectors of the Fhit-mediated apoptotic pathway that is lost in most cancers through loss of Fhit.

Earlier searches for Fhit-interacting proteins pointed to several candidate proteins, none of which we could confirm as interactors by co-immunoprecipitation experiments, including Ubc9, α-tubulin, and Mdm2 (35-37). To readdress the question of Fhit protein interactors, the following was used: adenovirus-transduced Fhit-His$_6$ for Fhit complex purification after cross-linking, and Fhit-linked proteins, Hsp60, Hsp10, and Fdxr, were identified; subcellular location of these proteins suggested that mitochondria might be foci of Fhit activity. Hsp "stress proteins" as molecular chaperones perform functions such as protein translocation, folding, and assembly (38). The finding that Fhit interacts with Hsp60/Hsp10 after AdFHIT infection suggests that the Hsp complex may be important for Fhit stability, and possibly for its correct folding to import it into mitochondria, prior to activation of the apoptotic pathway, a suggestion we investigated by knocking down expression of Hsp60, Hsp10, or both in AdFHIT-infected lung cancer cells; Fhit stability was assessed after CHX chase in H1299 D1 cells, the lung cancer cell line expressing inducible Fhit. The level of Fhit protein in isolated mitochondria after knockdown of both Hsp60 and -10 was reduced, strengthening the proposal that Fhit-Hsp60/10 interaction is involved in Fhit stabilization and/or in correct folding for importation into mitochondria.

Targeted disruption of the FDXR gene in HCT116 colon cancer cells showed that it was essential for viability; reduction of the gene copy number resulted in decreased sensitivity to 5-fluorouracil-induced apoptosis (29) and FDXR is a target gene of the p53 family (30). Overexpression of Fdxr-sensitized colon cancer cells to $H_2O_2$, 5-fluorouracil, and doxorubicin-induced cell death, indicating that Fdxr contributes to p53-mediated apoptosis through generation of oxidative stress in mitochondria. Thus, activated p53 induces apoptosis in response to cellular stresses in part through ROS, and simultaneously p53 increases transcription of the FDXR gene, which in turn enhances p53 function by increasing ROS-induced apoptosis (29, 30).

Now shown herein is the presence of Fhit in the mitochondrial fraction; when Fhit is overexpressed or Fhit-expressing cells are stressed, Fhit can protect Fdxr from proteosomal degradation, leading to an increase in the Fdxr protein level, which is associated with generation of ROS and followed by apoptosis. Fhit does not affect the FDXR transcriptional level but may affect stability of the protein. In H1299 cells, missing both Fhit and p53, Fdxr overexpression increases sensitivity to ROS-induced cell death, and H1299 cells expressing inducible Fhit or p53 are sensitive to ROS-induced cell death; cancer cells missing Fhit, p53, or both would lack ways to increase Fdxr expression, and would be less sensitive to oxidative damage and would survive.

Discovery of the mitochondrial function of Fhit in apoptosis through interaction with Fdxr now extends functional parallels of the important tumor suppressors, Fhit and p53, lost sequentially in most cancers and involved in response to DNA damage, and illuminates their differences, with p53 acting as a transcriptional and Fhit a post-transcriptional Fdxr regulator. Delineation of direct downstream effectors of the Fhit suppressor pathway will lead to mechanistic studies of Fhit function that may influence preventive and therapeutic strategies to activate the Fhit pathway.

The finding that ROS generation is crucial for Fhit-mediated apoptosis emphasizes the importance of Fhit loss as a negative prognostic factor in various clinical settings; for example, assessment of Fhit status in preneoplastic or neoplastic conditions may be predictive of responses to antioxidant treatments.

To identify proteins that interact with Fhit to effect downstream apoptotic pathways, the inventors herein cross-linked proteins within cells after viral-mediated Fhit overexpression in lung cancer cells, and characterized proteins associated with Fhit and the pathways affected by them.

Results.

Isolation of a Fhit Protein Complex—To identify Fhit-interacting proteins, we generated an adenovirus carrying FHIT cDNA modified at its 3' end with a sequence encoding a $His_6$ epitope tag (AdFHIT-$His_6$). The biological activity of this tagged Fhit protein expressed in A549 cells was comparable with wild-type Fhit activity (FIG. 8).

A549 lung cancer-derived cells, which are susceptible to Fhit-induced apoptosis (10), were infected with AdFHIT or AdFHIT-$His_6$ and treated with DSP, a cross-linker that crosses membranes and fixes proteins in complex in vivo. Cells were lysed and proteins isolated with nickel beads avid for the $His_6$ epitope tag. Purified proteins were treated with dithiothreitol to cleave DSP and dissociate the complex, and digested by trypsin; protein constituents were identified by LC-MS/MS (FIG. 7—Table 1 and FIG. 9).

TABLE 1

| Protein | Accession no. | Molecular mass kDa | Function/ category | Subcellular localization | No. identified peptides | Peptide sequences | SEQ ID NO: | Protein Mascot score | Sequence coverage |
|---|---|---|---|---|---|---|---|---|---|
| Hsp60 | NP_002147 | 60 | 60-kDa Heat shock protein | Cytosol/ mitochondria | 6 | VGEVIVTK | 1 | 239 | 10% |
| | | | | | | LSDGVAVLK | 2 | | |
| | | | | | | IGIEIIKR | 3 | | |
| | | | | | | VTDALNATR | 4 | | |
| | | | | | | TVIIEQSWGSPK | 5 | | |
| | | | | | | VGGTSDVEVNEKK | 6 | | |
| Malate dehydrogenase (Mdh) | NP_005909 | 33 | Catalyzes the reversible oxidation of malate to oxaloacetate | Mitochondrial matrix | 8 | ANTFVAELK | 7 | 193 | 28% |
| | | | | | | IQEAGTEVVK | 8 | | |
| | | | | | | VNVPVIGGHAGK | 9 | | |
| | | | | | | IFGVTTLDIVR | 10 | | |
| | | | | | | FVFSLVDAMNGK | 11 | | |
| | | | | | | GCDVVVIPAGVPR | 12 | | |
| | | | | | | AGAGSATLSMAYAGAR | 13 | | |
| | | | | | | GYLGPEQLPDCLK | 14 | | |

TABLE 1-continued

| Protein | Accession no. | Molecular mass kDa | Function/ category | Subcellular localization | No. identified peptides | Peptide sequences | SEQ ID NO: | Protein Mascot score | Sequence coverage |
|---|---|---|---|---|---|---|---|---|---|
| Electron transfer flavor protein (Etfb) | NP_001976 | 28 | Specific electron acceptor for mitochondrial dehydrogenases | Mitochondrial matrix | 3 | EIDGGL ETLR | 15 | 96 | 12% |
| | | | | | | VETTED LVAK | 16 | | |
| | | | | | | LSVISVE DPPQR | 17 | | |
| Hsp10 | AAC 96332 | 10 | 10-kDa Heat shock protein | Cytosol/ mitochondria | 3 | GGEIQP VSVK | 18 | 92 | 34% |
| | | | | | | VLQATV VAVGS GSK | 19 | | |
| | | | | | | VVLDD KDYFLF R | 20 | | |
| Mitochondrial aldehyde dehydrogenase 2 (Adh2) | NP_000681 | 55 | Second enzyme of the major oxidative pathway of alcohol metabolism | Mitochondrial matrix | 2 | LADLIE R | 21 | 75 | 4% |
| | | | | | | LGPALA TGNVV VMK | 22 | | |
| Ferredoxin reductase (Fdxr) | P22570 | 54 | First electron transfer protein in all the mitochondrial p450 systems | Mitochondrial matrix | 1 | FGVAPD HPEVK | 23 | 47 | 2% |

Six proteins were identified, all with mitochondrial localization: Hsp60 and 10, ferredoxin reductase (Fdxr), malate dehydrogenase, electron-transfer flavoprotein, and mitochondrial aldehyde dehydrogenase 2; Hsp60 and Hsp10 are also distributed in the cytosol (23).

Figure 1A:
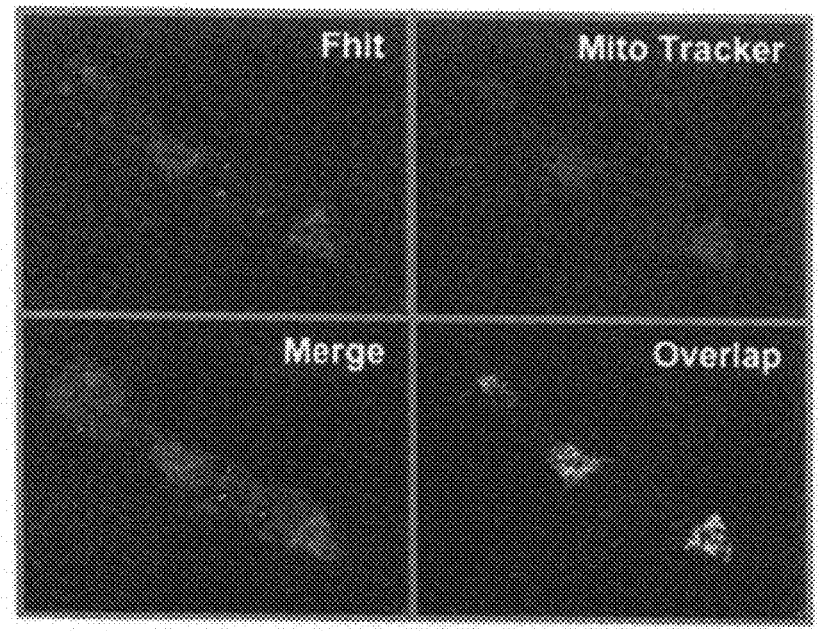
Figure 1B:
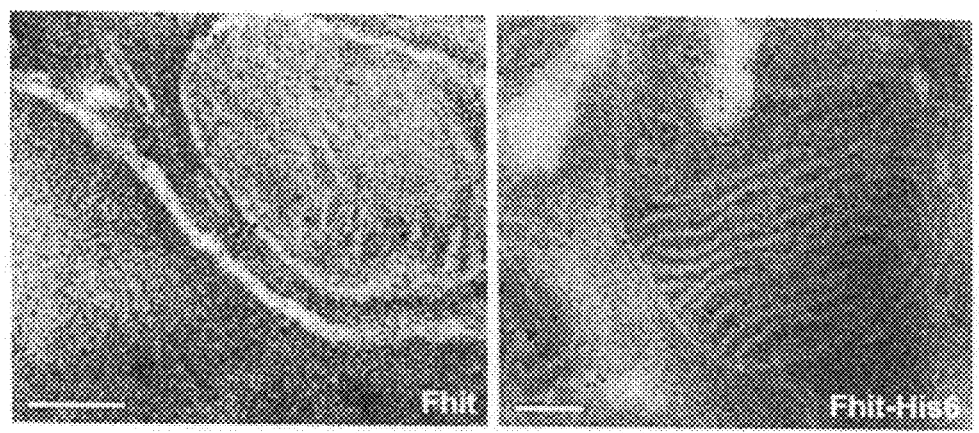

Fhit Subcellular Localization—Because candidate Fhit interactors are mitochondrial proteins, the inventors herein determined if Fhit, which lacks a mitochondrial localization signal, localized in these organelles. Fhit negative H1299 lung cancer cells carrying an inducible FHIT cDNA (D1 cells) were treated with the inducer, PonA for 48 h and indirect immunofluorescence detection of Fhit subcellular location was assessed using anti-Fhit serum and MitoTracker Red 580, a marker of mitochondria; Fhit fluorescent signal (green staining, FIG. 1A) was cytoplasmic and partly co-localized (yellow staining, FIG. 1A, lower right) with MitoTracker Red dye, indicating that exogenous Fhit localized to mitochondria and cytosol. Anti-Fhit specificity was confirmed by absence of green fluorescence in the Fhit negative H1299 clone E1 cells (not shown). To confirm mitochondrial localization, A549 cells infected with AdFHIT-His$_6$ or AdFHIT at m.o.i. 20 were examined by immunoelectron microscopy 48 h later, by anti-pentaHis staining; FhitHis6-transduced cells demonstrated significant numbers of gold particles in mitochondria (FIG. 1B, right panel), whereas AdFHIT-transduced cells showed sparse reactivity (FIG. 1B, left panel).

To assess Fhit submitochondrial localization, mitochondria were purified from A549 cells infected with AdFHIT m.o.i. 1, as described above. The sodium carbonate procedure is a nondestructive approach that allows effective release in the supernatant of both soluble proteins and peripheral membrane proteins from intracellular membranes after inducing the generation of open sheets of membranes; furthermore, it allows recovery of integral proteins with the membranes (pellet) (24).

FIG. 1E shows that Fhit was only detectable in the soluble fraction. To further define Fhit submitochondrial localization, mitochondria were treated with 0.10 and 0.15% digitonin to selectively disrupt mitochondrial outer membrane, releasing proteins contained in the intermembrane space and the matrix; as shown in FIG. 1F, gradual disruption of outer and inner membranes releases increasing amounts of Fhit protein, suggesting that Fhit is mainly distributed either at the luminal side of the inner membrane or in the matrix of mitochondria. Mitochondrial localization was confirmed in gastric cancer-derived MKN74A116 cells stably expressing exogenous Fhit (9) and in HCT116 colon cancer cells expressing endogenous Fhit (FIG. 1G and FIG. 1H).

Figure 2A:
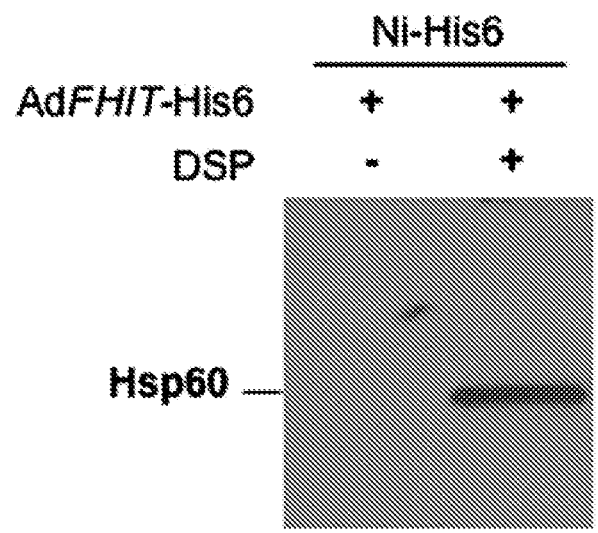
FIGS. 2A-F—Exogenous and endogenous Fhit forms a complex with endogenous Hsp60, Hsp10, and Fdxr proteins. Protein complexes, isolated with recombinant Fhit-$His_6$ protein, were separated on polyacrylamide gels and probed with antisera against Hsp60 (FIG. 2A), Hsp10 (FIG. 2B), and Fdxr (FIG. 2C); in the latter panel, prepared after mitochondria isolation, it is shown that Fhit recruits Fdxr in the mitochondria in a time-dependent manner. Filters were loaded with protein isolated after infection of A549 cells with AdFHIT-$His_6$ with or without DSP.
Figure 2B:
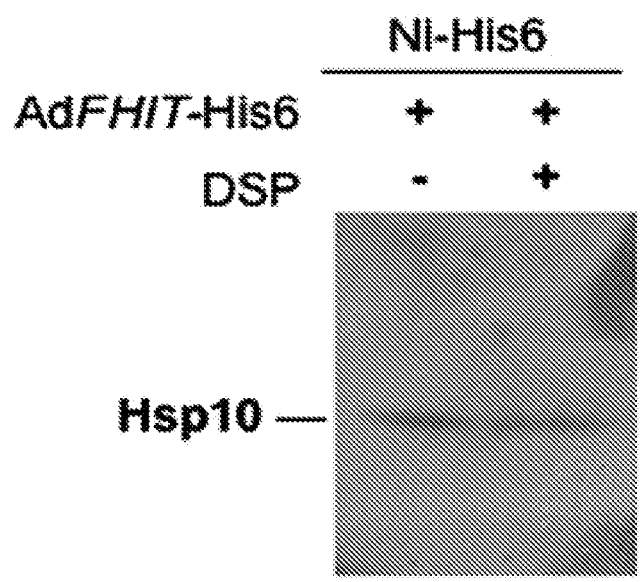
Figure 2C:
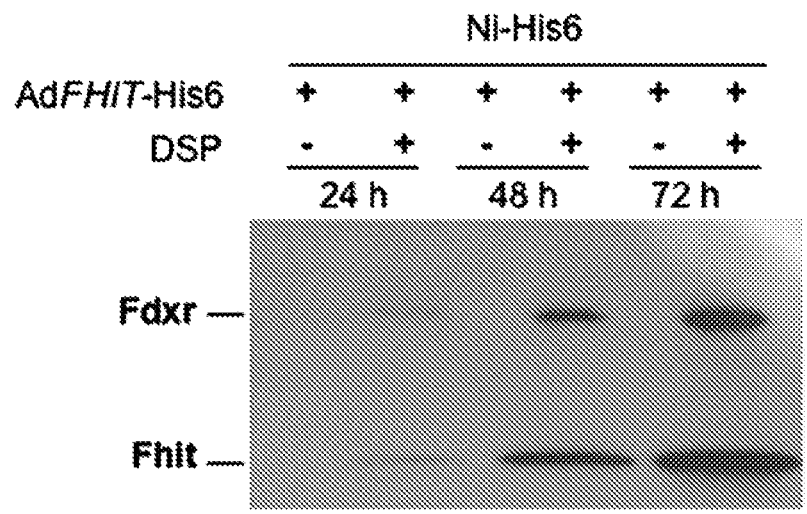

Fhit Interacts with Hsp60, Hsp10, and Fdxr—Among candidate interactor proteins, the inventors focused on Hsp60 and Hsp10 as possible chaperonins and on Fdxr, a mitochondrial respiratory chain protein transactivated by p53 and involved in responses to therapeutic drugs (25). To validate interactions, A549 cells were infected with AdFHIT or AdFHIT-His6 at m.o.i. 20, with or without DSP. Fhit complexes were purified through the His$_6$ tag and co-purified proteins were detected with antisera against Hsp60, Hsp10, and Fdxr; Hsp60 and Fdxr were detected only in lysates of cells exposed to DSP (FIG. 2A and FIG. 2C), whereas Hsp10 was also detectable without cross-linking (FIG. 2B).

Figure 2D:
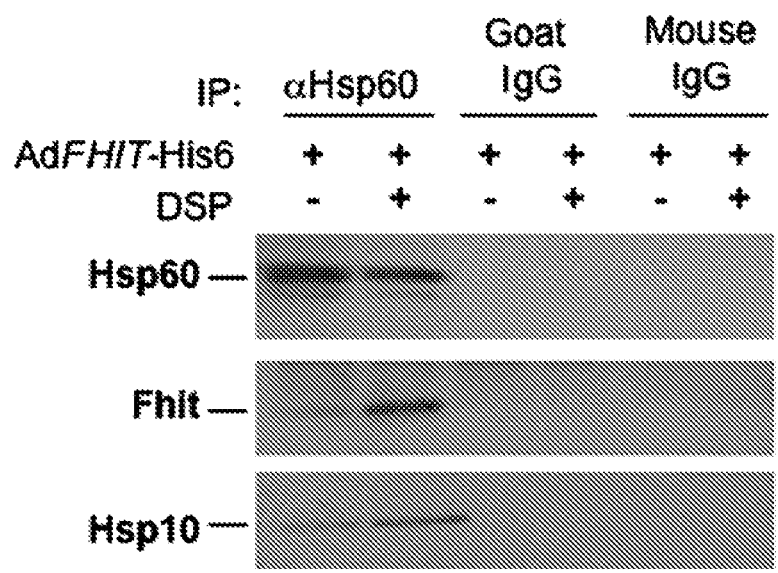

A time course experiment after infection showed recruitment of Fdxr by Fhit (FIG. 2C); also, endogenous Hsp60 co-immunoprecipitated Fhit and Hsp10 in the absence of DSP (FIG. 2D).

Figure 2E:
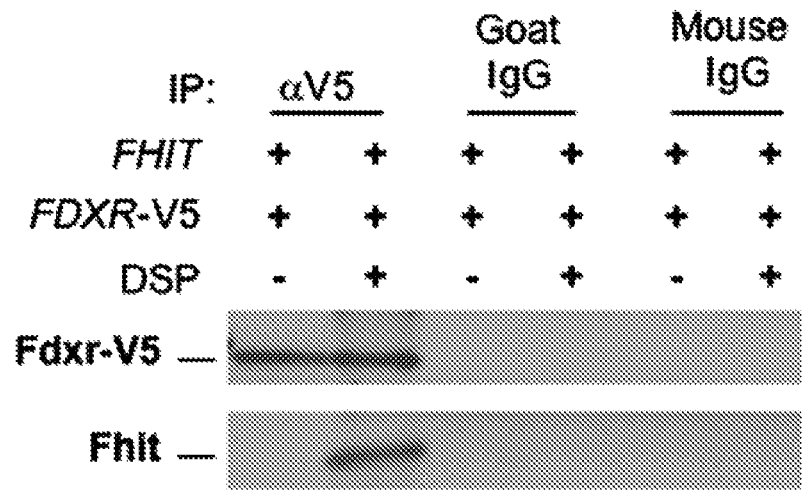

To verify specificity of interactions we generated an FDXR cDNA expression plasmid with a 3'V5 epitope tag. A549 cells were co-transfected with FDXR-V5 and FHIT plasmids, and proteins were precipitated with monoclonal anti-V5; co-precipitated Fhit was detectable only after DSP cross-linking (FIG. 2E).

Figure 2F:
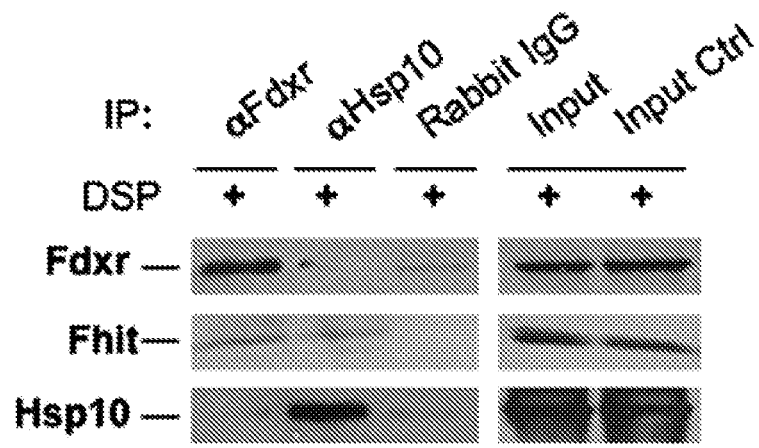

To determine whether these proteins also interact with endogenous Fhit, the inventors immunoprecipitated each endogenous candidate interactor protein from DSP-treated Fhit-positive HCT116 cells and looked for co-precipitation of endogenous Fhit (FIG. 2F).

Endogenous Fhit co-precipitated with Hsp10 and Fdxr, confirming the presence of endogenous Fhit in mitochondria and its interaction with endogenous chaperones and respiratory chain protein in the absence of stress.

Hsp60/10 Interaction Affects Fhit Stability and/or Mitochondrial Import—Hsp60 and -10 are molecular chaperones found in complex (26) and may be important for folding and import of proteins into mitochondria. The inventors herein now believe that the Hsp60/10 complex was responsible for Fhit correct folding and mitochondrial addressing.

Figure 3A:
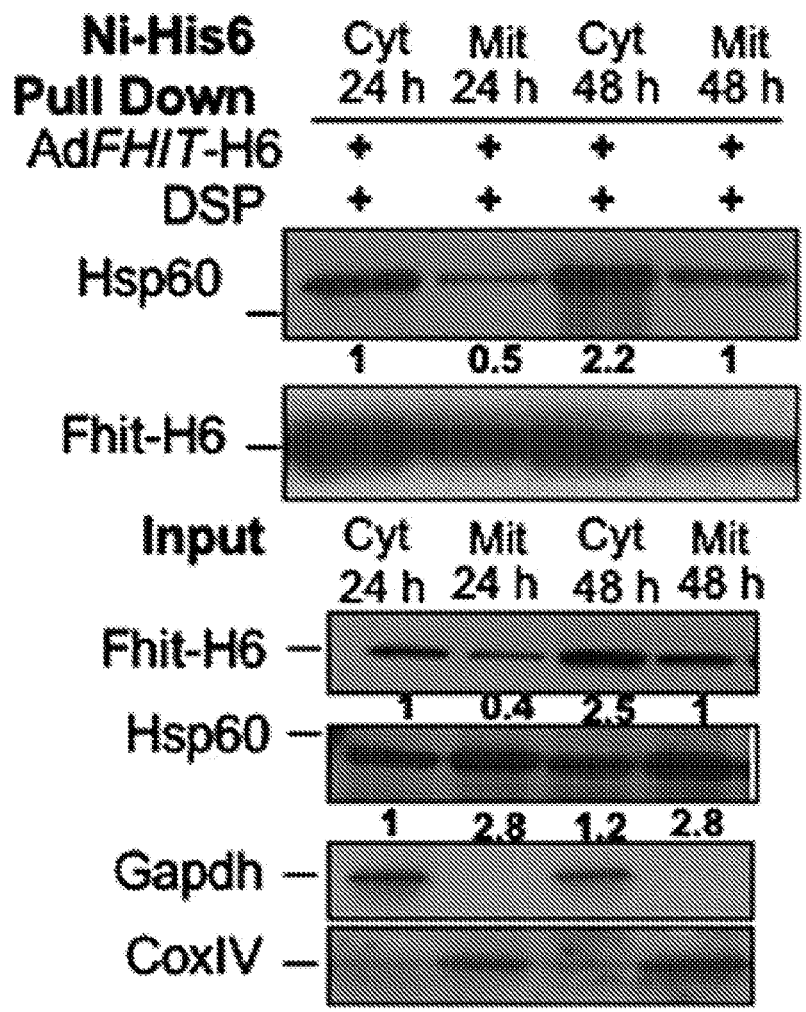
FIGS. 3A-D—Knockdown of Hsp60/Hsp10 reduces the level of Fhit in the mitochondria.

To investigate the location of these interactions, A549 cells were infected with AdFHIT-His$_6$ m.o.i. 5 and protein lysates were collected from cytosol and mitochondrial fractions after cross-linking. Complexes were isolated by Fhit-H6-nickel pull down, separated on a polyacrylamide gel, and filters probed with Hsp60 and Fhit antisera. At 24 and 48 h after infection interaction with Hsp60 is observed in the cytosol and mitochondria (FIG. 3A) commensurate with the increase in Fhit expression at these times (Input), as shown in FIG. 3A.

To determine whether the Fhit-Hsp60/10 interaction is important for the stability of the Fhit protein, H1299 with inducible Fhit expression (D1 cells) were transfected with Hsp60 and Hsp10 siRNAs and 72 h after transfection a CHX chase was performed at 1, 6, and 12 h and Fhit protein expression was assessed and compared with cells transfected with the scrambled sequence.

Figure 3B:
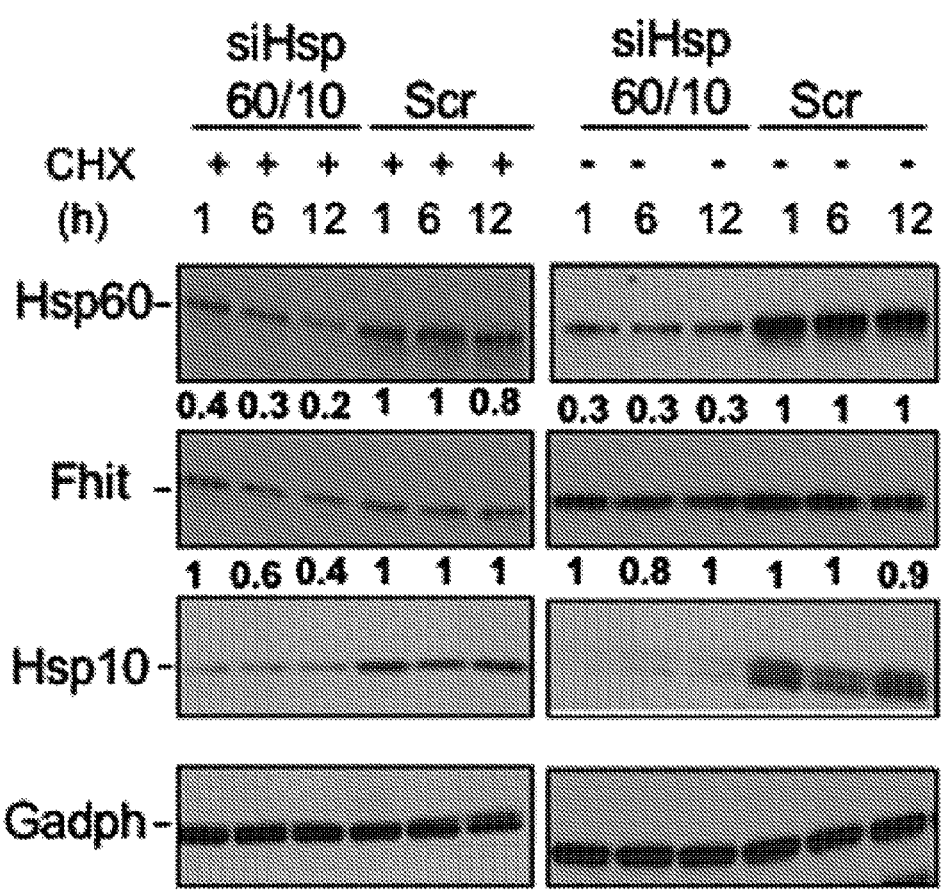

As shown in FIG. 3B at 6 and 12 h of CHX after Hsp60 and Hsp10 silencing, there is a strong reduction of Fhit expression (from 1 to 0.4 at 1 and 12 h, respectively). Next, Hsp60 and 10 siRNAs were transfected into A549 cells individually or in combination; 24 h later, cells were infected with AdFHIT m.o.i. 1 and cytosol and mitochondria were fractionated 24 h later. After silencing both Hsps, the Fhit level was unaffected in the cytosol but reduced in mitochondria compared with control (FIG. 3B), showing that the Hsp60/10 complex may mediate virally transduced Fhit stabilization and mitochondrial localization. It is also true that if Hsp60 and Hsp10 are involved in Fhit stability after Fhit viral transduction, the cellular compartment with less Fhit would be affected by a decrease in Fhit stability. The inventors herein also examined the Fhit complex in H1299 D1 cells expressing inducible Fhit, with Fhit negative E1 cells as control; 48 h after Fhit induction in D1 cells (FIG. 3C, left panel), distribution of the Fhit complex proteins was similar in the cytosol and mitochondria of D1 and E1 cells, with and without $H_2O_2$.

Figure 3C:
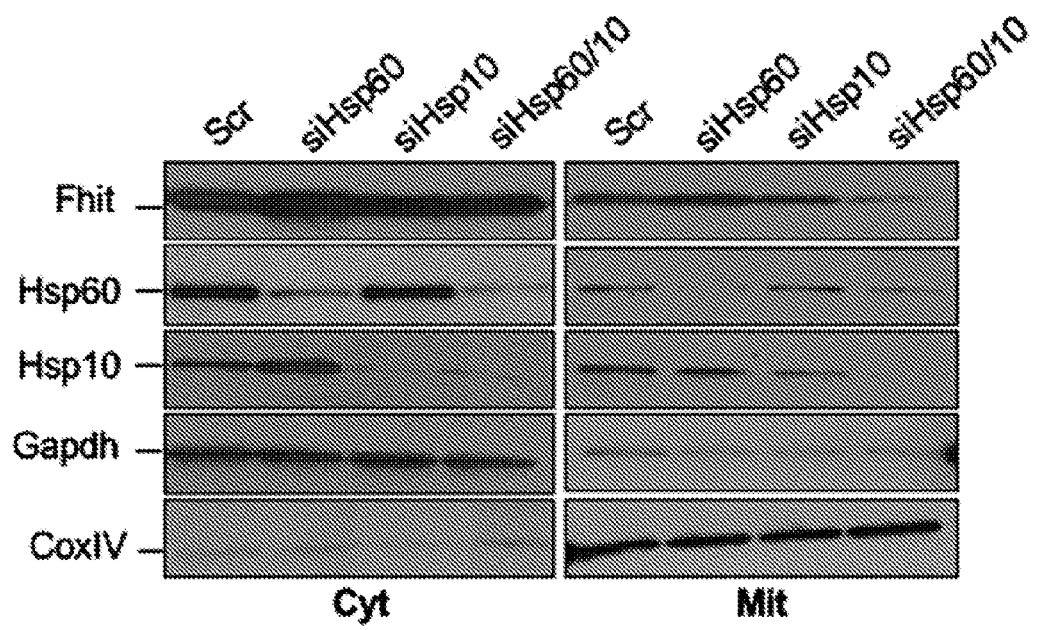
Figure 3D:
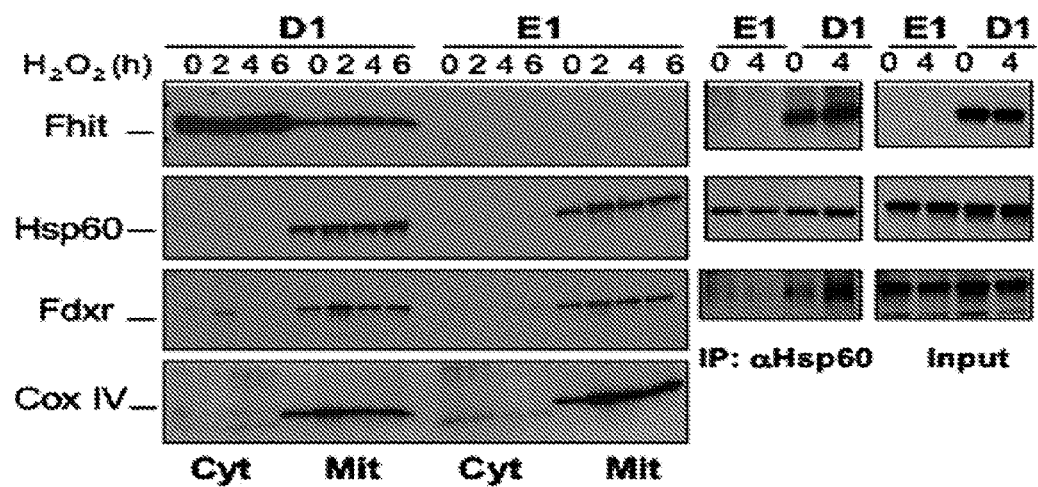

Hsp60 was immunoprecipitated from total cell lysates of these cells at 48 h after PonA induction, with or without $H_2O_2$, and coprecipitated Fhit and Fdxr (FIG. 3C, right panel). Induction of Fhit expression in D1 cells does not cause biological changes in vitro; thus the Fhit complex does not form as a consequence of apoptosis. A time course experiment was performed in D1 cells after PonA-induced Fhit expression, with and without stress conditions, to determine whether there were biological changes in Fhit protein interactors. The co-inventors did not detect changes in localization after Fhit expression.

Fhit Induces Generation of Reactive Oxygen Species (ROS)—Fdxr, a 54-kDa flavoprotein, is located on the matrix side of the inner mitochondrial membrane, and is responsible for transferring electrons from NADPH, via the single electron shuttle ferredoxin-cytochrome P450, to substrates (27). Under substrate-limiting conditions, electrons leak from this shuttling system and generate ROS (28). Fdxr mediates p53-dependent, 5-fluorouracil-induced apoptosis in colorectal cancer cells, through generation of ROS (29, 30), potent intracellular oxidants, and regulators of apoptosis (31).

Figure 4A:
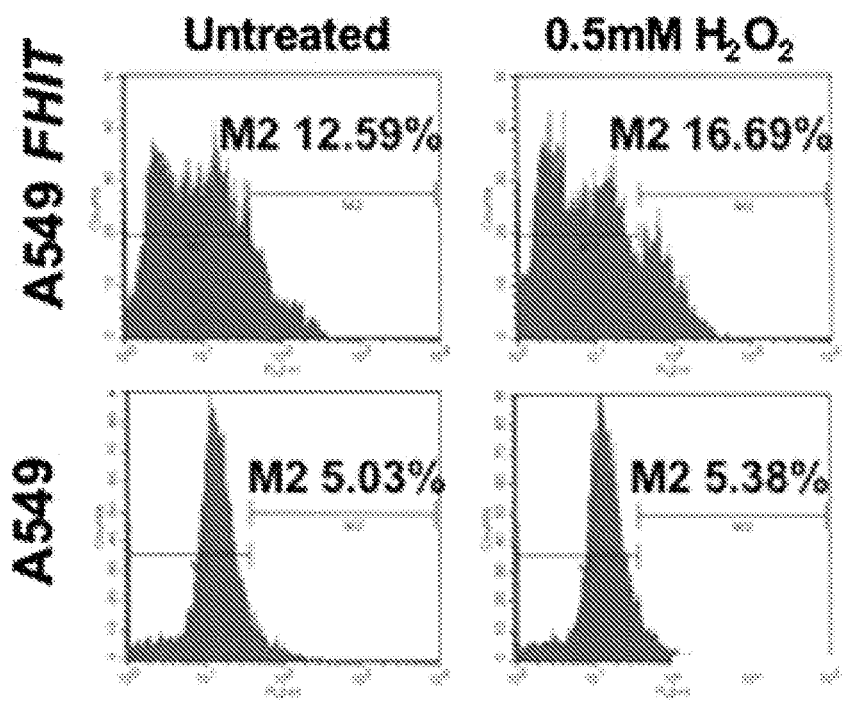
FIGS. 4A-F—Fhit expression induces intracellular ROS generation after treatment of cells with peroxide.
Figure 4A:
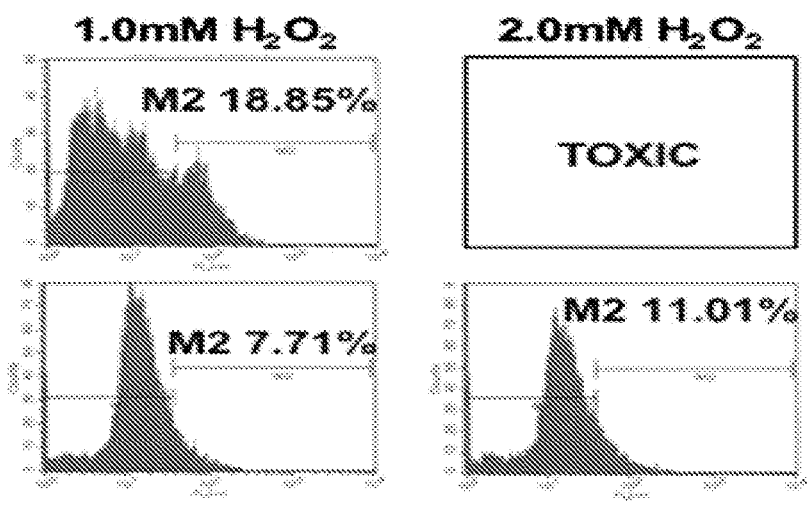

The inventors herein then investigated determine whether ROS production could be involved in Fhit-mediated apoptosis. Overexpression of Fdxr increases sensitivity of tumor cells to apoptosis on $H_2O_2$ treatment, through ROS production (29, 30). The inventors examined ROS production in A549 cells, with and without $H_2O_2$ treatment, after transient transfection with the FHIT expression plasmid. Intracellular superoxide was assessed by measuring ethidium fluorescence, as a result of oxidation of hydroethydine by superoxide. Intracellular superoxide was measured 5 h after stimulation with increasing concentrations of $H_2O_2$. ROS generation was ~3 times higher (16.7 versus 5.4% at 0.5 mM $H_2O_2$ and 18.8 versus 7.7% at 1.0 mM $H_2O_2$) in FHIT-transfected cells. 2 mM $H_2O_2$ was toxic to Fhit-expressing but not to non-expressing cells (FIG. 4A).

Figure 4B:
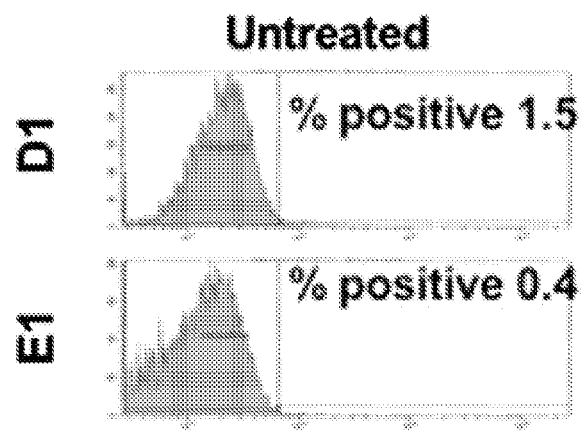
Figure 4B:
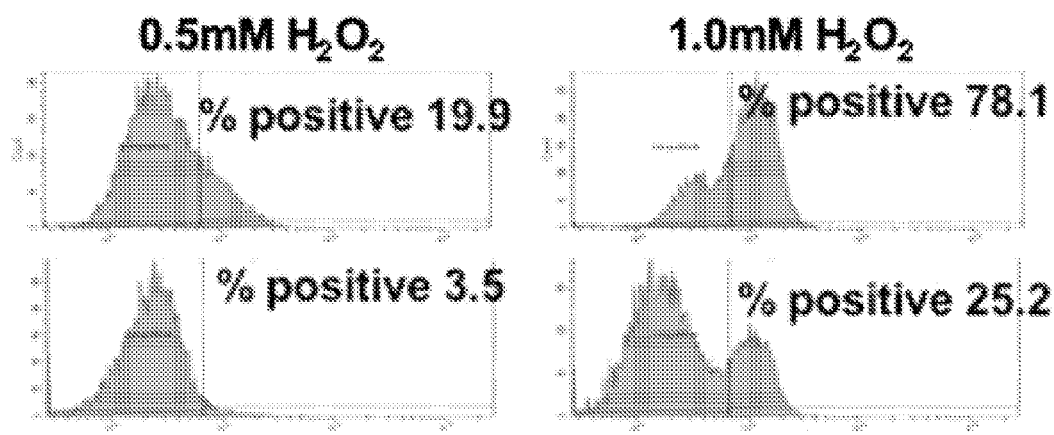

A similar experiment was performed with p53 and Fhit negative lung cancer-derived H1299 D1 and E1 clones carrying PonA-inducible FHIT and empty vector expression plasmids, respectively; the cells were treated with 5 μM PonA and at 48 h treated with 0.5 and 1.0 mM $H_2O_2$; the % ROS-positive cells was higher in Fhit-positive D1 cells than in E1 control cells (20 versus 3.5% at 0.5 mM $H_2O_2$, and 78 versus 25% at 1.0 mM $H_2O_2$, respectively) (FIG. 4B).

These results were paralleled by experiments with human gastric cancer-derived cells, MKN74A116 (FIG. 10), which express mutant p53 (32) and stably express exogenous Fhit (9).

Figure 4C:
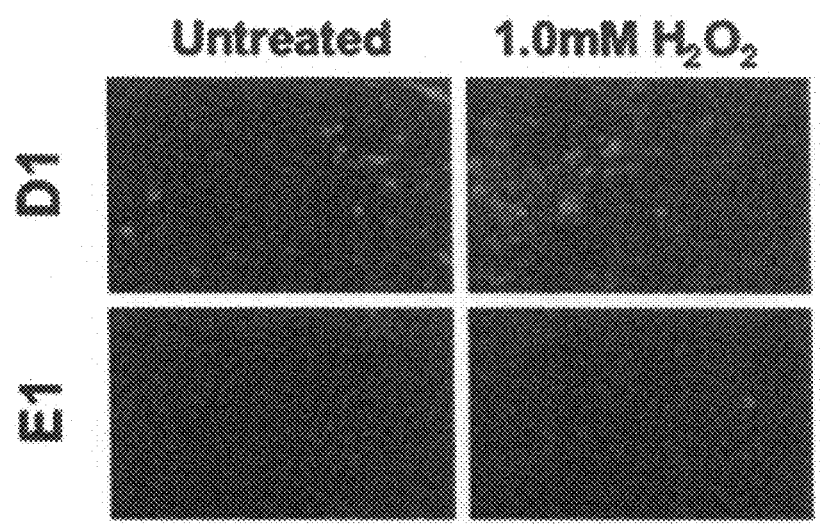

To further study the generation of ROS after Fhit reconstitution during oxidative stress, DCFH-DA was used to measure the redox state of Fhit-overexpres sing cells. Peroxidases, cytochrome c, and $Fe^{2+}$ can oxidize DCFH-DA to fluorescent 2',7'-dichlorofluorescein (DCF) in the presence of $H_2O_2$; thus, DCF indicates $H_2O_2$ levels and peroxidase activity. Increased DCF fluorescence was detected in D1 cells compared with E1 cells under stress conditions (FIG. 4C).

Figure 4D:
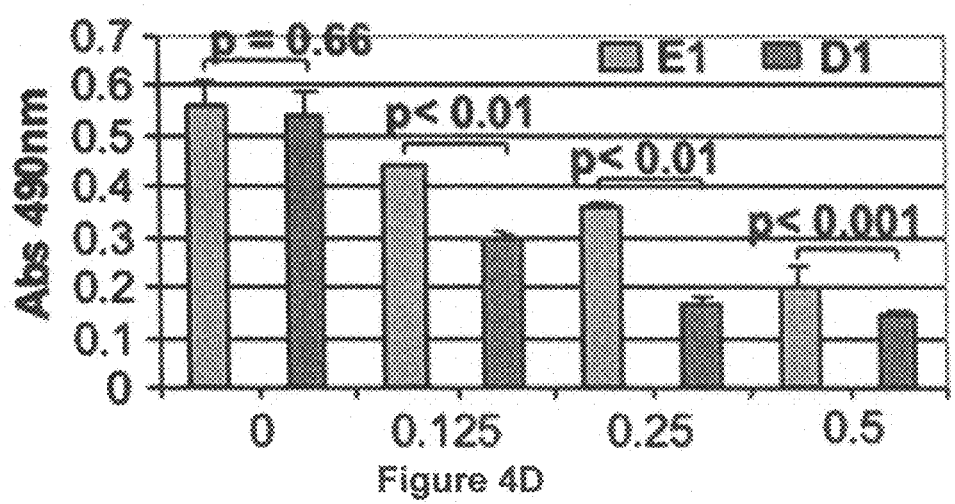

The decreased cell viability after $H_2O_2$ treatment in Fhit-expressing cells was also assessed by an MTS cytotoxicity assay 24 h after $H_2O_2$ treatment. $H_2O_2$ treatment caused reduced cell viability or growth arrest in both E1 and D1 cells, but this phenotype was more pronounced in D1 cells (FIG. 4D).

Figure 4E:
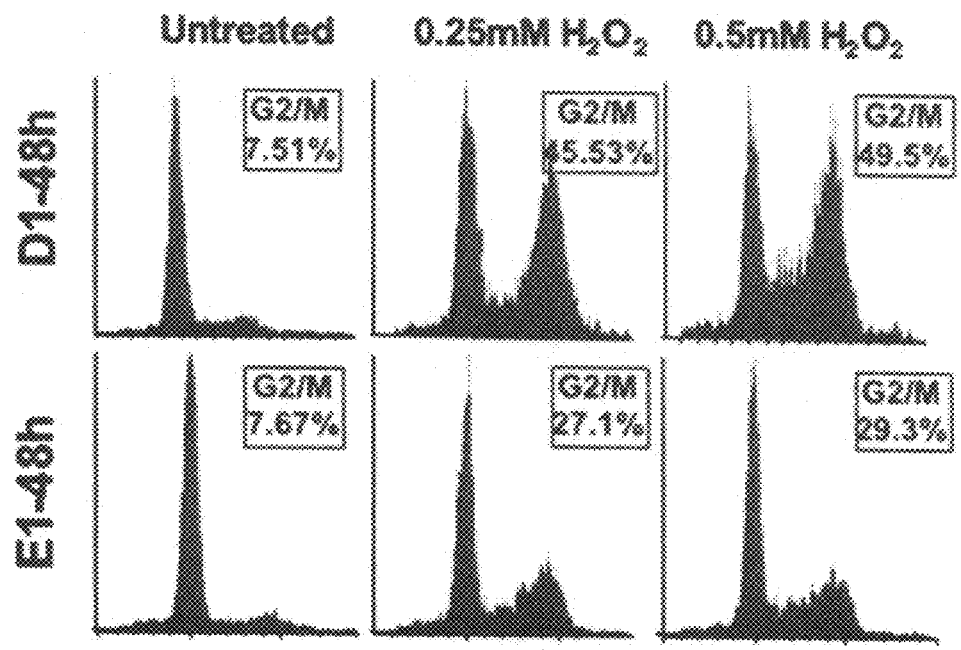

To determine whether $H_2O_2$ treatment with or without Fhit could affect cell viability or cell cycle kinetics we performed flow cytometry (FIG. 4E); when Fhit was present under stress conditions there was a consistent increase of $G_2$/M arrest at 48 h after 0.25 and 0.5 mM $H_2O_2$ treatment, 45.5 and 49.5%, respectively, compared with 27.5 and 29% of E1 cells under the same conditions.

Figure 4F:
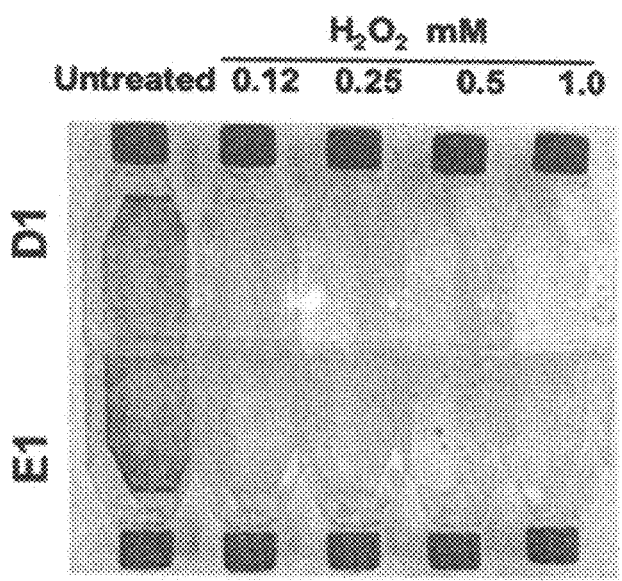

To assess if the $G_2$/M arrest could affect long-term viability of the cells, a colony assay was performed (FIG. 4F). No colonies were detected in Fhit-express sing cells after exposure to 0.25 mM or higher concentrations of $H_2O_2$.

Figure 5A:
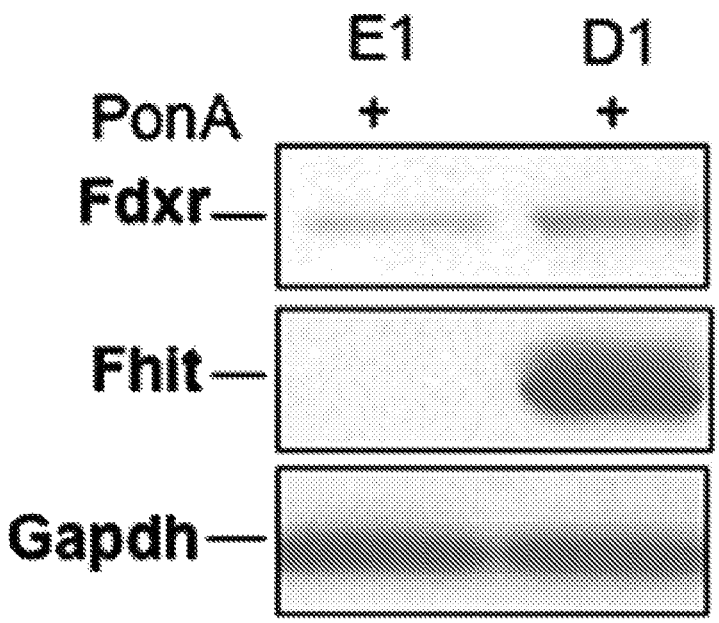
FIGS. 5A-H.—Apoptosis triggered by Fhit viral transduction can be mediated by its interaction with Fdxr.
Figure 5B:
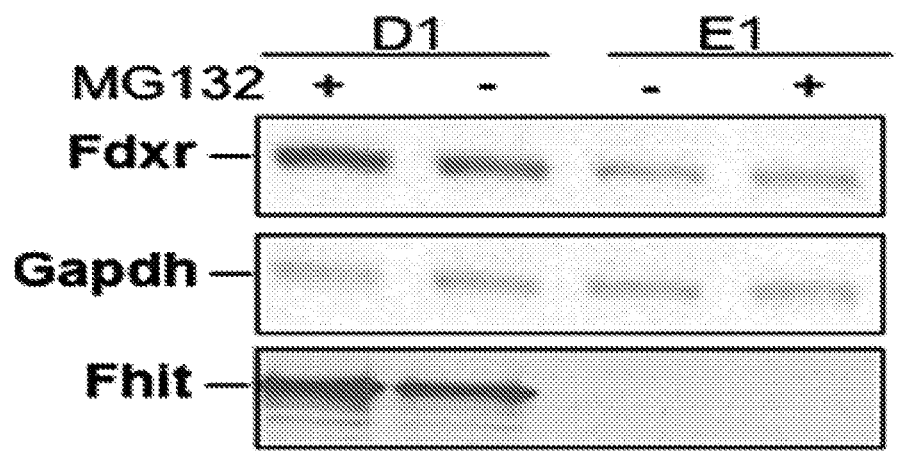
Figure 5C:
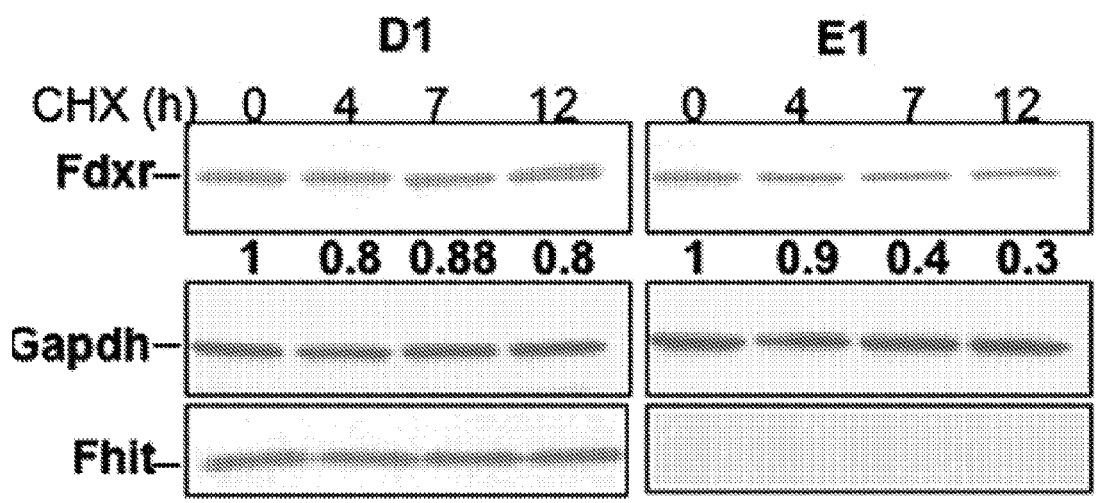
Figure 5D:
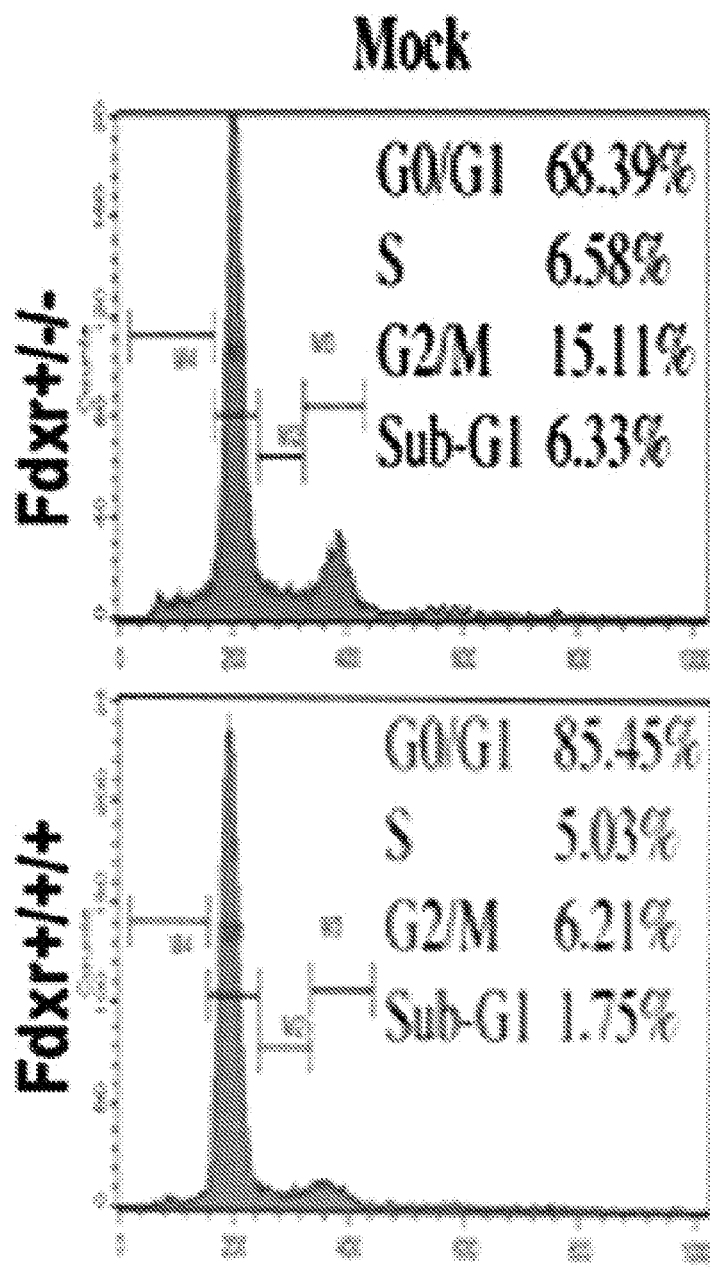
Figure 5D:
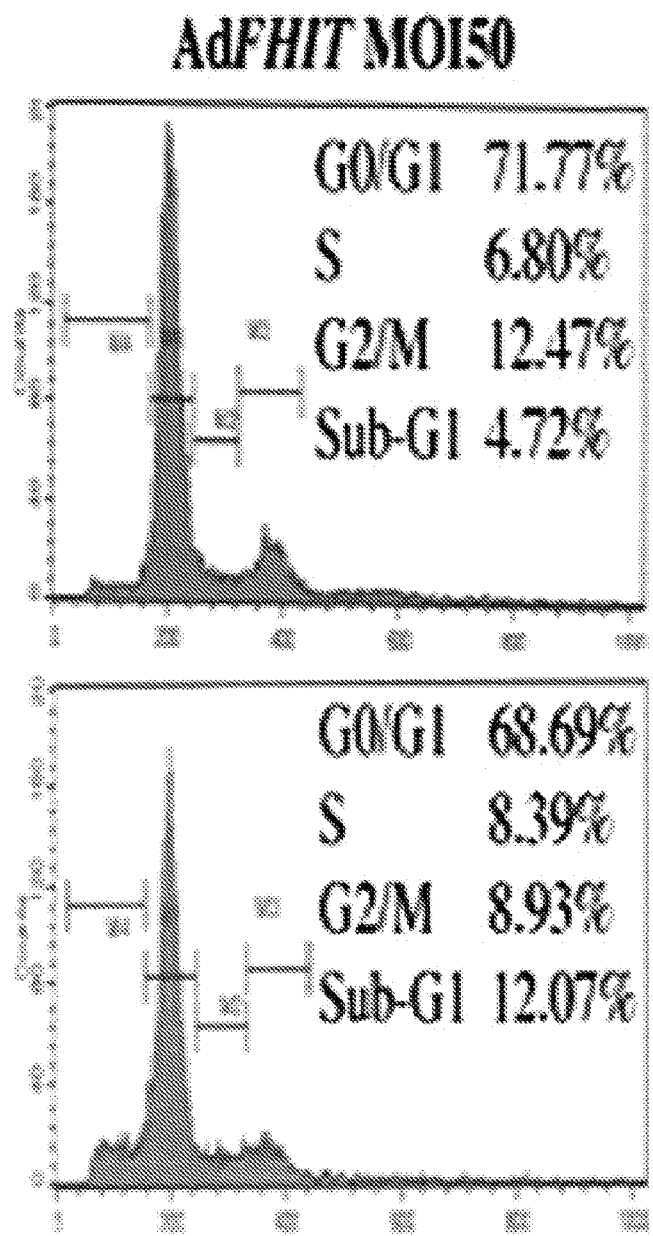
Figure 5D:
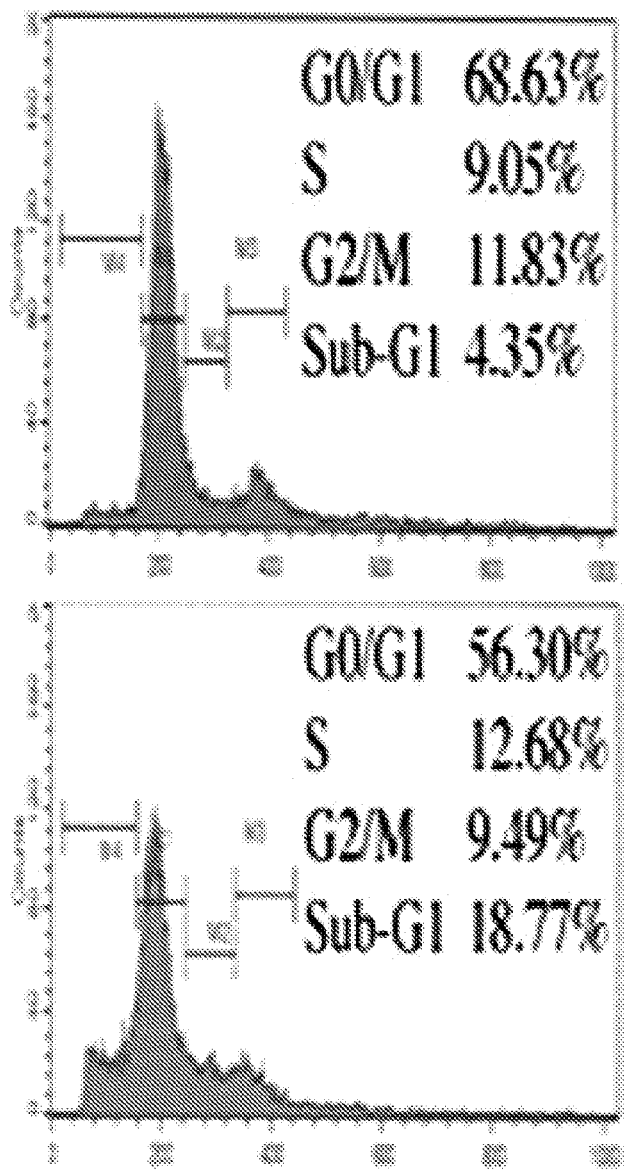
Figure 5E:
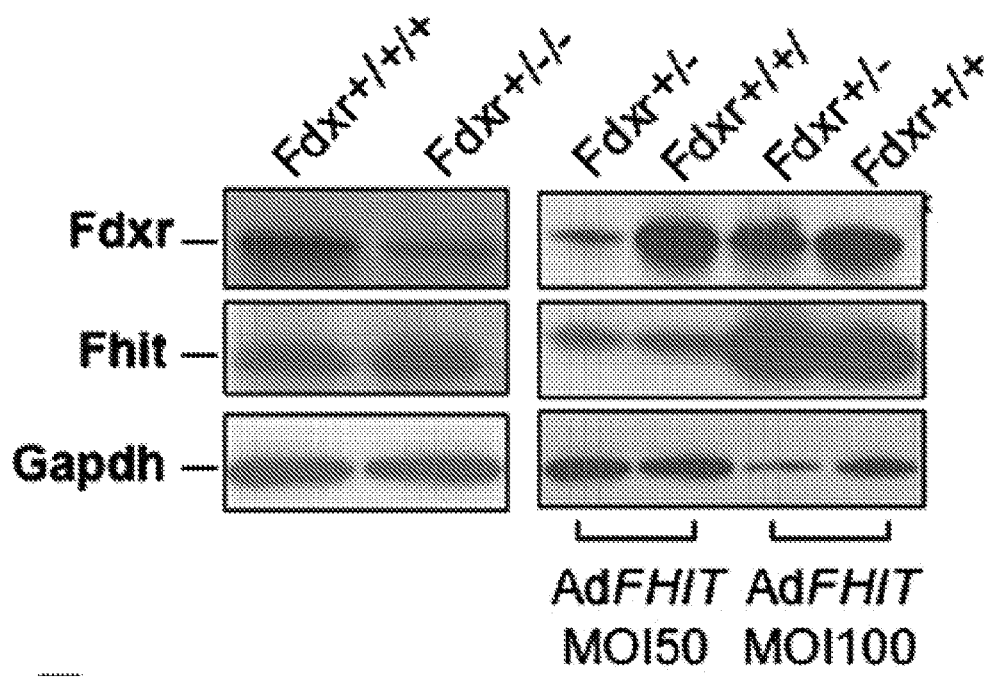
Figure 5F:
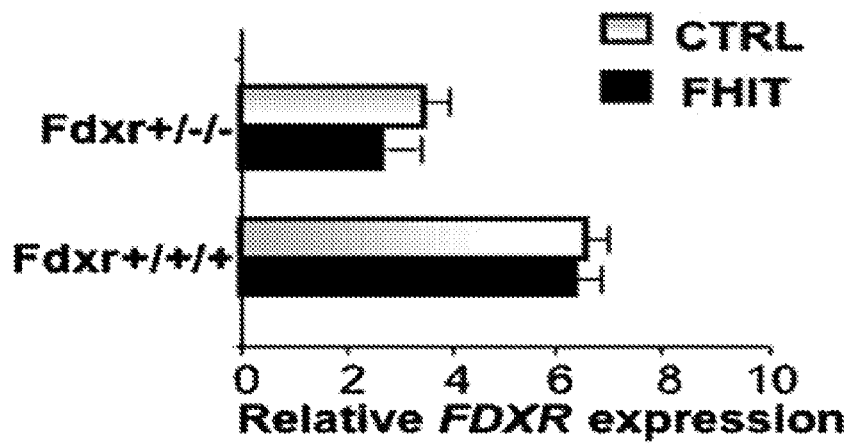

Fhit-induced ROS Generation Is Fdxr-dependent—To evaluate the role of Fdxr in Fhit-mediated ROS generation, the inventors examined the Fdxr level in D1 cells after Fhit induction and observed a 2.4-fold increase of its expression compared with E1 cells (FIG. 5A), an increase that was not due to increased transcription as determined by real time RT-PCR (FIG. 5F).

The inventors next measured the Fdxr level, with or without Fhit expression, in the presence of MG132, an inhibitor of proteasome degradation; 4 h after MG132 treatment a significant increase of Fdxr protein was observed in D1 cells compared with E1 cells (FIG. 5B), showing that Fhit protects Fdxr from proteasome degradation.

The rate of Fdxr degradation in the presence or absence of Fhit protein was evaluated by the 4-12-h CHX chase (FIG. 5C); the rate of Fdxr degradation was higher in Fhit-negative E1 cells (declining from 1 to 0.3) compared with D1 cells, with no significant decrease. Thus, the inventors herein now believe that Fhit prevents destabilization of the Fdxr protein by protecting it from proteasome degradation.

HCT116 colon cancer cells, which express endogenous wild-type p53 and Fhit and carry three FDXR alleles (FDXR$^{+/+/+}$), and HCT116FDXR$^{+/-/-}$ cells with two alleles knocked-out (28), were used to determine whether AdFHIT-induced apoptosis is influenced by the Fdxr expression level; the FDXR null condition was not compatible with viability (29).

These cells were infected with AdFHIT m.o.i. 50 or 100 and assessed for apoptosis at 48 and 72 h post-infection. Wild-type HCT116 cells (FDXR$^{+/+/+}$) were susceptible to exogenous Fhit-mediated apoptosis in a dose-dependent manner, as the fraction of sub-$G_1$ cells was 12.1 and 18.8% at m.o.i. 50 and 100, respectively; FDXR$^{+/-/-}$ cells were refractory at 48 and 72 h (data not shown) to Fhit-induced cell death, with a sub-$G_1$ population of 4.7 and 4.3% at m.o.i. 50 and 100 (FIG. 5D).

Fhit overexpression led to increased Fdxr protein levels in both FDXR$^{+/+/+}$ and FDXR$^{+/-/-}$ cells (FIG. 5E) and FDXR$^{+/-/-}$ cells were committed to Fhit-mediated apoptosis by 72 h after infection.

The Fhit-mediated increase of Fdxr expression was not at the transcriptional level, as determined by real time RT-PCR (FIG. 5F) and thus not related to the p53 transcriptional activation.

Figure 5G:
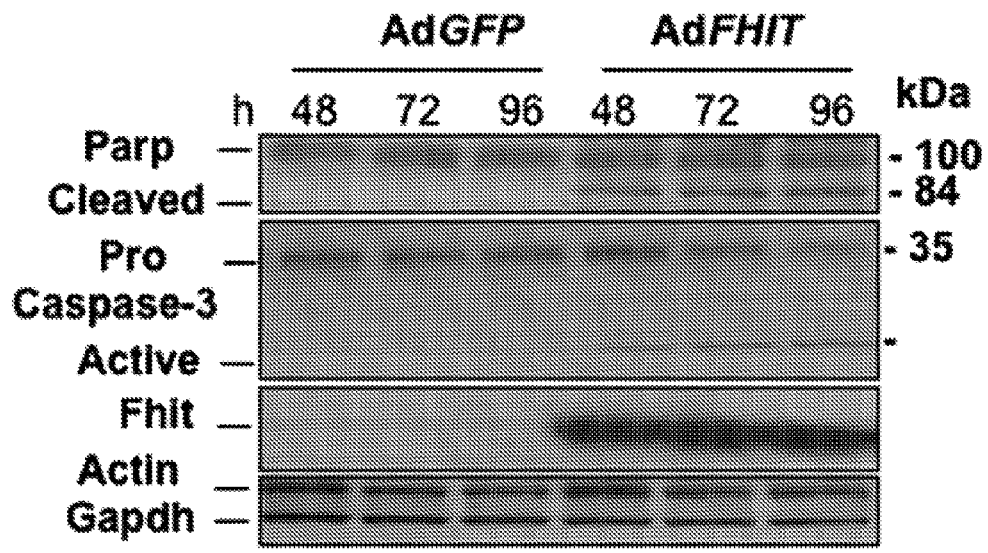

To better determine whether the sub-$G_1$ peak detected in FDXR$^{+/+/+}$ cells after AdFHIT infection was related to apoptosis induction, a time course experiment at 48, 72, and 96 h for caspase 3 and Parp 1 cleavage was performed and compared with AdGFP-infected cells (FIG. 5G).

Figure 5H:
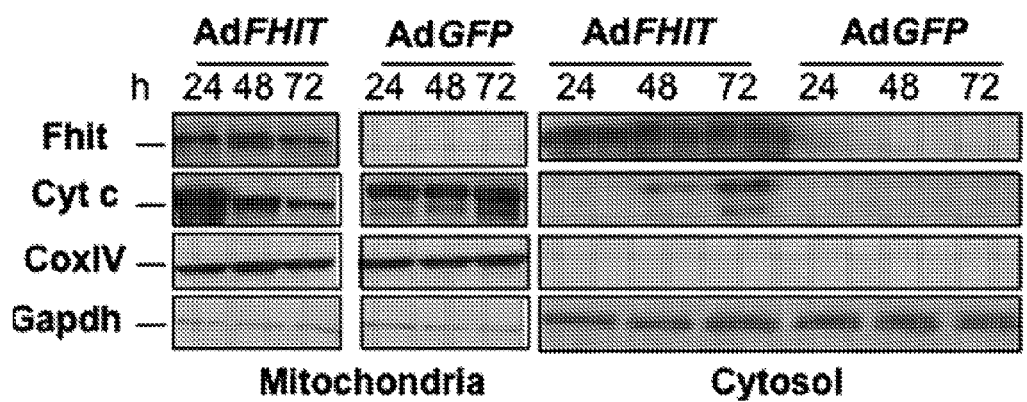

Caspase 3 cleavage and related Parp1 cleavage were observed at 48, 72, and 96 h after virus-mediated Fhit overexpression. The time course of cytochrome c release from mitochondria into cytosol was assessed after infection of HCT116 cells with AdFHIT m.o.i. 100 (FIG. 5H); progressive cytochrome c release was observed in HCT116 FDXR cells compared with GFP-infected cells, indicating initiation of the apoptotic cascade in Fhit overexpressing HCT116 FDXR$^{+/+/+}$ cells.

Fhit Enhances ROS-related Effects of Chemotherapeutic Agents—Generation of intracellular ROS is an early event in the apoptosis of lung cancer cells induced by treatment with paclitaxel (33). The inventors tested paclitaxel on H1299 D1 and E1 cells with or without induced Fhit expression. After induction of Fhit expression, D1 cells were more sensitive to paclitaxel than E1 cells (FIG. 6A) as measured by the MTS cell viability test. Cisplatin induces Fdxr expression and the cisplatin-induced apoptotic pathway is associated with ROS generation (34).

Fhit expressing D1 cells were more sensitive than E1 cells to cisplatin, measured by MTS assay at 24 and 48 h (FIG. 6B).

To examine cell viability after drug treatment, we performed flow cytometry analysis (FIG. 6, FIG. 6C and FIG. 6D); PonA-induced D1 and E1 cells treated with increasing paclitaxel concentrations (50-500 ng/ml) showed increasing sub-$G_1$ populations at 48 h: 9.6, 36, and 40%, respectively, for D1 cells compared with 4, 16.7, and 30% of E1 cells (FIG. 6C).

Similarly, increasing cisplatin concentrations (0.05-0.2 mM) led to increased sub-$G_1$ populations at 48 h: 5, 16.2, and 30%, respectively, in D1 cells, compared with 2.3, 7, and 14.6% of E1 cells (FIG. 6C).

At 24 and 72 h (data not shown) increased sub-$G_1$ populations in D1 compared with E1 cells were also detected. To determine whether the sub-$G_1$ fractions of D1 cells represented apoptotic cells, lysates were prepared from drug-treated cells at 48 h and immunoblot analysis performed for caspase 3 and Parp1 cleavage (FIG. 6D).

Activated caspase 3 and related Parp1 cleavage was observed after paclitaxel (50 and 100 ng/ml) and cisplatin (0.05 and 0.1 mM) treatments compared with untreated cells (Ctrl). The inventors herein now believe that Fhit expression increases sensitivity to oxidative injury through participation with Fdxr in ROS generation.

Example I

Materials and Methods

Cells, Vectors, and Antisera—A549, H1299, MKN74-E4, and A116, and HCT116 cells were maintained in RPMI 1640 medium plus 10% fetal bovine serum and penicillin/streptomycin (Sigma). HEK293 cells (Microbix) used for preparation of recombinant adenoviruses were cultured in Dulbecco's modified Eagle's medium plus 10% fetal bovine serum and penicillin/streptomycin. AdFHIT-His6 virus was prepared as described in Example II herein. [His6—SEQ ID NO: 32] [penta-His—SEQ ID NO: 33].

Full-length FDXR was amplified from human brain cDNAs (Clontech), subcloned into the pcDNA3.1/V5-His-TOPO TA vector (Invitrogen) and sequenced; details are as described under supplemental Methods. Cells were transfected using Lipofectamine™ (Invitrogen) following the manufacturer's directions.

Western Blot Analysis—Immunoblot analyses were performed as described (13) using monoclonal anti-pentaHis (Qiagen); rabbit polyclonal anti-Fhit (Zymed Laboratories Inc.); rabbit polyclonal antisera against GFP, Hsp60, Hsp10, and cytochrome c (Santa Cruz Biotechnology); rabbit polyclonal anti-Fdxr (Abcam); monoclonal anti-CoxIV (Molecular Probes); anti-V5 (Sigma); anti-Parp1 (Santa Cruz Biotechnology); and anti-caspase 3 (Cell Signaling). Protein levels were normalized relative to β-actin or/and GAPDH[3] level, detected with appropriate antisera (Santa Cruz Biotechnology).

Mass Spectrometry Studies—Protein pellets were solubilized and digested by trypsin as described herein. Peptide mixtures were injected for LC-MS/MS analysis. After protein identification by data base search, inspection of LC-MS/MS data was undertaken to assess the exclusive presence of mass peaks belonging to candidate partner proteins in samples from cells infected with AdFHIT-His6.

Protein Interaction Analyses—Proteins were extracted in 15 mM Tris-Cl, pH 7.5, 120 mM NaCl, 25 mM KCl, 2 mM EGTA, 0.1 mM dithiothreitol, 0.5% Triton X-100, 10 mg/ml leupeptin, 0.5 mM phenylmethylsulfonyl fluoride. Co-immunoprecipitation experiments, with or without dithiobis(succinimidyl propionate) (DSP), were performed by incubating 1 mg of total proteins with Hsp60, Hsp10, Fdxr, penta-His, and V5 antisera conjugated with Sepharose for 2 h at 4° C.; after washing, beads were boiled in 1×SDS sample buffer and proteins separated on 4-20% polyacrylamide gels (Bio-Rad), transferred to a poly(vinylidene difluoride) filter (Millipore), and probed with specific antisera.

Subcellular Localization of Fhit Protein—Fhit was sublocalized in ponasterone A (PonA)-induced, Fhit-expressing H1299 D1 cells by indirect immunofluorescence detection using anti-Fhit serum and by detection of FhitHis6 in A549 AdFHIT-His$_6$-infected cells in immunoelectron micrographs using anti-pentaHis. In fractionation studies, mitochondria were isolated with the Mitochondria/Cytosol Fractionation kit and the FractionPREP™ Cell Fractionation System was used to extract proteins from cytosol, membranes, nuclei, and cytoskeleton (Biovision Research Products). For submitochondrial localization according to the method of Dahéron et al. (22), mitochondria were resuspended in 0.1 M sodium carbonate, pH 11.5, on ice for 30 min with periodic vortexing and fractionated as described herein.

Flow Cytometry—HCT116 FDXR$^{+/+/+}$ and FDXR$^{+/-/-}$ cells were infected with AdFHIT or AdGFP at m.o.i. 50 and 100 and assessed at 48 h postinfection. PonA-induced H1299 D1 and E1 cells were treated with 0.25 and 0.5 mM H$_2$O$_2$ or with chemotherapeutic drugs and incubated for varying times, as indicated in the text and figures. For both experiments the cells were collected, washed with phosphate-buffered saline, and resuspended in cold 70% ethanol. For analysis, cells were spun down, washed in phosphate-buffered saline, and suspended in 0.1 mg/ml propidium iodide/Triton X-100 staining solution (0.1% Triton X-100, 0.2 mg/ml DNase-free RNase A) for 30 min at room temperature and analyzed by flow cytometry.

Assessment of Intracellular Reactive Oxygen Species (ROS)—Intracellular superoxide was measured through ethidium fluorescence as a result of oxidation by hydroethidine (dihydroethidium-HE; Molecular Probes). MNK74 stably Fhit expressing cells, A549 cells transiently expressing Fhit, and H1299 inducible Fhit expressing cells were treated with 0.5, 1.0, 2.0, and 4.0 mM H$_2$O$_2$ at 37° C.; 4 h later, hydroethidine (10 μM) was added to cells and incubated for 15 min at 37° C. Fluorescence was measured by flow cytometry. Dichlorofluorescein diacetate (DCFH-DA) (Molecular Probes) was used in D1 cells expressing induced Fhit, stressed with H$_2$O$_2$ (0.1 to 1.0 mM), treated with 10 μM DCFH-DA, and incubated for 1 h at 37° C. DCF fluorescence was measured by flow cytometry on a FAC-Scan flow cytometer and fluorescence microscopy.

Hsp60 and Hsp10 Silencing—A549 lung cancer cells at 8×10$^5$/well (6 wells plate) were transfected by Lipofectamine 2000 reagent (Invitrogen) and 6 μg of Hsp60 and/or Hsp10 siRNAs (Dharmacon catalog numbers NM_002156 [GenBank] and NM_002157 [GenBank], respectively); 48 h later cells were infected with AdFHIT at m.o.i. 1 and collected for cytosol/mitochondria protein fractionation 24 h later. Proteins were analyzed by SDS-PAGE and immunoblotting; filters were probed with Hsp60, Hsp10, and Fhit antisera. Protein loading was normalized with GAPDH and CoxIV. 1×10$^6$ H1299 D1 and E1 lung cancer cells were transfected as described above and 24 h after transfection the cells were PonA-induced; 48 h after induction a cycloheximide (CHX) (10 μg/ml) chase at 1, 4, 6, and 12 h was performed and the protein lysates were analyzed as described herein.

Real-time RT-PCR—Total RNA isolated with TRIzol reagent (Invitrogen) was processed after DNase treatment (Ambion) directly to cDNA by reverse transcription using SuperScript First-Strand (Invitrogen). Target sequences were amplified by qPCR using Power SYBR Green PCR Master Mix (Applied Biosystems). FDXR primers were: forward, 3'-TCGACCCAAGCGTGCCCTTTG-5' [SEQ ID No. 24]; reverse, 3'-GTGGCCCAGGAGGCGCAGCATC-5' [SEQ ID No. 25]. Samples were normalized using Actin and GADPH genes.

Chemotherapeutic Drug Treatment—Paclitaxel (Sigma) was dissolved in DMSO as a 10 mmol/liter stock solution and stored at −80° C. Cisplatin (Sigma) was dissolved in water and freshly prepared before use. H1299 D1 and E1 cells were seeded (1×10$^4$ cells/well) in 96-well culture plates, PonA-induced, and after 24 h treated with paclitaxel (50, 100, and 500 ng/ml) or cisplatin (0.05, 0.1, and 0.2 mM). H1299 D1 and E1 cells PonA-induced were incubated for 24, 48, and 72 h and assessed for viability with an MTS kit (Cell Titer 96® Aqueous MTS kit, Upstate Biotechnology, Lake Placid, N.Y.), as recommended by the manufacturer.

Example III

Generation of recombinant adenoviruses—The recombinant adenovirus carrying the wild-type FHIT cDNA (AdFHIT) was prepared as previously described (Ishii et al, 2001 Cancer Res 61:1578-1584). A His-tagged FHIT cDNA was generated by PCR with the following oligonucleotides: 5'-ACgTggATCCCTgTgAggACATgTCgT-TCAgATTTggC-3' (forward) [SEQ ID NO: 26] and 5'-TTgTggATCCTTATCAgTgATggTgATg-gTgATgCgATCCTCTCTgAAAgTAgCCCgCAg-3' [SEQ ID NO: 27]. These primers were designed with a BamHI restriction site for subcloning into the transfer vector pAdenoVator-CMV5-IRES-GFP. The Ad-His6 was generated with the AdenoVator™ kit (Qbiogene, Carlsbad, Calif.), following the manufacturer's procedure. Ad GFP, used as control, was purchased from Qbiogene (Carlsbad, Calif.).

Generation of a recombinant expression vector carrying FDXR cDNA-Wild-type ferredoxin reductase full-length was amplified from human brain cDNAs (Clontech, Palo Alto, Calif.) with primers: 5'-CTgTTCCCAgCCATggCT-TCgCgCTg-3' (forward) [SEQ ID NO: 28] and 5'-TCAgTg-gCCCAggAggCgCAgCATC-3' [SEQ ID NO: 29]. The amplification products were subcloned into the pcDNA3.1/V5-HisTOPO TA vector (Invitrogen, Carlsbad, Calif.). Sequencing excluded mutations in the amplified products.

For the preparation of a V5-tagged ferredoxin reductase cDNA, PCR amplification was performed with the same primer sequences with the exclusion of the FDXR physiological stop codon in the reverse primer. That is, both wild-type and V5-tagged ferredoxin reductase (FDXR) cDNAs were prepared by using as a template the wild-type coding sequence of the human ferredoxin reductase gene (GenBank Accession # NM_024417). The ferredoxin reductase coding sequence was amplified from human brain cDNAs (Clontech).

The primers used to generate the V5-tagged FDXR cDNA were: Forward: 5'-CTgTTCCCAgCCATggCTTCgCgCTg-3' [SEQ ID NO: 30]; and Reverse: 5'-gTggCCCAggAggCg-CAgCATC-3' [SEQ ID NO: 31]. It is to be noted that the oligonucleotide sequences are identical except for the reverse primer used for the generation of the V5-tagged cDNA, where the physiological stop codon of the FDXR was omitted in order to fuse in frame the FDXR coding sequence with a V5-tag.

The amplification products were subcloned into the pcDNA3.1/V5-HisTOPO TA vector (Invitrogen, Carlsbad, Calif.). Sequencing excluded mutations in the amplified products.

In certain embodiments, the adenovirus being capable of isolating Fhit-His6, comprises an adenovirus carrying a FHIT-His6 cDNA. The FHIT-His6 cDNA can be prepared by using as a template the wild-type coding sequence of the human FHIT gene (GenBank Accession # NM_002012). In order to introduce a polyhistidine-tag at the C-terminus of final Fhit product, a PCR amplification of the wild-type FHIT coding sequence was carried out with a reverse primer designed to abolish the physiological stop codon and to add to the endogenous FHIT sequence a stretch of 18 by coding for six hystidines followed by an artificial stop codon. Furthermore, both forward and reverse primers carried a BamHI restriction site for an easy subcloning. The oligonucleotide sequences used for this amplification were the following: Forward: 5'-ACgTggATCCCTgTgAggACATgTCgT-TCAgATTTggC-3' [SEQ ID NO: 26]; and Reverse: 5'-TTgTggATCCTTATCAgTgATggTgATg-gTgATgCgATCCTCTCTgAAAgTAgACCCgCAg-3' [SEQ ID NO: 27]. The PCR amplification product was sequenced to exclude random mutations before to be cloned in an Ad5 recombinant genome (AdenoVator™, a vector purchased by Qbiogene).

In certain embodiments, a method of isolating exogenously over-expressed Fhit-His6 includes using an adenovirus carrying a FHIT-His6 cDNA wherein the Fhit-His6 is isolated through the His tag. Fhit-His6 represents the recombinant protein whose expression is driven into a mammalian cell through the Ad FHIT-His6 vector. The His6 epitope allows for the recovery of the recombinant Fhit-His6 protein plus the protein complex interacting with the recombinant protein itself by taking advantage of the Ni-NTA system. This system is commercially available from Qiagen. Briefly, human A549 cancer cells were infected with Ad FHIT-His6; forty-eight hours after infection, photo-cross-linking of intracellular protein complexes was performed with the cross-linker dithiobis (succinimidyl propionate) [DSP] purchased from Pierce in order to stabilize protein complexes in living cells. Cells were disrupted in a protein extraction buffer and Fhit-His6 protein complex was isolated with the Ni-NTA magnetic-bead technology by taking advantage of the great affinity of the His6 tag for such beads. The isolated Fhit-His6 protein complex was then investigated through mass spectrometry to identify all proteins present in the complex.

In certain embodiments, a recombinant adenovirus carrying fragile histidine triad (Fhit) FHIT cDNA can be modified at its 3' with a sequence encoding a histidine-six epitope tag (AdFHIT-His6).

In certain embodiments, a method for mediating an apoptotic process in at least one cell, comprises exposing the cell to a fragile histidine triad (Fhit) gene product in an amount sufficient to mediate the apoptotic process in the cell.

In certain embodiments, a method for inducing an apoptosis process in a cell, comprises exposing the cell to a fragile histidine triad (Fhit) gene product in an amount sufficient to cause generation of reactive oxygen species (ROS) in the cell.

In certain embodiments, a method for mediating an apoptotic process in at least one cell, comprising: exposing the cell to a sufficient amount of fragile histidine triad (Fhit) gene product to allow the Fhit to enter mitochondria in the cell and to interact with Fdxr protein in the cell and to cause an increase in Fdxr protein level that is associated with generation of ROS, and causing a change in the apoptotic process in the cell.

It is to be noted that in previous studies, it was extensively proved that Fhit protein overexpression in Fhit-negative cancer cells is able to trigger programmed cell death (or apoptosis). In the instant invention, the inventors provide a rationale about the role of Fhit protein in the process of apoptosis. In fact, FHIT gene therapy of cancer cells performed with Ad FHIT (at the multiplicity of infection 50 or MOI50, i.e., 50 viral particles per cell) is responsible of Fhit overexpression; then, the newly synthesized recombinant protein is taken by its interactors Hsp60/Hsp10 from the cytosol to the mitochondria where Fhit interacts with FDXR (ferredoxin reductase) a protein belonging to the respiratory chain. This interaction leads to the mitochondrial generation of ROS (Reactive Oxygen Species). ROS represent the early step for the initiation of the intrinsic (or mitochondrial) pathway of the apoptotic process; in fact, they induce a damage in the mitochondrial membranes that, in turn, release cytochrome c into the cytosol. This step is crucial for the execution of apoptosis, as cytochrome c contributes with other cytosolic molecules (i.e., Apaf-1 and pro-caspase 3) to the generation of the apoptosome, a multiprotein complex able to drive the cell, in a non-reversible fashion, to apoptosis.

A method commonly used to study apoptosis consists in the detection of mature caspase-3 (an indicator of incipient apoptosis) by flow cytometric analysis (Becton Dickinson) [for reference, see Trapasso et al., 2003, PNAS, 100, 1592-1597].

In certain embodiments, a method for preparing a V5-tagged ferredoxin reductase cDNA, comprises PCR amplifying with primer sequences: 5'-CTgTTCCCAgC-CATggCTTCgCgCTg-3' (forward) [SEQ ID NO: 28]. and 5'-TCAgTggCCCAggAggCgCAgCATC-3' [SEQ ID NO: 29] and subcloning the amplification products pcDNA3.1/V5-HisTOPO TA vector.

Both wild-type and V5-tagged ferredoxin reductase (FDXR) cDNAs were prepared by using as a template the wild-type coding sequence of the human ferredoxin reductase gene (GenBank Accession # NM_024417). The ferredoxin reductase coding sequence was amplified from human brain cDNAs (Clontech). That is, the primers used to amplify the wild-type FDXR cDNA were: Forward: 5'-CTgTTCCCAgC-CATggCTTCgCgCTg-3' [SEQ ID NO: 28]; Reverse: 5'-TCAgTggCCCAggAggCgCAgCATC-3' [SEQ ID NO: 29].

The primers used to generate the VS-tagged FDXR cDNA were: Forward: 5'-CTgTTCCCAgCCATggCTTCgCgCTg-3' [SEQ ID NO: 30], and Reverse: 5'-gTggCCCAggAggCg-CAgCATC-3' [SEQ ID NO: 31]. Note that the oligonucleotide sequences are identical except for the reverse primer used for the generation of the V5-tagged cDNA, where the physiological stop codon of the FDXR was omitted in order to fuse in frame the FDXR coding sequence with a V5-tag.

Finally, the two products were subcloned in the pcDNA3.1/V5-HisTOPO TA expression vector (purchased from Invitrogen) and then sequenced to assess that both products had no random mutations.

In certain embodiments, a method for generating a recombinant adenovirus, comprises preparing a recombinant adenovirus carrying the wild-type FHIT cDNA (AdFHIT); and generating a His-tagged FHIT cDNA using PCR with the following oligonucleotides: 5'-ACgTggATCCCTgTgAggA-CATgTCgTTCAgATTTggC-3' (forward) [SEQ ID NO: 26], and 5'-TTgTggATCCTTATCAgTgATggTgATg-gTgATgCgATCCTCTCTgAAAgTAgACCCgCAg-3' [SEQ ID NO: 27]. The FHIT-His6 cDNA was prepared as described herein. The recombinant adenoviral vector Ad FHIT-His6 was prepared according to the manufacturer's suggestions (Qbiogene). Briefly, the amplified FHIT-His6 PCR fragment was digested with BamHI and subcloned into the BamHI linearized transfer vector pAdenoVator-CMV5-IRES-GFP. The pAdenoVator-CMV5-IRES-GFP/FHIT-His6 was co-transfected with the E1/E3 deleted Ad5 backbone viral DNA into 293 cells. Viral plaques were screened for the presence of the Fhit-His6 protein by Western blot with specific penta-His antibodies (Qiagen). One positive clone was plaque-purified and amplified on 293 cells. After freeze/thaw cycles, the adenoviruses in the supernatant were purified on two successive cesium chloride gradients. The recombinant adenovirus was titered by the TCID50 method and aliquoted. Virus stocks were stored at −80° C. Finally, the recombinant adenovirus carrying the wild-type FHIT cDNA (Ad FHIT) was previously generated by Trapasso et al. (2003, PNAS, 100, 1592-1597).

Mitochondrial localization studies—Confocal microscopy was used to assess Fhit protein distribution by immunofluorescence; H1299 D1 cells, with inducible FHIT cDNA, and E1 cells, with empty vector, were treated with PonA for 48 hr, and living cells were stained with Mitotracker Red 580 (M−22425, Molecular Probes, Eugene, Oreg.) at a working concentration of 500 nM for 40 min under growth conditions. The cells were fixed and permeablilized by incubation in ice-cold acetone for 5 min and then washed in PBS. Cells were incubated for 1 hr with 5% BSA to block non-specific interactions and than incubated overnight with Fhit antiserum (Zymed, S. San Francisco, Calif.) at a working concentration of 1.6 µg/ml, washed with PBS and incubated with Alexa Fluor 488 donkey anti-rabbit IgG (Molecular Probes). The slides were mounted in mounting medium for fluorescence with DAPI (Vector, Burlingane, Calif.) and visualized. For immunoelectron microscopy localization of Fhit, A549 cells infected with AdHis6 or AdFHIT, MOI 5, were fixed in 4% paraformaldehyde in PBS pH7.2 for 30 min at 4° C., washed 3 times with PBS, and remaining free aldehyde groups were reduced using a 30 min incubation in 0.05% sodium borohydride in PBS. Following a PBS wash, samples were blocked with 50 mM glycine in PBS for 30 min, washed twice in PBS, and dehydrated with 25 and 50% ethanol for 15 min each, followed by 3 changes of 70% ethanol for 15 min each. The samples were then infiltrated with 70% ethanol+LR White resin, hard grade (Electron Microscopy Sciences, Hatfield, Pa.) at 2:1 for 1 hr, 70% ethanol+LR White at 1:2 for 1 hr, 100% LR White for 1 hr and 100% LRW overnight at 4° C. The following day the cells received 2 more changes of 100% LR White and were polymerized in gelatin capsules at 58° C. for 20-24 hr. 900 nm thin sections were cut using a Reichert UCT Ultramicrotome and a diamond knife and placed on nickel grids. The grids were floated section side down on drops of PBS for 5 min, 5% goat serum in PBS for 1 hr at room temperature (RT), and either Penta-His mouse monoclonal antibody at 20 mg/ml (Qiagen, Valencia, Calif.) diluted in PBS containing 0.1% BSA and 0.05% Tween −20 (BSA/Tw) or BSA/Tw alone overnight at 4° C. in a humidified chamber. The following day the grids were washed 6× for 5 min each using PBS and then incubated with h goat anti-mouse 10 nm colloidal gold conjugate (Ted Pella, Redding, Calif.) diluted 1:10 in BSA/Tw for 2 hrs at RT. The grids were washed 6× each for 5 min with PBS, rinsed with DI H2O and post-stained with 2.5% aqueous uranyl acetate for 3 min. Images were collected on a Tecnai 12 electron microscope equipped with a US1000 Gatan 2K digital camera.

Sample digestion and LC-MS/MS analysis—Proteins isolated with Ni-NTA beads were precipitated with cold acetone and resuspended in 6 M urea buffered at pH 8 with 0.1 M Tris-HCl. Protein reduction and alkylation was achieved, respectively, by the addition of DTT (final concentration 10 mM, 1 hr incubation at 37° C.) and iodoacetamide (final concentration 25 mM, 1 hr incubation at 37° C.). After neutralizing excess iodoacetamide with DTT (additional 5 mM), urea concentration was lowered to 1.5 M by dilution with 1 mM $CaCl_2$. Overnight digestion was carried out using 50 ng of TPCK-treated trypsin (Sigma). Total digestion solution volume was 100 µl.

Chromatography was performed on an Ultimate nano LC system from Dionex (Sunnyvale, Calif.). Digest mixtures (30 µl) were directly injected onto a Pepmap $C_{18}$ RP cartridge (0.3 mm ID×5 mm length) and washed for 10 minutes with H2O/trifluoroacetic acid (TFA)/acetonitrile 97.9:0.1:2 (v/v/v) before the RP trap was switched on-line to a 75 µm×150 mm Pepmap $C_{18}$ nano LC column. Gradient elution of peptides was achieved at 300 nl/min using a 45-min linear gradient going from 5% B to 50% B. Mobile phase A was H 20/acetonitrile/formic acid (FA)/TFA 97.9:2:0.08:0.02 (v/v/v/v); mobile phase B was H2O/acetonitrile/FA/TFA 4.9:95:0.08:0.02 (v/v/v/v).

MS detection was performed on an Applied Biosystems (Framingham, Mass.) QSTAR XL hybrid LC-MS/MS operating in positive ion mode, with nanoelectrospray potential at 1800 V, curtain gas at 15 units, CAD gas at 3 units. Information-dependent acquisition (IDA) was performed by selecting the two most abundant peaks for MS/MS analysis after a full TOF-MS scan from 400 to 1200 m/z lasting 2 seconds. Both MS/MS analyses were performed in enhanced mode (2 seconds/scan).

LC-MS/MS Data Analysis—MS/MS spectra were searched by interrogating the Swiss Prot database on the Mascot search engine (www.matrixscience.com) (accessed on June 2006). The following search parameters were used. MS tolerance: 50 ppm; MS/MS tolerance: 1 Da; methionine oxidized (variable modification); cysteine carbamidomethylated (fixed modification); enzyme: trypsin; max. missed cleavages: 1.

Protein lists obtained from, respectively, both A549 infected with Ad FHIT-His6 and control were compared, and proteins exclusively present in the A549-Ad FHIT-His6 list were kept for further validation. As a first validation procedure, LC-MS/MS raw data were inspected using selected ion chromatogram (SIC) displaying mode. By SIC comparison, it could be assessed the exclusive presence of the peptides of interest, identified as belonging to the six candidate proteins under examination, in the Ad FHIT-His6 sample. Such verification step already provided rather strong evidence for the specific capture of the six candidate protein. Also, these findings were further validated by biochemical and functional assays.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

REFERENCES

The references discussed above and the following references, to the extent that they provide exemplary procedural or other details supplementary to those set forth herein, are specifically incorporated herein by reference.

1. Ohta, M., Inoue, H., Cotticelli, M. G., Kastury, K., Baffa, R., Palazzo, J., Siprashvili, Z., Mori, M., McCue, P., Druck, T., Croce, C. M., and Huebner, K. (1996) *Cell* 84, 587-597.

2. Matsuyama, A., Shiraishi, T., Trapasso, F., Kuroki, T., Alder, H., Mori, M., Huebner, K., and Croce, C. M. (2003) *Proc. Natl. Acad. Sci. U.S.A.* 100, 14988-14993.
3. Huebner, K., and Croce, C. M. (2001) *Nat. Rev. Cancer* 1, 214-221.
4. Huebner, K., and Croce, C. M. (2003) *Br. J. Cancer* 88, 1501-1506.
5. Fong, L. Y., Fidanza, V., Zanesi, N., Lock, L., Siracusa, L., Mancini, R., Siprashvili, Z., Ottey, M., Martin, S. E., Druck, T., McCue, P. A., Croce, C. M., and Huebner, K. (2000) *Proc. Natl. Acad. Sci. U.S.A.* 97, 4742-4747.
6. Zanesi, N., Fidanza, V., Fong, L. Y., Mancini, R., Druck, T., Valtieri, M., Rudiger, T., McCue, P. A., Croce, C. M., and Huebner, K. (2001) *Proc. Natl. Acad. Sci. U.S.A.* 98, 10250-10255.
7. Dumon, K. R., Ishii, H., Fong, L. Y., Zanesi, N., Fidanza, V., Mancini, R., Vecchione, A., Baffa, R., Trapasso, F., During, M. J., Huebner, K., and Croce, C. M. (2001) *Proc. Natl. Acad. Sci. U.S.A.* 98, 3346-3351.
8. Ishii, H., Zanesi, N., Vecchione, A., Trapasso, F., Yendamuri, S., Sarti, M., Baffa, R., During, M. J., Huebner, K., Fong, L. Y., and Croce, C. M. (2003) *FASEB J.* 17, 1768-1770.
9. Siprashvili, Z., Sozzi, G., Barnes, L. D., McCue, P., Robinson, A. K., Eryomin, V., Sard, L., Tagliabue, E., Greco, A., Fusetti, L., Schwartz, G., Pierotti, M. A., Croce, C. M., and Huebner, K. (1997) *Proc. Natl. Acad. Sci. U.S.A.* 94, 13771-13776.
10. Ji, L., Fang, B., Yen, N., Fong, K., Minna, J. D., and Roth, J. A. (1999) *Cancer Res.* 59, 3333-3339.
11. Ishii, H., Dumon, K. R., Vecchione, A., Trapasso, F., Mimori, K., Alder, H., Mori, M., Sozzi, G., Baffa, R., Huebner, K., and Croce, C. M. (2001) *Cancer Res.* 61, 1578-1584.
12. Roz, L., Gramegna, M., Ishii, H., Croce, C. M., and Sozzi, G. (2002) *Proc. Natl. Acad. Sci. U.S.A.* 99, 3615-3620.
13. Trapasso, F., Krakowiak, A., Cesari, R., Arkles, J., Yendamuri, S., Ishii, H., Vecchione, A., Kuroki, T., Bieganowski, P., Pace, H. C., Huebner, K., and Croce, C. M. (2003) *Proc. Natl. Acad. Sci. U.S.A.* 100, 1592-1597.
14. Gorgoulis, V. G., Vassiliou, L. V., Karakaidos, P., Zacharatos, P., Kotsinas, A., Liloglou, T., Venere, M., Ditullio, R. A., Jr., Kastrinakis, N. G., Levy, B., Kletsas, D., Yoneta, A., Herlyn, M., Kittas, C., and Halazonetis, T. D. (2005) *Nature* 434, 907-913.
15. Bartkova, J., Horejsi, Z., Koed, K., Kramer, A., Tort, F., Zieger, K., Guldberg, P., Sehested, M., Nesland, J. M., Lukas, C., and Bartek, J. (2005) *Nature* 434, 864-870.
16. Wistuba, I. I., Lam, S., Behrens, C., Virmani, A. K., Fong, K. M., LeRiche, J., Samet, J. M., Srivastava, S., Minna, J. D., and Gazdar, A. F. (1997) *J. Natl. Cancer Inst.* 89, 1366-1373.
17. Mao, L., Lee, J. S., Kurie, J. M., Fan, Y. H., Lippman, S. M., Lee, J. J., Ro, J. Y., Broxson, A., Yu, R., Morice, R. C., Kemp, B. L., Khuri, F. R., Walsh, G. L., Hittelman, W. N., and Hong, W. H. (1997) *J. Natl. Cancer Inst.* 89, 857-862.
18. Sozzi, G., Pastorino, U., Moiraghi, L., Tagliabue, E., Pezzella, F., Ghirelli, C., Tornielli, S., Sard, L., Huebner, K., Pierotti, M. A., Croce, C. M., and Pilotti, S. (1998) *Cancer Res.* 58, 5032-5037.
19. Thavathiru, E., Ludes-Meyers, J. H., MacLeod, M. C., and Aldaz, C. M. (2005) *Mol. Carcinog.* 44, 174-182.
20. Ottey, M., Han, S. Y., Druck, T., Barnoski, B. L., McCorkell, K. A., Croce, C. M., Raventos-Suarez, C., Fairchild, C. R., Wang, Y., Huebner, K., and Croce, C. M. (2004) *Br. J. Cancer* 91, 1669-1677.
21. Ishii, H., Mimori, K., Inoue, H., Inagata, T., Ishikawa, K., Semba, S., Druck, T., Trapasso, F., Tani, K., Vecchione, A., Croce, C. M., Mori, M., and Huebner, K. (2006) *Cancer Res.* 66, 11287-11292.
22. Dahéron, L., Zenz, T., Siracusa, L. D., Brenner, C., and Calabretta, B. (2001) *Nucleic Acids Res.* 29, 1308-1316.
23. Gupta, S., and Knowlton, A. A. (2005) *J. Cell. Mol. Med.* 9, 51-58.
24. Fujiki, Y., Hubbard, A. L., Fowler, S., and Lazarow, P. B. (1982) *J. Cell Biol.* 93, 97-102.
25. Ichikawa, W., Ooyama, A., Toda, E., Sugimoto, Y., Oka, T., Takahashi, T., Shimizu, M., Sasaki, Y., and Hirayama, R. (2006) *Cancer Chemother. Pharmacol.* 58, 794-801.
26. Hard, F. U., and Hayer-Hartl, M. (2002) *Science* 295, 1852-1858.
27. Kimura, T., and Suzuki, K. (1967) *J. Biol. Chem.* 242, 485-491.
28. Hanukoglu, I., Rapoport, R., Weiner, L., and Sklan, D. (1993) *Arch. Biochem. Biophys.* 305, 489-498.
29. Hwang, P. M., Bunz, F., Yu, J., Rago, C., Chan, T. A., Murphy, M. P., Kelso, G. F., Smith, R. A., Kinzler, K. W., and Vogelstein, B. (2001) *Nat. Med.* 7, 1111-1117.
30. Liu, G., and Chen, X. (2002) *Oncogene* 21, 7195-7204.
31. Danial, N. N., and Korsmeyer, S. J. (2004) *Cell* 116, 205-219.
32. Ohashi, M., Kanai, F., Ueno, H., Tanaka, T., Tateishi, K., Kawakami, T., Koike, Y., Ikenoue, T., Shiratori, Y., Hamada, H., and Omata, M. (1999) *Gut* 44, 336-371.
33. Alexandre, J., Batteux, F., Nicco, C., Chereau, C., Laurent, A., Guillevin, L., Weill, B., and Goldwasser, F. (2006) *Int. J. Cancer* 119, 41-48.
34. Kerley-Hamilton, J. S., Pike, A. M., Li, N., DiRenzo, J., and Spinella, M. J. (2005) *Oncogene* 24, 6090-6100.
35. Shi, Y., Zou, M., Farid, N. R., and Paterson, M. C. (2000) *Biochem. J.* 352, 443-448.
36. Chaudhuri, A. R., Khan, I. A., Prasad, V., Robinson, A. K., Luduena, R. F., and Barnes, L. D. (1999) *J. Biol. Chem.* 274, 24378-24382.
37. Nishizaki, M., Sasaki, J., Fang, B., Atkinson, E. N., Minna, J. D., Roth, J. A., and Ji, L. (2004) *Cancer Res.* 64, 5745-5752.
38. Hendrick, J. P., and Hartl, F. U. (1993) *Annu. Rev. Biochem.* 62, 349-384.

What is claimed is:

1. A method for inducing an apoptosis process in a cell, comprising
exposing the cell to an exogenous fragile histidine triad (Fhit) gene product in an amount sufficient to cause generation of reactive oxygen species (ROS) in the cell; and
administering an oxidative stress to the cell, wherein the oxidative stress comprises peroxide, thereby inducing an apoptotic process in the cell.

2. A method for mediating an apoptotic process in at least one cell, comprising:
exposing the cell to a sufficient amount of an exogenous fragile histidine triad (Fhit) gene product to allow the Fhit to enter mitochondria in the cell and to interact with Fdxr protein in the cell, whereby the Fdxr resists proteosomal degradation and accumulates in the cell, thereby causing an increase in Fdxr protein level that is associated with generation of ROS, and
applying an oxidative stress to the cell, wherein the oxidative stress comprises peroxide, causing a change in the apoptotic process in the cell.

3. The method of claim 1, further comprising:
administering at least one chemotherapeutic agent.

4. The method of claim 3, wherein the at least one chemotherapeutic agent is selected from the group consisting of: paclitaxel and cisplatin.

* * * * *